US012655229B2

(12) United States Patent
Tinkelenberg et al.

(10) Patent No.: US 12,655,229 B2
(45) Date of Patent: Jun. 16, 2026

(54) ANTI-CERAMIDE ANTIBODIES

(71) Applicants: Memorial Sloan Kettering Cancer Center, New York, NY (US); Ceramedix Holding, LLC, New York, NY (US)

(72) Inventors: Arthur Tinkelenberg, New York, NY (US); Richard Kolesnick, New York, NY (US); Jordon Kuo-Ming Wang, San Carlos, CA (US); Yinan Wu, Belmont, CA (US); Yong Wang, Mountain View, CA (US); Raphael Levy, Belmont, CA (US)

(73) Assignees: Memorial Sloan Kettering Cancer Center, New YORK, NY (US); Ceramedix Holding, LLC, New York, NY (US)

( * ) Notice: Subject to any disclaimer, the term of this patent is extended or adjusted under 35 U.S.C. 154(b) by 741 days.

(21) Appl. No.: 17/912,286

(22) PCT Filed: Mar. 18, 2021

(86) PCT No.: PCT/US2021/022914
§ 371 (c)(1),
(2) Date: Sep. 16, 2022

(87) PCT Pub. No.: WO2021/188770
PCT Pub. Date: Sep. 23, 2021

(65) Prior Publication Data
US 2023/0167197 A1 Jun. 1, 2023

Related U.S. Application Data

(60) Provisional application No. 62/991,232, filed on Mar. 18, 2020.

(51) Int. Cl.
*C07K 16/44* (2006.01)
*A61P 37/06* (2006.01)
*C12N 15/63* (2006.01)

(52) U.S. Cl.
CPC .............. *C07K 16/44* (2013.01); *A61P 37/06* (2018.01); *C12N 15/63* (2013.01); *C07K*

2317/24 (2013.01); *C07K 2317/52* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 2019/0389970 A1 | 12/2019 | Rotolo et al. | |
| 2020/0078404 A1* | 3/2020 | Ports .................. | A61K 40/4215 |
| 2022/0348678 A1* | 11/2022 | Kolesnick ............ | A61K 9/0048 |

FOREIGN PATENT DOCUMENTS

| | | | | |
|---|---|---|---|---|
| JP | 2017-527544 A | 9/2017 | | |
| WO | WO-2010/021874 A2 | 2/2010 | | |
| WO | WO-2016022883 A1 * | 2/2016 | .............. | A61P 39/00 |
| WO | WO-2016112870 A1 * | 7/2016 | .............. | A61P 37/00 |
| WO | WO-2019237035 A1 * | 12/2019 | ......... | C12N 15/1138 |
| WO | WO-2021062355 A1 * | 4/2021 | ......... | C07K 16/2896 |
| WO | WO-2022/197703 A1 | 9/2022 | | |

OTHER PUBLICATIONS

Sela-Culang et al. The structural basis of antibody-antigen recognition. Fron. Immuno., vol. 4, Article 302, Oct. 2013. (Year: 2013).*
Herold et al. Determinants of the assembly and function of antibody variable domains. Nature Scientific Reports, 7:12276, Sep. 25, 2017. (Year: 2017).*
Biointron. The future of Therapeutics: Fully Human Antibodies. Aug. 21, 2024. Biointron blog. (Year: 2024).*
Foreign Search Report on PCT PCT/US2021/022914 Dtd Jul. 27, 2021.

* cited by examiner

*Primary Examiner* — Julie Wu
*Assistant Examiner* — Amy M. Chattin
(74) *Attorney, Agent, or Firm* — Foley & Lardner LLP

(57) ABSTRACT

The present disclosure provides compositions of anti-ceramide antibodies and antigen-binding fragments thereof. The disclosure further provides methods of preventing or inhibiting cell death in a subject in need thereof comprising administering the anti-ceramide antibodies or antigen-binding fragments to a subject. The subject in need thereof may suffer from an autoimmune disease, GI syndrome, or GvHD.

24 Claims, 10 Drawing Sheets

Specification includes a Sequence Listing.

VH1 (SEQ ID NO: 17)  QVQLVQSGAEVKKPGASVKVSCKASGYTFTDHTMHWVRQAPGQGLEWMGY
VH2 (SEQ ID NO: 18)  QVQLVQSGAEVKKPGASVKVSCKVSGYTFTDHTIHWMRQAPGQGLEWMGY
VH3 (SEQ ID NO: 19)  QVQLVQSGAEVKKPGATVKISCKVSGYTFTDHTIHWMQQAPGKGLEWMGY
                     *********** : *  *****     * *  ** *** *

VH1 (SEQ ID NO: 17)  NYPRDGSTKYAEKFQGRVTMTADKSTSTVYMELSSLRSEDTAVYYCAKGF
VH2 (SEQ ID NO: 18)  NYPRDGSTKYNEKFQGRVTMTADKSTSTVYMELSSLRSEDTAVYYCAKGF
VH3 (SEQ ID NO: 19)  NYPRDGSTKYNEKFQGRVTITADKSTSTAYMELSSLRSEDTAVYYCAKGF
                     ******** **** ***** ******************

VH1 (SEQ ID NO: 17)  ITTVVPSAYWGQGTLVTVSS
VH2 (SEQ ID NO: 18)  ITTVVPSAYWGQGTLVTVSS
VH3 (SEQ ID NO: 19)  ITTVVPSAYWGQGTLVTVSS
                     ********************

FIG. 4A

```
VL1 (SEQ ID NO: 22)   DIQLTQSPSFLSASVGDRVTITCRASKSISKYLAWYQQKPGKAPKLLIYS
VL2 (SEQ ID NO: 23)   DVQITQSPSFLSASVGDRVTITCRASKSISKYLAWYQQKPGKANKLLIYS
VL3 (SEQ ID NO: 24)   DVQLTQSPSSVSASVGDRVTITCRASKSISKYLAWYQQKPGKAPKLLIYS
                      *: :* .   ::****************************************

VL1 (SEQ ID NO: 22)   GSTLQSGVPSRFSGSGSGTEFTLTISSLQPEDFATYYCQQHNEYPWTFGG
VL2 (SEQ ID NO: 23)   GSTLQSGVPSRFSGSGSGTDFTLTISSLQPEDFATYYCQQHNEYPWTFGG
VL3 (SEQ ID NO: 24)   GSTLQSGVPSRFSGSGSGTDFTLTISSLQPEDFATYYCQQHNEYPWTFGP
                      *******************:******************************** ::

VL1 (SEQ ID NO: 22)   GTKVEIK
VL2 (SEQ ID NO: 23)   GTKVEIK
VL3 (SEQ ID NO: 24)   GTKVEIK
                      *******
```

FIG. 4B

SEQUENCE LISTING

<160> NUMBER OF SEQ ID NOS: 76

<210> SEQ ID NO 1
<211> LENGTH: 10
<212> TYPE: PRT
<213> ORGANISM: Artificial Sequence
<220> FEATURE:
<223> OTHER INFORMATION: HCDR1-IH

<400> SEQUENCE: 1

Gly Tyr Thr Phe Thr Asp His Thr Ile His
1               5                   10

<210> SEQ ID NO 2
<211> LENGTH: 10
<212> TYPE: PRT
<213> ORGANISM: Artificial Sequence
<220> FEATURE:
<223> OTHER INFORMATION: HCDR1-IH-MH

<400> SEQUENCE: 2

Gly Tyr Thr Phe Thr Asp His Thr Met His
1               5                   10

<210> SEQ ID NO 3
<211> LENGTH: 17
<212> TYPE: PRT
<213> ORGANISM: Artificial Sequence
<220> FEATURE:
<223> OTHER INFORMATION: HCDR2-DG

<400> SEQUENCE: 3

Tyr Asn Tyr Pro Arg Asp Gly Ser Thr Lys Tyr Asn Glu Lys Phe Gln
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: HCDR2-DG-EG

<400> SEQUENCE: 4

Tyr Asn Tyr Pro Arg Glu Gly Ser Thr Lys Tyr Asn Glu Lys Phe Gln
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: HCDR2-DG-DV

<400> SEQUENCE: 5

Tyr Asn Tyr Pro Arg Asp Val Ser Thr Lys Tyr Asn Glu Lys Phe Gln
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: HCDR2-NE-AE

<400> SEQUENCE: 6

Tyr Asn Tyr Pro Arg Asp Gly Ser Thr Lys Tyr Ala Glu Lys Phe Gln
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: HCDR3

<400> SEQUENCE: 7

Gly Phe Ile Thr Thr Val Val Pro Ser Ala Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: LCDR1

<400> SEQUENCE: 8

Arg Ala Ser Lys Ser Ile Ser Lys Tyr Leu Ala
1               5                   10

<210> SEQ ID NO 9
<211> LENGTH: 7
<212> TYPE: PRT
<213> ORGANISM: Artificial Sequence
<220> FEATURE:

```
<223> OTHER INFORMATION: LCDR2

<400> SEQUENCE: 9

Ser Gly Ser Thr Leu Gln Ser
1               5

<210> SEQ ID NO 10
<211> LENGTH: 9
<212> TYPE: PRT
<213> ORGANISM: Artificial Sequence
<220> FEATURE:
<223> OTHER INFORMATION: LCDR3

<400> SEQUENCE: 10

Gln Gln His Asn Glu Tyr Pro Trp Thr
1               5

<210> SEQ ID NO 11
<211> LENGTH: 10
<212> TYPE: PRT
<213> ORGANISM: Mus musculus

<400> SEQUENCE: 11

Gly Tyr Thr Phe Thr Asp His Thr Ile His
1               5                   10

<210> SEQ ID NO 12
<211> LENGTH: 17
<212> TYPE: PRT
<213> ORGANISM: Mus musculus

<400> SEQUENCE: 12

Tyr Asn Tyr Pro Arg Asp Gly Ser Thr Lys Tyr Asn Glu Lys Phe Lys
1               5                   10                  15

Gly

<210> SEQ ID NO 13
<211> LENGTH: 11
<212> TYPE: PRT
<213> ORGANISM: Mus musculus

<400> SEQUENCE: 13

Gly Phe Ile Thr Thr Val Val Pro Ser Ala Tyr
1               5                   10

<210> SEQ ID NO 14
<211> LENGTH: 11
<212> TYPE: PRT
<213> ORGANISM: Mus musculus

<400> SEQUENCE: 14

Arg Ala Ser Lys Ser Ile Ser Lys Tyr Leu Ala
1               5                   10

<210> SEQ ID NO 15
<211> LENGTH: 7
<212> TYPE: PRT
<213> ORGANISM: Mus musculus

<400> SEQUENCE: 15

Ser Gly Ser Thr Leu Gln Ser
1               5

<210> SEQ ID NO 16
```

```
<211> LENGTH: 9
<212> TYPE: PRT
<213> ORGANISM: Mus musculus

<400> SEQUENCE: 16

Gln Gln His Asn Glu Tyr Pro Trp Thr
1               5

<210> SEQ ID NO 17
<211> LENGTH: 120
<212> TYPE: PRT
<213> ORGANISM: Artificial Sequence
<220> FEATURE:
<223> OTHER INFORMATION: Humanized VH1

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Thr Met His Trp Val Arg Gln Ala Pro Gly Gln Gly Leu Glu Trp Met
            35                  40                  45

Gly Tyr Asn Tyr Pro Arg Asp Gly Ser Thr Lys Tyr Ala Glu Lys Phe
        50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Humanized VH2

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp His
                20                  25                  30

Thr Ile His Trp Met Arg Gln Ala Pro Gly Gln Gly Leu Glu Trp Met
            35                  40                  45

Gly Tyr Asn Tyr Pro Arg Asp Gly Ser Thr Lys Tyr Asn Glu Lys Phe
        50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser
        115                 120

<210> SEQ ID NO 19
```

```
<211> LENGTH: 120
<212> TYPE: PRT
<213> ORGANISM: Artificial Sequence
<220> FEATURE:
<223> OTHER INFORMATION: Humanized VH3

<400> SEQUENCE: 19

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
            20                  25                  30

Thr Ile His Trp Met Gln Gln Ala Pro Gly Lys Gly Leu Glu Trp Met
        35                  40                  45

Gly Tyr Asn Tyr Pro Arg Asp Gly Ser Thr Lys Tyr Asn Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser
        115                 120

<210> SEQ ID NO 20
<211> LENGTH: 120
<212> TYPE: PRT
<213> ORGANISM: Artificial Sequence
<220> FEATURE:
<223> OTHER INFORMATION: Humanized VH4

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp His
            20                  25                  30

Thr Ile His Trp Met Arg Gln Ala Pro Gly Gln Gly Leu Glu Trp Met
        35                  40                  45

Gly Tyr Asn Tyr Pro Arg Glu Gly Ser Thr Lys Tyr Asn Glu Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser
        115                 120

<210> SEQ ID NO 21
<211> LENGTH: 120
<212> TYPE: PRT
<213> ORGANISM: Artificial Sequence
<220> FEATURE:
<223> OTHER INFORMATION: Humanized VH5

<400> SEQUENCE: 21

Gln Val Gln Leu Val Gln Ser Gly Ala Glu Val Lys Lys Pro Gly Ala
1               5                   10                  15
```

-continued

```
Ser Val Lys Val Ser Cys Lys Val Ser Gly Tyr Thr Phe Thr Asp His
        20              25                  30

Thr Ile His Trp Met Arg Gln Ala Pro Gly Gln Gly Leu Glu Trp Met
        35              40                  45

Gly Tyr Asn Tyr Pro Arg Asp Val Ser Thr Lys Tyr Asn Glu Lys Phe
    50              55                  60

Gln Gly Arg Val Thr Met Thr Ala Asp Lys Ser Thr Ser Thr Val Tyr
65              70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser
            115             120

<210> SEQ ID NO 22
<211> LENGTH: 107
<212> TYPE: PRT
<213> ORGANISM: Artificial Sequence
<220> FEATURE:
<223> OTHER INFORMATION: Humanized VL1

<400> SEQUENCE: 22

Asp Ile Gln Leu Thr Gln Ser Pro Ser Phe Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Asn Glu Tyr Pro Trp
                85                  90                  95

Thr Phe Gly Gly Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Humanized VL2

<400> SEQUENCE: 23

Asp Val Gln Ile Thr Gln Ser Pro Ser Phe Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Trp
                85                  90                  95
```

```
Thr Phe Gly Gly Gly Thr Lys Val Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Humanized VL3

<400> SEQUENCE: 24

Asp Val Gln Leu Thr Gln Ser Pro Ser Ser Val Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
            35                  40                  45

Tyr Ser Gly Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Trp
                85                  90                  95

Thr Phe Gly Pro Gly Thr Lys Val Glu Ile Lys
            100                 105

<210> SEQ ID NO 25
<211> LENGTH: 20
<212> TYPE: PRT
<213> ORGANISM: Artificial Sequence
<220> FEATURE:
<223> OTHER INFORMATION: STD1 linker

<400> SEQUENCE: 25

Asn Tyr Gly Gly Gly Gly Ser Gly Gly Gly Gly Ser Gly Gly Gly Gly
1               5                   10                  15

Ser Gly Asn Ser
            20

<210> SEQ ID NO 26
<211> LENGTH: 38
<212> TYPE: PRT
<213> ORGANISM: Artificial Sequence
<220> FEATURE:
<223> OTHER INFORMATION: STD2 linker

<400> SEQUENCE: 26

Asn Tyr Gly Gly Gly Gly Ser Gly Gly Gly Gly Ser Gly Gly Gly Gly
1               5                   10                  15

Ser Gly Asn Tyr Gly Gly Gly Gly Ser Gly Gly Gly Gly Ser Gly Gly
            20                  25                  30

Gly Gly Ser Gly Asn Ser
        35

<210> SEQ ID NO 27
<211> LENGTH: 2
<212> TYPE: PRT
<213> ORGANISM: Artificial Sequence
<220> FEATURE:
<223> OTHER INFORMATION: H1 linker

<400> SEQUENCE: 27
```

-continued

```
Asn Ser
1

<210> SEQ ID NO 28
<211> LENGTH: 8
<212> TYPE: PRT
<213> ORGANISM: Artificial Sequence
<220> FEATURE:
<223> OTHER INFORMATION: H2 linker

<400> SEQUENCE: 28

Gly Gly Gly Gly Ser Gly Asn Ser
1               5

<210> SEQ ID NO 29
<211> LENGTH: 10
<212> TYPE: PRT
<213> ORGANISM: Artificial Sequence
<220> FEATURE:
<223> OTHER INFORMATION: H3 linker

<400> SEQUENCE: 29

Asn Tyr Gly Gly Gly Gly Ser Gly Asn Ser
1               5                   10

<210> SEQ ID NO 30
<211> LENGTH: 13
<212> TYPE: PRT
<213> ORGANISM: Artificial Sequence
<220> FEATURE:
<223> OTHER INFORMATION: H4 linker

<400> SEQUENCE: 30

Gly Gly Gly Gly Ser Gly Gly Gly Gly Ser Gly Asn Ser
1               5                   10

<210> SEQ ID NO 31
<211> LENGTH: 15
<212> TYPE: PRT
<213> ORGANISM: Artificial Sequence
<220> FEATURE:
<223> OTHER INFORMATION: H5 linker

<400> SEQUENCE: 31

Asn Tyr Gly Gly Gly Gly Ser Gly Gly Gly Gly Ser Gly Asn Ser
1               5                   10                  15

<210> SEQ ID NO 32
<211> LENGTH: 18
<212> TYPE: PRT
<213> ORGANISM: Artificial Sequence
<220> FEATURE:
<223> OTHER INFORMATION: H6 linker

<400> SEQUENCE: 32

Gly Gly Gly Gly Ser Gly Gly Gly Gly Ser Gly Gly Gly Gly Ser Gly
1               5                   10                  15

Asn Ser

<210> SEQ ID NO 33
<211> LENGTH: 8
<212> TYPE: PRT
<213> ORGANISM: Artificial Sequence
<220> FEATURE:
<223> OTHER INFORMATION: H7 linker
```

```
<400> SEQUENCE: 33

Gly Cys Pro Pro Cys Pro Asn Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Gly4Ser linker

<400> SEQUENCE: 34

Gly Gly Gly Gly Ser
1               5

<210> SEQ ID NO 35
<211> LENGTH: 15
<212> TYPE: PRT
<213> ORGANISM: Artificial Sequence
<220> FEATURE:
<223> OTHER INFORMATION: (G4S)3 linker

<400> SEQUENCE: 35

Gly Gly Gly Gly Ser Gly Gly Gly Gly Ser Gly Gly Gly Gly Ser
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: H105 linker

<400> SEQUENCE: 36

Ser Gly Gly Gly Gly Ser Gly Gly Gly Gly Ser Gly Gly Gly Gly Ser
1               5                   10                  15

<210> SEQ ID NO 37
<211> LENGTH: 20
<212> TYPE: PRT
<213> ORGANISM: Artificial Sequence
<220> FEATURE:
<223> OTHER INFORMATION: (G4S)4 linker

<400> SEQUENCE: 37

Gly Gly Gly Gly Ser Gly Gly Gly Gly Ser Gly Gly Gly Gly Ser Gly
1               5                   10                  15

Gly Gly Gly Ser
            20

<210> SEQ ID NO 38
<211> LENGTH: 21
<212> TYPE: PRT
<213> ORGANISM: Artificial Sequence
<220> FEATURE:
<223> OTHER INFORMATION: H75 linker (NKG2A quadruple mutant)

<400> SEQUENCE: 38

Gln Arg His Asn Asn Ser Ser Leu Asn Thr Gly Thr Gln Met Ala Gly
1               5                   10                  15

His Ser Pro Asn Ser
            20

<210> SEQ ID NO 39
<211> LENGTH: 16
```

```
<212> TYPE: PRT
<213> ORGANISM: Artificial Sequence
<220> FEATURE:
<223> OTHER INFORMATION: H83 linker (NKG2A derived)

<400> SEQUENCE: 39

Ser Ser Leu Asn Thr Gly Thr Gln Met Ala Gly His Ser Pro Asn Ser
1               5                   10                  15

<210> SEQ ID NO 40
<211> LENGTH: 18
<212> TYPE: PRT
<213> ORGANISM: Artificial Sequence
<220> FEATURE:
<223> OTHER INFORMATION: H106 linker (NKG2A derived)

<400> SEQUENCE: 40

Gln Arg His Asn Asn Ser Ser Leu Asn Thr Gly Thr Gln Met Ala Gly
1               5                   10                  15

His Ser

<210> SEQ ID NO 41
<211> LENGTH: 14
<212> TYPE: PRT
<213> ORGANISM: Artificial Sequence
<220> FEATURE:
<223> OTHER INFORMATION: H81 linker (NKG2D derived)

<400> SEQUENCE: 41

Glu Val Gln Ile Pro Leu Thr Glu Ser Tyr Ser Pro Asn Ser
1               5                   10

<210> SEQ ID NO 42
<211> LENGTH: 20
<212> TYPE: PRT
<213> ORGANISM: Artificial Sequence
<220> FEATURE:
<223> OTHER INFORMATION: H91 linker (NKG2D derived)

<400> SEQUENCE: 42

Asn Ser Leu Ala Asn Gln Glu Val Gln Ile Pro Leu Thr Glu Ser Tyr
1               5                   10                  15

Ser Pro Asn Ser
            20

<210> SEQ ID NO 43
<211> LENGTH: 19
<212> TYPE: PRT
<213> ORGANISM: Artificial Sequence
<220> FEATURE:
<223> OTHER INFORMATION: H94 linker

<400> SEQUENCE: 43

Ser Gly Gly Gly Gly Ser Gly Gly Gly Gly Ser Gly Gly Gly Gly Ser
1               5                   10                  15

Pro Asn Ser

<210> SEQ ID NO 44
<211> LENGTH: 19
<212> TYPE: PRT
<213> ORGANISM: Artificial Sequence
<220> FEATURE:
<223> OTHER INFORMATION: H111 linker

<400> SEQUENCE: 44
```

-continued

```
Ser Gly Gly Gly Gly Ser Gly Gly Gly Gly Ser Gly Gly Gly Gly Ser
1               5                   10                  15

Pro Gly Ser

<210> SEQ ID NO 45
<211> LENGTH: 19
<212> TYPE: PRT
<213> ORGANISM: Artificial Sequence
<220> FEATURE:
<223> OTHER INFORMATION: H113 linker

<400> SEQUENCE: 45

Ser Gly Gly Gly Gly Ser Gly Gly Gly Gly Ser Gly Gly Gly Gly Ser
1               5                   10                  15

Pro Ala Ser

<210> SEQ ID NO 46
<211> LENGTH: 18
<212> TYPE: PRT
<213> ORGANISM: Artificial Sequence
<220> FEATURE:
<223> OTHER INFORMATION: H114 linker

<400> SEQUENCE: 46

Ser Gly Gly Gly Gly Ser Gly Gly Gly Gly Ser Gly Gly Gly Gly Ser
1               5                   10                  15

Pro Ser

<210> SEQ ID NO 47
<211> LENGTH: 19
<212> TYPE: PRT
<213> ORGANISM: Artificial Sequence
<220> FEATURE:
<223> OTHER INFORMATION: H115 linker

<400> SEQUENCE: 47

Ser Gly Gly Gly Gly Ser Gly Gly Gly Gly Ser Gly Gly Gly Gly Ser
1               5                   10                  15

Pro Ser Ser

<210> SEQ ID NO 48
<211> LENGTH: 283
<212> TYPE: PRT
<213> ORGANISM: Artificial Sequence
<220> FEATURE:
<223> OTHER INFORMATION: VH2-VL1 (Lead) scFv

<400> SEQUENCE: 48

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Val Ser Gly Tyr Thr Phe
            35                  40                  45

Thr Asp His Thr Ile His Trp Met Arg Gln Ala Pro Gly Gln Gly Leu
        50                  55                  60

Glu Trp Met Gly Tyr Asn Tyr Pro Arg Asp Gly Ser Thr Lys Tyr Asn
65                  70                  75                  80

Glu Lys Phe Gln Gly Arg Val Thr Met Thr Ala Asp Lys Ser Thr Ser
                85                  90                  95

Thr Val Tyr Met Glu Leu Ser Ser Leu Arg Ser Glu Asp Thr Ala Val
```

-continued

```
                100                 105                 110

Tyr Tyr Cys Ala Lys Gly Phe Ile Thr Thr Val Val Pro Ser Ala Tyr
        115                 120                 125

Trp Gly Gln Gly Thr Leu Val Thr Val Ser Ser Gly Gly Gly Gly Ser
        130                 135                 140

Gly Gly Gly Gly Ser Gly Gly Gly Gly Ser Asp Ile Gln Leu Thr Gln
145                 150                 155                 160

Ser Pro Ser Phe Leu Ser Ala Ser Val Gly Asp Arg Val Thr Ile Thr
                165                 170                 175

Cys Arg Ala Ser Lys Ser Ile Ser Lys Tyr Leu Ala Trp Tyr Gln Gln
                180                 185                 190

Lys Pro Gly Lys Ala Pro Lys Leu Leu Ile Tyr Ser Gly Ser Thr Leu
        195                 200                 205

Gln Ser Gly Val Pro Ser Arg Phe Ser Gly Ser Gly Ser Gly Thr Glu
        210                 215                 220

Phe Thr Leu Thr Ile Ser Ser Leu Gln Pro Glu Asp Phe Ala Thr Tyr
225                 230                 235                 240

Tyr Cys Gln Gln His Asn Glu Tyr Pro Trp Thr Phe Gly Gly Gly Thr
                245                 250                 255

Lys Val Glu Ile Lys Arg Ala Ala Ala Gly Gly Gly Gly Ser Gly Gly
                260                 265                 270

Gly Gly Ser His His His His His His His
        275                 280
```

```
<210> SEQ ID NO 49
<211> LENGTH: 283
<212> TYPE: PRT
<213> ORGANISM: Artificial Sequence
<220> FEATURE:
<223> OTHER INFORMATION: VH4-VL1 scFv

<400> SEQUENCE: 49
```

```
Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Val Ser Gly Tyr Thr Phe
        35                  40                  45

Thr Asp His Thr Ile His Trp Met Arg Gln Ala Pro Gly Gln Gly Leu
        50                  55                  60

Glu Trp Met Gly Tyr Asn Tyr Pro Arg Glu Gly Ser Thr Lys Tyr Asn
65                  70                  75                  80

Glu Lys Phe Gln Gly Arg Val Thr Met Thr Ala Asp Lys Ser Thr Ser
                85                  90                  95

Thr Val Tyr Met Glu Leu Ser Ser Leu Arg Ser Glu Asp Thr Ala Val
                100                 105                 110

Tyr Tyr Cys Ala Lys Gly Phe Ile Thr Thr Val Val Pro Ser Ala Tyr
        115                 120                 125

Trp Gly Gln Gly Thr Leu Val Thr Val Ser Ser Gly Gly Gly Gly Ser
        130                 135                 140

Gly Gly Gly Gly Ser Gly Gly Gly Gly Ser Asp Ile Gln Leu Thr Gln
145                 150                 155                 160

Ser Pro Ser Phe Leu Ser Ala Ser Val Gly Asp Arg Val Thr Ile Thr
                165                 170                 175

Cys Arg Ala Ser Lys Ser Ile Ser Lys Tyr Leu Ala Trp Tyr Gln Gln
```

-continued

```
                    180               185               190
        Lys Pro Gly Lys Ala Pro Lys Leu Leu Ile Tyr Ser Gly Ser Thr Leu
                195               200               205

Gln Ser Gly Val Pro Ser Arg Phe Ser Gly Ser Gly Ser Gly Thr Glu
                210               215               220

Phe Thr Leu Thr Ile Ser Ser Leu Gln Pro Glu Asp Phe Ala Thr Tyr
        225               230               235               240

Tyr Cys Gln Gln His Asn Glu Tyr Pro Trp Thr Phe Gly Gly Gly Thr
                        245               250               255

Lys Val Glu Ile Lys Arg Ala Ala Ala Gly Gly Gly Gly Ser Gly Gly
                        260               265               270

Gly Gly Ser His His His His His His His His
                        275               280

<210> SEQ ID NO 50
<211> LENGTH: 283
<212> TYPE: PRT
<213> ORGANISM: Artificial Sequence
<220> FEATURE:
<223> OTHER INFORMATION: VH5-VL1 scFv

<400> SEQUENCE: 50

Met Glu Trp Ser Trp Val Phe Leu Phe Phe Leu Ser Val Thr Thr Gly
        1               5                 10                15

Val His Ser Gln Val Gln Leu Val Gln Ser Gly Ala Glu Val Lys Lys
                        20                25                30

Pro Gly Ala Ser Val Lys Val Ser Cys Lys Val Ser Gly Tyr Thr Phe
                        35                40                45

Thr Asp His Thr Ile His Trp Met Arg Gln Ala Pro Gly Gln Gly Leu
                50                55                60

Glu Trp Met Gly Tyr Asn Tyr Pro Arg Asp Val Ser Thr Lys Tyr Asn
        65                70                75                80

Glu Lys Phe Gln Gly Arg Val Thr Met Thr Ala Asp Lys Ser Thr Ser
                        85                90                95

Thr Val Tyr Met Glu Leu Ser Ser Leu Arg Ser Glu Asp Thr Ala Val
                        100               105               110

Tyr Tyr Cys Ala Lys Gly Phe Ile Thr Thr Val Val Pro Ser Ala Tyr
                        115               120               125

Trp Gly Gln Gly Thr Leu Val Thr Val Ser Ser Gly Gly Gly Gly Ser
                130               135               140

Gly Gly Gly Gly Ser Gly Gly Gly Gly Ser Asp Ile Gln Leu Thr Gln
        145               150               155               160

Ser Pro Ser Phe Leu Ser Ala Ser Val Gly Asp Arg Val Thr Ile Thr
                        165               170               175

Cys Arg Ala Ser Lys Ser Ile Ser Lys Tyr Leu Ala Trp Tyr Gln Gln
                        180               185               190

Lys Pro Gly Lys Ala Pro Lys Leu Leu Ile Tyr Ser Gly Ser Thr Leu
                195               200               205

Gln Ser Gly Val Pro Ser Arg Phe Ser Gly Ser Gly Ser Gly Thr Glu
                210               215               220

Phe Thr Leu Thr Ile Ser Ser Leu Gln Pro Glu Asp Phe Ala Thr Tyr
        225               230               235               240

Tyr Cys Gln Gln His Asn Glu Tyr Pro Trp Thr Phe Gly Gly Gly Thr
                        245               250               255

Lys Val Glu Ile Lys Arg Ala Ala Ala Gly Gly Gly Gly Ser Gly Gly
```

-continued

```
                  260             265             270
Gly Gly Ser His His His His His His His
        275             280

<210> SEQ ID NO 51
<211> LENGTH: 264
<212> TYPE: PRT
<213> ORGANISM: Artificial Sequence
<220> FEATURE:
<223> OTHER INFORMATION: VH2-VL1 scFv - no signal sequence

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp His
            20                  25                  30

Thr Ile His Trp Met Arg Gln Ala Pro Gly Gln Gly Leu Glu Trp Met
        35                  40                  45

Gly Tyr Asn Tyr Pro Arg Asp Gly Ser Thr Lys Tyr Asn Glu Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Leu Thr Gln Ser Pro Ser
    130                 135                 140

Phe Leu Ser Ala Ser Val Gly Asp Arg Val Thr Ile Thr Cys Arg Ala
145                 150                 155                 160

Ser Lys Ser Ile Ser Lys Tyr Leu Ala Trp Tyr Gln Gln Lys Pro Gly
            165                 170                 175

Lys Ala Pro Lys Leu Leu Ile Tyr Ser Gly Ser Thr Leu Gln Ser Gly
            180                 185                 190

Val Pro Ser Arg Phe Ser Gly Ser Gly Ser Gly Thr Glu Phe Thr Leu
        195                 200                 205

Thr Ile Ser Ser Leu Gln Pro Glu Asp Phe Ala Thr Tyr Tyr Cys Gln
    210                 215                 220

Gln His Asn Glu Tyr Pro Trp Thr Phe Gly Gly Gly Thr Lys Val Glu
225                 230                 235                 240

Ile Lys Arg Ala Ala Ala Gly Gly Gly Gly Ser Gly Gly Gly Gly Ser
            245                 250                 255

His His His His His His His His
            260

<210> SEQ ID NO 52
<211> LENGTH: 264
<212> TYPE: PRT
<213> ORGANISM: Artificial Sequence
<220> FEATURE:
<223> OTHER INFORMATION: VH4-VL1 scFv - no signal sequence

<400> SEQUENCE: 52

Gln Val Gln Leu Val Gln Ser Gly Ala Glu Val Lys Lys Pro Gly Ala
1               5                   10                  15
```

```
Ser Val Lys Val Ser Cys Lys Val Ser Gly Tyr Thr Phe Thr Asp His
            20                  25                  30

Thr Ile His Trp Met Arg Gln Ala Pro Gly Gln Gly Leu Glu Trp Met
        35                  40                  45

Gly Tyr Asn Tyr Pro Arg Glu Gly Ser Thr Lys Tyr Asn Glu Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Asp Ile Gln Leu Thr Gln Ser Pro Ser
    130                 135                 140

Phe Leu Ser Ala Ser Val Gly Asp Arg Val Thr Ile Thr Cys Arg Ala
145                 150                 155                 160

Ser Lys Ser Ile Ser Lys Tyr Leu Ala Trp Tyr Gln Gln Lys Pro Gly
            165                 170                 175

Lys Ala Pro Lys Leu Leu Ile Tyr Ser Gly Ser Thr Leu Gln Ser Gly
            180                 185                 190

Val Pro Ser Arg Phe Ser Gly Ser Gly Ser Gly Thr Glu Phe Thr Leu
            195                 200                 205

Thr Ile Ser Ser Leu Gln Pro Glu Asp Phe Ala Thr Tyr Tyr Cys Gln
    210                 215                 220

Gln His Asn Glu Tyr Pro Trp Thr Phe Gly Gly Gly Thr Lys Val Glu
225                 230                 235                 240

Ile Lys Arg Ala Ala Ala Gly Gly Gly Gly Ser Gly Gly Gly Gly Ser
            245                 250                 255

His His His His His His His His
            260
```

```
<210> SEQ ID NO 53
<211> LENGTH: 264
<212> TYPE: PRT
<213> ORGANISM: Artificial Sequence
<220> FEATURE:
<223> OTHER INFORMATION: VH5-VL1 scFv - no signal sequence

<400> SEQUENCE: 53

Gln Val Gln Leu Val Gln Ser Gly Ala Glu Val Lys Lys Pro Gly Ala
1                   5                   10                  15

Ser Val Lys Val Ser Cys Lys Val Ser Gly Tyr Thr Phe Thr Asp His
            20                  25                  30

Thr Ile His Trp Met Arg Gln Ala Pro Gly Gln Gly Leu Glu Trp Met
        35                  40                  45

Gly Tyr Asn Tyr Pro Arg Asp Val Ser Thr Lys Tyr Asn Glu Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110
```

-continued

```
Gly Thr Leu Val Thr Val Ser Ser Gly Gly Gly Ser Gly Gly Gly
        115                 120                 125

Gly Ser Gly Gly Gly Gly Ser Asp Ile Gln Leu Thr Gln Ser Pro Ser
        130                 135                 140

Phe Leu Ser Ala Ser Val Gly Asp Arg Val Thr Ile Thr Cys Arg Ala
145                 150                 155                 160

Ser Lys Ser Ile Ser Lys Tyr Leu Ala Trp Tyr Gln Gln Lys Pro Gly
                165                 170                 175

Lys Ala Pro Lys Leu Leu Ile Tyr Ser Gly Ser Thr Leu Gln Ser Gly
            180                 185                 190

Val Pro Ser Arg Phe Ser Gly Ser Gly Ser Gly Thr Glu Phe Thr Leu
            195                 200                 205

Thr Ile Ser Ser Leu Gln Pro Glu Asp Phe Ala Thr Tyr Tyr Cys Gln
        210                 215                 220

Gln His Asn Glu Tyr Pro Trp Thr Phe Gly Gly Gly Thr Lys Val Glu
225                 230                 235                 240

Ile Lys Arg Ala Ala Ala Gly Gly Gly Gly Ser Gly Gly Gly Gly Ser
                245                 250                 255

His His His His His His His His
                260
```

```
<210> SEQ ID NO 54
<211> LENGTH: 264
<212> TYPE: PRT
<213> ORGANISM: Artificial Sequence
<220> FEATURE:
<223> OTHER INFORMATION: VH1-VL1 scFv

<400> SEQUENCE: 54
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Thr Met His Trp Val Arg Gln Ala Pro Gly Gln Gly Leu Glu Trp Met
            35                  40                  45

Gly Tyr Asn Tyr Pro Arg Asp Gly Ser Thr Lys Tyr Ala Glu Lys Phe
        50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Leu Thr Gln Ser Pro Ser
        130                 135                 140

Phe Leu Ser Ala Ser Val Gly Asp Arg Val Thr Ile Thr Cys Arg Ala
145                 150                 155                 160

Ser Lys Ser Ile Ser Lys Tyr Leu Ala Trp Tyr Gln Gln Lys Pro Gly
                165                 170                 175

Lys Ala Pro Lys Leu Leu Ile Tyr Ser Gly Ser Thr Leu Gln Ser Gly
            180                 185                 190

Val Pro Ser Arg Phe Ser Gly Ser Gly Ser Gly Thr Glu Phe Thr Leu
            195                 200                 205
```

Thr Ile Ser Ser Leu Gln Pro Glu Asp Phe Ala Thr Tyr Tyr Cys Gln
    210                 215                 220

Gln His Asn Glu Tyr Pro Trp Thr Phe Gly Gly Gly Thr Lys Val Glu
225                 230                 235                 240

Ile Lys Arg Ala Ala Ala Gly Gly Gly Gly Ser Gly Gly Gly Gly Ser
                245                 250                 255

His His His His His His His His
            260

<210> SEQ ID NO 55
<211> LENGTH: 264
<212> TYPE: PRT
<213> ORGANISM: Artificial Sequence
<220> FEATURE:
<223> OTHER INFORMATION: VH1-VL2 scFv

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Thr Met His Trp Val Arg Gln Ala Pro Gly Gln Gly Leu Glu Trp Met
            35                  40                  45

Gly Tyr Asn Tyr Pro Arg Asp Gly Ser Thr Lys Tyr Ala Glu Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Asp Val Gln Ile Thr Gln Ser Pro Ser
    130                 135                 140

Phe Leu Ser Ala Ser Val Gly Asp Arg Val Thr Ile Thr Cys Arg Ala
145                 150                 155                 160

Ser Lys Ser Ile Ser Lys Tyr Leu Ala Trp Tyr Gln Gln Lys Pro Gly
                165                 170                 175

Lys Ala Asn Lys Leu Leu Ile Tyr Ser Gly Ser Thr Leu Gln Ser Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Glu Asp Phe Ala Thr Tyr Tyr Cys Gln
    210                 215                 220

Gln His Asn Glu Tyr Pro Trp Thr Phe Gly Gly Gly Thr Lys Val Glu
225                 230                 235                 240

Ile Lys Arg Ala Ala Ala Gly Gly Gly Gly Ser Gly Gly Gly Gly Ser
                245                 250                 255

His His His His His His His His
            260

<210> SEQ ID NO 56
<211> LENGTH: 264
<212> TYPE: PRT
<213> ORGANISM: Artificial Sequence
<220> FEATURE:

<223> OTHER INFORMATION: VH1-VL3 scFv

<400> SEQUENCE: 56

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Thr Met His Trp Val Arg Gln Ala Pro Gly Gln Gly Leu Glu Trp Met
        35                  40                  45

Gly Tyr Asn Tyr Pro Arg Asp Gly Ser Thr Lys Tyr Ala Glu Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Gln Leu Thr Gln Ser Pro Ser
    130                 135                 140

Ser Val Ser Ala Ser Val Gly Asp Arg Val Thr Ile Thr Cys Arg Ala
145                 150                 155                 160

Ser Lys Ser Ile Ser Lys Tyr Leu Ala Trp Tyr Gln Gln Lys Pro Gly
                165                 170                 175

Lys Ala Pro Lys Leu Leu Ile Tyr Ser Gly Ser Thr Leu Gln Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Asn Glu Tyr Pro Trp Thr Phe Gly Pro Gly Thr Lys Val Glu
225                 230                 235                 240

Ile Lys Arg Ala Ala Ala Gly Gly Gly Gly Ser Gly Gly Gly Gly Ser
            245                 250                 255

His His His His His His His His
            260
```

<210> SEQ ID NO 57
<211> LENGTH: 264
<212> TYPE: PRT
<213> ORGANISM: Artificial Sequence
<220> FEATURE:
<223> OTHER INFORMATION: VH2-VL2 scFv

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp His
            20                  25                  30

Thr Ile His Trp Met Arg Gln Ala Pro Gly Gln Gly Leu Glu Trp Met
        35                  40                  45

Gly Tyr Asn Tyr Pro Arg Asp Gly Ser Thr Lys Tyr Asn Glu Lys Phe
    50                  55                  60

Gln Gly Arg Val Thr Met Thr Ala Asp Lys Ser Thr Ser Thr Val Tyr
65                  70                  75                  80
```

Met Glu Leu Ser Ser Leu Arg Ser Glu Asp Thr Ala Val Tyr Tyr Cys
                85                    90                    95

Ala Lys Gly Phe Ile Thr Thr Val Val Pro Ser Ala Tyr Trp Gly Gln
            100                   105                   110

Gly Thr Leu Val Thr Val Ser Ser Gly Gly Gly Ser Gly Gly Gly
            115                   120                   125

Gly Ser Gly Gly Gly Gly Ser Asp Val Gln Ile Thr Gln Ser Pro Ser
        130                   135                   140

Phe Leu Ser Ala Ser Val Gly Asp Arg Val Thr Ile Thr Cys Arg Ala
145                   150                   155                   160

Ser Lys Ser Ile Ser Lys Tyr Leu Ala Trp Tyr Gln Gln Lys Pro Gly
                165                   170                   175

Lys Ala Asn Lys Leu Leu Ile Tyr Ser Gly Ser Thr Leu Gln Ser Gly
            180                   185                   190

Val Pro Ser Arg Phe Ser Gly Ser Gly Ser Gly Thr Asp Phe Thr Leu
            195                   200                   205

Thr Ile Ser Ser Leu Gln Pro Glu Asp Phe Ala Thr Tyr Tyr Cys Gln
        210                   215                   220

Gln His Asn Glu Tyr Pro Trp Thr Phe Gly Gly Gly Thr Lys Val Glu
225                   230                   235                   240

Ile Lys Arg Ala Ala Ala Gly Gly Gly Gly Ser Gly Gly Gly Gly Ser
            245                   250                   255

His His His His His His His His
            260

<210> SEQ ID NO 58
<211> LENGTH: 264
<212> TYPE: PRT
<213> ORGANISM: Artificial Sequence
<220> FEATURE:
<223> OTHER INFORMATION: VH2-VL3 scFv

<400> SEQUENCE: 58

Gln Val Gln Leu Val Gln Ser Gly Ala Glu Val Lys Lys Pro Gly Ala
1                 5                    10                    15

Ser Val Lys Val Ser Cys Lys Val Ser Gly Tyr Thr Phe Thr Asp His
                20                    25                    30

Thr Ile His Trp Met Arg Gln Ala Pro Gly Gln Gly Leu Glu Trp Met
            35                    40                    45

Gly Tyr Asn Tyr Pro Arg Asp Gly Ser Thr Lys Tyr Asn Glu Lys Phe
        50                    55                    60

Gln Gly Arg Val Thr Met Thr Ala Asp Lys Ser Thr Ser Thr Val Tyr
65                    70                    75                    80

Met Glu Leu Ser Ser Leu Arg Ser Glu Asp Thr Ala Val Tyr Tyr Cys
                85                    90                    95

Ala Lys Gly Phe Ile Thr Thr Val Val Pro Ser Ala Tyr Trp Gly Gln
            100                   105                   110

Gly Thr Leu Val Thr Val Ser Ser Gly Gly Gly Gly Ser Gly Gly Gly
            115                   120                   125

Gly Ser Gly Gly Gly Gly Ser Asp Val Gln Leu Thr Gln Ser Pro Ser
        130                   135                   140

Ser Val Ser Ala Ser Val Gly Asp Arg Val Thr Ile Thr Cys Arg Ala
145                   150                   155                   160

Ser Lys Ser Ile Ser Lys Tyr Leu Ala Trp Tyr Gln Gln Lys Pro Gly
                165                   170                   175

-continued

```
Lys Ala Pro Lys Leu Leu Ile Tyr Ser Gly Ser Thr Leu Gln Ser Gly
        180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
        210                 215                 220

Gln His Asn Glu Tyr Pro Trp Thr Phe Gly Pro Gly Thr Lys Val Glu
225                 230                 235                 240

Ile Lys Arg Ala Ala Ala Gly Gly Gly Gly Ser Gly Gly Gly Gly Ser
            245                 250                 255

His His His His His His His His
            260
```

```
<210> SEQ ID NO 59
<211> LENGTH: 264
<212> TYPE: PRT
<213> ORGANISM: Artificial Sequence
<220> FEATURE:
<223> OTHER INFORMATION: VH3-VL1 scFv

<400> SEQUENCE: 59

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
        20                  25                  30

Thr Ile His Trp Met Gln Gln Ala Pro Gly Lys Gly Leu Glu Trp Met
        35                  40                  45

Gly Tyr Asn Tyr Pro Arg Asp Gly Ser Thr Lys Tyr Asn Glu Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Leu Thr Gln Ser Pro Ser
        130                 135                 140

Phe Leu Ser Ala Ser Val Gly Asp Arg Val Thr Ile Thr Cys Arg Ala
145                 150                 155                 160

Ser Lys Ser Ile Ser Lys Tyr Leu Ala Trp Tyr Gln Gln Lys Pro Gly
            165                 170                 175

Lys Ala Pro Lys Leu Leu Ile Tyr Ser Gly Ser Thr Leu Gln Ser Gly
        180                 185                 190

Val Pro Ser Arg Phe Ser Gly Ser Gly Ser Gly Thr Glu Phe Thr Leu
        195                 200                 205

Thr Ile Ser Ser Leu Gln Pro Glu Asp Phe Ala Thr Tyr Tyr Cys Gln
        210                 215                 220

Gln His Asn Glu Tyr Pro Trp Thr Phe Gly Gly Gly Thr Lys Val Glu
225                 230                 235                 240

Ile Lys Arg Ala Ala Ala Gly Gly Gly Gly Ser Gly Gly Gly Gly Ser
            245                 250                 255

His His His His His His His His
            260
```

```
<210> SEQ ID NO 60
<211> LENGTH: 264
<212> TYPE: PRT
<213> ORGANISM: Artificial Sequence
<220> FEATURE:
<223> OTHER INFORMATION: VH3-VL2 scFv

<400> SEQUENCE: 60

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
            20                  25                  30

Thr Ile His Trp Met Gln Gln Ala Pro Gly Lys Gly Leu Glu Trp Met
        35                  40                  45

Gly Tyr Asn Tyr Pro Arg Asp Gly Ser Thr Lys Tyr Asn Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Phe Ile Thr Thr Val Val Pro Ser Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Gln Ile Thr Gln Ser Pro Ser
    130                 135                 140

Phe Leu Ser Ala Ser Val Gly Asp Arg Val Thr Ile Thr Cys Arg Ala
145                 150                 155                 160

Ser Lys Ser Ile Ser Lys Tyr Leu Ala Trp Tyr Gln Gln Lys Pro Gly
                165                 170                 175

Lys Ala Asn Lys Leu Leu Ile Tyr Ser Gly Ser Thr Leu Gln Ser Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Glu Asp Phe Ala Thr Tyr Tyr Cys Gln
    210                 215                 220

Gln His Asn Glu Tyr Pro Trp Thr Phe Gly Gly Gly Thr Lys Val Glu
225                 230                 235                 240

Ile Lys Arg Ala Ala Ala Gly Gly Gly Gly Ser Gly Gly Gly Gly Ser
            245                 250                 255

His His His His His His His His
            260

<210> SEQ ID NO 61
<211> LENGTH: 264
<212> TYPE: PRT
<213> ORGANISM: Artificial Sequence
<220> FEATURE:
<223> OTHER INFORMATION: VH3-VL3 scFv

<400> SEQUENCE: 61

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
            20                  25                  30

Thr Ile His Trp Met Gln Gln Ala Pro Gly Lys Gly Leu Glu Trp Met
```

```
            35                40                45
Gly Tyr Asn Tyr Pro Arg Asp Gly Ser Thr Lys Tyr Asn Glu Lys Phe
    50                55                60

Gln Gly Arg Val Thr Ile Thr Ala Asp Lys Ser Thr Ser Thr Ala Tyr
65                70                75                80

Met Glu Leu Ser Ser Leu Arg Ser Glu Asp Thr Ala Val Tyr Tyr Cys
                85                90                95

Ala Lys Gly Phe Ile Thr Thr Val Val Pro Ser Ala Tyr Trp Gly Gln
            100               105               110

Gly Thr Leu Val Thr Val Ser Ser Gly Gly Gly Gly Ser Gly Gly Gly
            115               120               125

Gly Ser Gly Gly Gly Gly Ser Asp Val Gln Leu Thr Gln Ser Pro Ser
    130               135               140

Ser Val Ser Ala Ser Val Gly Asp Arg Val Thr Ile Thr Cys Arg Ala
145               150               155               160

Ser Lys Ser Ile Ser Lys Tyr Leu Ala Trp Tyr Gln Gln Lys Pro Gly
                165               170               175

Lys Ala Pro Lys Leu Leu Ile Tyr Ser Gly Ser Thr Leu Gln Ser Gly
            180               185               190

Val Pro Ser Arg Phe Ser Gly Ser Gly Ser Gly Thr Asp Phe Thr Leu
            195               200               205

Thr Ile Ser Ser Leu Gln Pro Glu Asp Phe Ala Thr Tyr Tyr Cys Gln
    210               215               220

Gln His Asn Glu Tyr Pro Trp Thr Phe Gly Pro Gly Thr Lys Val Glu
225               230               235               240

Ile Lys Arg Ala Ala Ala Gly Gly Gly Ser Gly Gly Gly Gly Ser
            245               250               255

His His His His His His His His
            260

<210> SEQ ID NO 62
<211> LENGTH: 271
<212> TYPE: PRT
<213> ORGANISM: Artificial Sequence
<220> FEATURE:
<223> OTHER INFORMATION: Mouse 6B5 scFv

<400> SEQUENCE: 62

Met Lys Lys Thr Ala Ile Ala Ile Ala Val Ala Leu Ala Gly Phe Ala
1               5                 10                15

Thr Val Ala Gln Ala Gln Val Gln Leu Gln Gln Ser Asp Ala Glu Leu
            20                25                30

Val Lys Pro Gly Ala Ser Val Lys Ile Ser Cys Lys Val Ser Gly Tyr
            35                40                45

Thr Phe Thr Asp His Thr Ile His Trp Met Lys Gln Arg Pro Glu Gln
    50                55                60

Gly Leu Glu Trp Ile Gly Tyr Asn Tyr Pro Arg Asp Gly Ser Thr Lys
65                70                75                80

Tyr Asn Glu Lys Phe Lys Gly Lys Ala Thr Leu Thr Ala Asp Lys Ser
                85                90                95

Ser Ser Thr Ala Tyr Met Gln Leu Asn Ser Leu Thr Ser Glu Asp Ser
            100               105               110

Ala Val Tyr Phe Cys Ala Lys Gly Phe Ile Thr Thr Val Val Pro Ser
            115               120               125

Ala Tyr Trp Gly Gln Gly Thr Leu Val Thr Val Ser Ala Gly Gly Gly
```

-continued

```
          130                 135                 140

Gly Ser Gly Gly Gly Gly Ser Gly Gly Gly Gly Ser Asp Val Gln Ile
145                 150                 155                 160

Thr Gln Ser Pro Ser Tyr Leu Ala Ala Ser Pro Gly Glu Thr Ile Thr
                165                 170                 175

Ile Asn Cys Arg Ala Ser Lys Ser Ile Ser Lys Tyr Leu Ala Trp Tyr
                180                 185                 190

Gln Glu Lys Pro Gly Lys Thr Asn Lys Leu Leu Ile Tyr Ser Gly Ser
                195                 200                 205

Thr Leu Gln Ser Gly Ile Pro Ser Arg Phe Ser Gly Ser Gly Ser Gly
                210                 215                 220

Thr Asp Phe Thr Leu Thr Ile Ser Ser Leu Glu Pro Glu Asp Phe Ala
225                 230                 235                 240

Met Tyr Tyr Cys Gln Gln His Asn Glu Tyr Pro Trp Thr Phe Gly Gly
                245                 250                 255

Gly Thr Lys Leu Glu Ile Lys Gly Ser His His His His His His
                260                 265                 270
```

```
<210> SEQ ID NO 63
<211> LENGTH: 120
<212> TYPE: PRT
<213> ORGANISM: Artificial Sequence
<220> FEATURE:
<223> OTHER INFORMATION: Murine 6B5 VH parental

<400> SEQUENCE: 63

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
                20                  25                  30

Thr Ile His Trp Met Lys Gln Arg Pro Glu Gln Gly Leu Glu Trp Ile
            35                  40                  45

Gly Tyr Asn Tyr Pro Arg Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Lys Gly Phe Ile Thr Thr Val Val Pro Ser Ala Tyr Trp Gly Gln
                100                 105                 110

Gly Thr Leu Val Thr Val Ser Ala
        115                 120
```

```
<210> SEQ ID NO 64
<211> LENGTH: 107
<212> TYPE: PRT
<213> ORGANISM: Artificial Sequence
<220> FEATURE:
<223> OTHER INFORMATION: Murine 6B5 VL parental

<400> SEQUENCE: 64

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Thr Asn Lys Leu Leu Ile
        35                  40                  45
```

-continued

```
Tyr Ser Gly Ser Thr Leu Gln Ser Gly Ile Pro Ser Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Met Tyr Tyr Cys Gln Gln His Asn Glu Tyr Pro Trp
                85              90              95

Thr Phe Gly Gly Gly Thr Lys Leu Glu Ile Lys
            100             105
```

```
<210> SEQ ID NO 65
<211> LENGTH: 861
<212> TYPE: DNA
<213> ORGANISM: Artificial Sequence
<220> FEATURE:
<223> OTHER INFORMATION: VH3-VL3 scFv nucleic acid sequence

<400> SEQUENCE: 65
atgaagtacc ttcttcccac cgccgcggct gggttgttgt tacttgcagc acaaccggcg      60
atggctcaag tccagttagt tcagtcgggg gccgaagtaa agaagccagg tgctactgtg     120
aaaatttcgt gcaaagtgag cggatacaca ttcacggacc acacgattca ctggatgcag     180
caagctccgg gcaagggtct tgagtggatg ggctacaact atccgcgtga cggatcaaca     240
aaatacaatg aaaaatttca agggcgtgtt acaattaccg cggataaatc cacgagtact     300
gcctacatgg agttgtcctc acttcgttca gaggacacag cagtgtacta ttgtgctaaa     360
gggttcatca cgaccgtggt cccctctgct tattggggcc aaggaacact tgtgactgtg     420
tcttctgggg gcggggggag cggaggcgga ggtagcggtg gcgggggtag tgacgttcaa     480
ctgactcaat cgccttcatc cgttagcgcc agcgtaggcg accgtgtgac catcacgtgc     540
cgcgcgtcca aaagtatcag caagtacctg gcctggtacc aacaaaaacc cggaaaggca     600
ccgaagttgt tgatttattc cggttcaaca ttacaaagcg gcgttccgag tcgtttcagt     660
ggtagcggtt ccggcacaga ttttaccttg accatttcct ccctgcagcc agaagacttt     720
gctacttatt actgtcaaca gcacaatgag tacccgtgga cgtttgggcc tggaactaag     780
gttgagatta gcgtgctgc tgccggggc ggtggttccg gaggaggagg aagtcaccac     840
caccatcacc atcatcatgg t                                             861
```

```
<210> SEQ ID NO 66
<211> LENGTH: 861
<212> TYPE: DNA
<213> ORGANISM: Artificial Sequence
<220> FEATURE:
<223> OTHER INFORMATION: VH3-VL2 scFv nucleic acid sequence

<400> SEQUENCE: 66
atgaaatatc tgctgccaac tgcggcagca ggtctgttgc ttctggccgc tcaaccggcc      60
atggctcaag tccagttagt tcagagtggg gcagaggtta aaaaccggg agctacagta     120 aagatcagct gtaaagtatc aggttataca tttactgacc atactatcca ctggatgcaa     180
caggcgccag ggaaaggttt ggagtggatg ggatataatt atccacgcga cgggtcaact     240
aagtacaacg agaagtttca aggccgtgta acgattaccg cggacaaaag cacgagtaca     300
gcgtacatgg aattatcatc tttgcgctcg gaggacacag cggtctatta ctgtgccaag     360
ggtttcatca ctactgtggt accaagtgcg tattggggtc aaggaaccct tgttacggtg     420
tcatcagggg gtggcggaag tggcggtggt ggatcgggcg gaggtggaag cgatgttcag     480
atcacacagt cgccctcgtt cctgagtgca agtgtcggtg atcgtgtgac tattacgtgt     540
```

-continued

```
cgtgcatcga aatcaatctc aaagtatctg gcttggtacc agcaaaaacc tggaaaggct      600
aacaaattgt tgatctattc cgggagcacc cttcaaagcg gtgtccctc tcgtttctcc       660 ggatccgggt cagggaccga ctttactctg actatttcca gtcttcagcc ggaagatttt      720
gcgacttact attgccagca gcataatgag tacccatgac cttttggcgg tggcacaaag      780
gtcgagatta agcgtgcagc tgccggtggt ggaggttcgg gtggggcggg ttctcatcat      840
caccatcatc accatcatgg t                                               861
```

<210> SEQ ID NO 67
<211> LENGTH: 861
<212> TYPE: DNA
<213> ORGANISM: Artificial Sequence
<220> FEATURE:
<223> OTHER INFORMATION: VH3-VL1 scFv nucleic acid sequence

<400> SEQUENCE: 67

```
atgaaatatt tgcttccgac tgccgccgca ggtctgttac ttttagcagc gcagcccgct       60
atggcacagg tccagttagt tcaatcagga gcggaggtga agaagccggg agccacggtt      120
aaaatctcat gcaaggtgtc cggctataca tttaccgacc acacgattca ctggatgcag      180
caagctcccg ggaaggggct tgaatggatg gggtacaatt atccacgcga tggttccacc      240
aagtataacg aaaaatttca aggtcgtgtc accattaccg ctgacaaaag cacgtctaca      300
gcgtacatgg agctgagtag cttgcgctca gaggacacag ccgtatacta ttgcgcaaaa      360
ggtttcatca cgaccgtagt cccctctgcg tattggggac aggggaccct ggtcacggtc      420
tcctccgggg gcggaggatc gggaggcggg gggtctggag gtggtggatc tgacatccag      480
cttacccaat cgcctagctt cttgagtgct agtgtaggcg accgtgttac tatcacttgt      540
cgcgcttcta agagcattag caaatactta gcctggtacc aacaaaagcc gggaaaggca      600
cccaagctgt taatttatag tgggtctacc cttcagtccg gcgtaccctc acgcttttcc      660
ggcagtggct cgggtaccga atttaccctt acgatttctt cgcttcaacc cgaagatttt      720
gcaacgtact actgtcagca gcacaacgag tatccctgga cattcggcgg agggacaaaa      780
gtagaaatca agcgtgcagc cgcaggtggc ggcgggtctg gcggcggagg gagtcaccat      840
caccatcatc atcatcatgg a                                               861
```

<210> SEQ ID NO 68
<211> LENGTH: 861
<212> TYPE: DNA
<213> ORGANISM: Artificial Sequence
<220> FEATURE:
<223> OTHER INFORMATION: VH2-VL3 scFv nucleic acid sequence

<400> SEQUENCE: 68

```
atgaaatatt tgttacctac cgctgcggca ggacttctgc ttttggccgc tcagcccgca       60
atggctcaag tgcaattggt tcagtcaggg gccgaagtaa aaaagccagg cgcgagcgta      120
aaagtgagtt gcaaggtctc cggttacacg tttaccgatc acacgattca ctggatgcgt      180
caagctccag gccagggtct tgaatggatg gggtacaact atcctcgcga tggttcgacc      240
aagtataacg agaagtttca gggccgtgtc acaatgaccg ccgacaaatc aacgagcact      300
gtctacatgg agctgtcatc cctgcgcagc gaggatacag ctgtgtacta ctgtgccaag      360
ggcttcatta ctaccgtcgt ccccagcgcg tactggggtc aaggtacact ggtaacagtt      420
tcatccggag gaggggaag cggcggcggt ggatctggcg cggtgggtc agacgttcaa       480
```

```
cttacccagt cgccttcttc cgtgagtgcc tctgtcgggg atcgtgttac catcacttgc     540
cgcgcatcta agtcaatttc taaatatttg gcctggtatc agcagaaacc cggtaaagcg     600
cccaaattgt tgatctattc cggcagtacc ttgcaatccg gggtgccttc gcgcttctcg     660
gggagtggaa gcggcacgga tttcacttta acgatctcga gtttgcagcc ggaagatttt     720
gcgacttact attgtcagca gcataacgaa tatccatgga cctttggccc tggtacgaaa     780
gtagaaatca aacgtgcagc agccggtggg ggtggctccg gtggcggtgg gtcgcatcac     840
caccaccatc atcatcacgg t                                              861
```

```
<210> SEQ ID NO 69
<211> LENGTH: 861
<212> TYPE: DNA
<213> ORGANISM: Artificial Sequence
<220> FEATURE:
<223> OTHER INFORMATION: VH2-VL2 scFv nucleic acid sequence

<400> SEQUENCE: 69
atgaagtacc tgttgcccac agccgctgct gggttactgc ttcttgctgc ccagcccgca      60
atggcgcaag tgcaattagt ccagtctgga gcagaggtta aaaagccggg agcttcagtg     120
aaggtctcct gtaaggtaag tggttataca ttcaccgatc acacaatcca ttggatgcgc     180
caggccccag gtcagggtct tgaatggatg ggctataact acccgcgtga tggctcaact     240
aagtataacg agaagtttca ggggcgcgtt acaatgactg cggataaaag cacgtcgacg     300
gtgtacatgg aattgtcaag ccttcgttcc gaagataccg cagtttacta ttgtgctaag     360
ggctttatca ctaccgtggt acccagtgcg tactgggggc agggaaccct ggtaaccgtg     420
tcatcgggcg gaggcggaag cggggggaggt ggcagtggag gtggcgggtc tgacgttcaa     480
atcacccagt caccgtcatt tctttccgcg tctgtgggtg accgcgtaac aattacttgc     540
cgtgcttcga aaagcatttc gaaatacctt gcctggtacc aacagaaacc ggggaaagca     600
aacaaacttt taatctacag cgggagcacg cttcaatccg cgtcccatc ccgttttttct     660 ggctccggca gcgggaccga cttcacctta actatttctt cccttcaacc ggaggacttt     720
gcgacgtatt actgtcaaca acacaatgag tatccgtgga ctttcggagg cggaactaag     780
gttgaaatca gcgtgctgc tgctggcggg ggaggctcag gcggagggggg atcacatcat     840 catcaccatc atcatcacgg a                                              861
```

```
<210> SEQ ID NO 70
<211> LENGTH: 861
<212> TYPE: DNA
<213> ORGANISM: Artificial Sequence
<220> FEATURE:
<223> OTHER INFORMATION: VH2-VL1 scFv nucleic acid sequence

<400> SEQUENCE: 70
atgaaatact tgctgccgac tgccgcagcg ggattattat tacttgcggc tcagccggct      60
atggcgcagg tccagttagt tcagagtggg gcagaagtga agaaacccgg tgcatctgta     120
aaggtctcat gtaaagtatc tggctacacc ttcactgacc acactatcca ctggatgcgt     180
caagcaccag acaaaggttt agagtggatg ggatataact atccgcgtga cgggagtacg     240
aagtataacg aaaaatttca gggccgtgta accatgaccg cggataaatc cacttccact     300
gtctatatgg aattatcgtc gttacgtagc gaggacacgg cggtatatta ttgcgccaaa     360
gggtttatca cgactgttgt gccgtccgct tactgggggc aagggacttt agtgaccgtg     420
tccagcggag gggggggtag cggggtggc gggagtggtg gtggggggttc ggacattcag     480
```

-continued

```
cttacccaat cccctagctt tttgtcagcc tccgttggcg atcgtgtaac tattacgtgc      540
cgcgcctcca agtccatttc aaaatattta gcctggtacc aacagaagcc aggaaaagct      600
cctaaattac tgatttactc aggttccaca ttgcagtcgg gcgtaccaag ccgttttcg       660 ggaagtggta gcgggaccga gtttacattg acgattagta gtcttcaacc ggaggatttt      720
gcaacctact attgtcagca gcacaacgag tacccatgga cctttggagg cggtaccaaa      780
gtggaaatta aacgcgcagc agcaggcggc ggtggttcag ggggaggagg ctcgcatcac      840
caccatcatc atcaccacgg t                                                861
```

```
<210> SEQ ID NO 71
<211> LENGTH: 861
<212> TYPE: DNA
<213> ORGANISM: Artificial Sequence
<220> FEATURE:
<223> OTHER INFORMATION: VH1-VL3 scFv nucleic acid sequence

<400> SEQUENCE: 71
atgaaatacc ttttgccgac tgccgccgca ggattattgt tactggcggc tcagccggct       60
atggcccaag tccaattagt tcaatcaggg gcagaagtta agaagcccgg agcaagtgtc      120
aaggtctcat gcaaagcctc cggttacacc tttaccgacc acacgatgca ctgggttcgc      180
caagctcccg acagggcct ggaatggatg ggttataatt atccgcgtga tggtagcacg       240
aaatacgcgg aaaaattcca aggtcgcgtt acgatgaccg cggacaagtc tactagcacc      300
gtgtacatgg aacttagctc gctgcgttcg gaagatacgg cggtgtacta ctgtgcgaaa      360
ggtttcatca ctacagtagt gccaagtgcg tattggggtc aaggcacgct ggtaacggtt      420
tcaagtggtg gcggcggtag cggcggcggc ggcagcggag gaggggggatc ggatgtccaa     480 cttacgcaat ctccgtcctc tgtttccgca agtgtgggcg accgcgtaac catcacttgc      540
cgtgctagta aaagcatttc taagtattta gcgtggtatc aacagaagcc cggaaaggcg      600
ccaaagctgt tgatttattc cgggagtaca ttacaatctg gcgtgccgtc ccgcttctcc      660
ggcagcggta gtggtactga cttcacgctg acaattagtt cacttcagcc agaggatttt      720
gcgacatatt attgccagca gcataacgaa tacccatgga ccttcggtcc tggaaccaag      780
gttgaaatca aacgtgctgc ggccggcggc ggtgggagcg agggggcgg gtcacatcat       840 catcatcatc accatcatgg t                                                861
```

```
<210> SEQ ID NO 72
<211> LENGTH: 861
<212> TYPE: DNA
<213> ORGANISM: Artificial Sequence
<220> FEATURE:
<223> OTHER INFORMATION: VH1-VL2 scFv nucleic acid sequence

<400> SEQUENCE: 72
atgaaatacc ttcttcccac cgcagcagcg ggattgttat tattggctgc acaacctgcg       60
atggctcaag tacagttggt gcagtcaggg gcggaagtca agaaaccagg cgcttcagtg      120
aaagtttcgt gtaaagcatc cggctatact tttaccgacc acaccatgca ctgggttcgc      180
caagctcctg acagggtct ggaatggatg gggtacaact atccccgcga tggatccaca       240
aagtacgcgg agaagttcca aggacgtgta acaatgacgg ccgataaaag cacttccaca      300
gtctatatgg aactttcgtc tcttcgttct gaggacacag cagtttacta ctgtgctaaa      360
ggatttatca ctaccgtcgt tccgtctgca tattgggggc agggcacgtt agtaacagtc      420
```

-continued

```
agctccgggg gcgggggctc aggggggggt ggatcagggg gaggcggctc tgacgtgcag        480
atcactcagt cgcctagctt tctttcggct agtgtcgggg atcgcgtcac tatcacatgc        540
cgcgccagca aaagcatctc taaatacctg gcttggtacc aacaaaaacc cggaaaggct        600
aataagttgc tgatctacag tgggagtact ttgcagtcgg gggtgccgag tcgttttca         660 ggtagcgggt cgggcacgga ctttacccft acaatttcct ccctgcagcc cgaggacttt        720 gcccacatatt attgtcaaca gcacaacgag tacccgtgga cgtttggggg aggtaccaaa       780
gtggaaatca agcgtgcagc ggccgggggga ggtggaagcg gcggcggtgg aagtcaccat      840
catcaccacc accatcacgg a                                                  861

<210> SEQ ID NO 73
<211> LENGTH: 861
<212> TYPE: DNA
<213> ORGANISM: Artificial Sequence
<220> FEATURE:
<223> OTHER INFORMATION: VH1-VL1 scFv nucleic acid sequence

<400> SEQUENCE: 73
atgaaatacc tgttacctac tgctgccgca ggtttgttgc ttctggcggc tcaaccggcc        60
atggcacagg ttcagctggt gcaatcaggc gccgaagtca aaaaaccggg tgcaagcgtc        120
aaggtgagct gtaaggcaag cggatatact tttacagatc atacaatgca ctgggtacgc        180
caggcaccag gccagggcct tgaatggatg ggatataact acccacgtga tggatctact        240
aaatatgccg agaagttcca gggtcgcgtt accatgactg ctgataaaag tacatcaact        300
gtatacatgg aacttagctc attgcgttcc gaagatactg ccgtgtacta ttgtgcaaag        360
gggtttatca cgacagtcgt tccatcggca tattggggcc agggaacgtt agtaacagtc        420
agcagtgggg gtgggggggtc aggcggagga gggtctggtg ggggggggttc tgacatccag      480 ttgacacagt ccccatcctt tttgtctgca tcggttgggg accgcgtgac gattacttgt        540
cgcgcgtcca agtctatcag caaatattta gcatggtatc aacaaaaacc tggcaaggct        600
cccaagttac ttatttactc cggtagtact cttcagtcgg gagtgccttc ccgttttagc        660
gggtctggtt caggcacgga gtttaccctt acaattagtt ctctgcagcc cgaggatttt        720
gcaacttact actgccagca acacaatgag taccctgga cattcggcgg tgggacaaaa         780
gtcgagatta agcgtgccgc tgccggtgga ggagggtcag ggggtggcgg cagtcatcac       840
caccatcacc atcatcatgg a                                                  861

<210> SEQ ID NO 74
<211> LENGTH: 861
<212> TYPE: DNA
<213> ORGANISM: Artificial Sequence
<220> FEATURE:
<223> OTHER INFORMATION: 6B5 scFv nucleic acid sequence

<400> SEQUENCE: 74
atgaagtact tattgcccac tgctgctgct ggattattat tgttggcagc gcaaccggcc        60
atggcgcagg tccaacttca gcagtcagat gccgaacttg taaagccggg tgcaagcgtg        120
aaaatctcat gtaaagtatc tggttatacg tttacagatc acaccatcca ctggatgaag        180
caacgccctg agcagggttt agagtggatt ggctataatt atccgcgcga cggttcgaca        240
aaatacaacg aaaagttcaa gggcaaggca acgcttaccg ccgataagag ttcaagtaca        300
gcatatatgc aactgaacag cttaactagc gaagatagcg cagtttactt ttgcgcgaag        360
ggatttatca ccaccgtggt tccgagtgcc tactggggac agggcacatt ggttacagtc        420
```

-continued

```
agtgcaggag gaggagggtc cggtggcgga ggatcgggtg ggggtggatc agatgtccaa    480
atcacacaat cgccatccta cttggccgcc tcgcccggag aaaccatcac tattaattgc    540
cgcgcgagca agtctatttc caagtatttg gcatggtacc aagaaaagcc cggtaaaact    600
aacaaacttt tgatctactc tgggtccacg ctgcagtcag gaatcccatc ccgtttctcg    660
ggcagcggat ctgggacaga cttcacgttg acaatttcga gccttgagcc ggaagatttc    720
gcaatgtact actgtcagca acataacgag tacccttgga catttggcgg gggcacaaag    780
cttgaaatta aacgcgctgc tgccggagga ggtggttcgg ggggaggggg ttctcatcat    840
caccaccatc accaccacgg a                                             861
```

```
<210> SEQ ID NO 75
<211> LENGTH: 19
<212> TYPE: PRT
<213> ORGANISM: Artificial Sequence
<220> FEATURE:
<223> OTHER INFORMATION: Signal sequence

<400> SEQUENCE: 75

Met Glu Trp Ser Trp Val Phe Leu Phe Phe Leu Ser Val Thr Thr Gly
1               5                   10                  15

Val His Ser

<210> SEQ ID NO 76
<211> LENGTH: 22
<212> TYPE: PRT
<213> ORGANISM: Artificial Sequence
<220> FEATURE:
<223> OTHER INFORMATION: C-terminal tag

<400> SEQUENCE: 76

Arg Ala Ala Ala Gly Gly Gly Gly Ser Gly Gly Gly Gly Ser His His
1               5                   10                  15

His His His His His His
            20
```

ANTI-CERAMIDE ANTIBODIES

CROSS-REFERENCE TO RELATED APPLICATIONS

This application is a U.S. National Stage Application under 35 U.S.C. § 371 of International Application No. PCT/US2021/022914, which claims priority to U.S. Provisional Application No. 62/991,232, filed Mar. 18, 2020, the content of each of which is incorporated herein by reference in its entirety.

STATEMENT OF GOVERNMENT INTEREST

This invention was made with government support under R44AI106283 awarded by the National Institute of Health. The government has certain rights in the invention.

STATEMENT REGARDING SEQUENCE LISTING

The Sequence Listing associated with this application is provided in text format in lieu of a paper copy and is hereby incorporated by reference into the specification. A computer readable format copy of the Sequence Listing: filename: CERA-012_01WO_ST25.txt, date recorded: Mar. 17, 2021, file size 68.1 kilobytes.

FIELD

The present disclosure generally relates to anti-ceramide antibodies and methods of use thereof. In particular, the disclosure relates to humanized anti-ceramide antibodies inhibiting cell death. Such antibodies are useful for treating and preventing gastrointestinal syndrome, Graft versus Host Disease, and autoimmune disease.

BACKGROUND

Acute Radiation Syndrome (ARS) (sometimes known as radiation toxicity or radiation sickness) is an acute illness caused by irradiation of a large portion of the body by a high dose of penetrating radiation (e.g., high energy X-rays, gamma rays, and neutrons) in a very short period of time. Survival is extremely unlikely with this syndrome due to the destructive and irreparable changes in the GI tract and bone marrow caused by radiation-induced cell death.

Radiation is one of the most effective tools for the treatment of cancer. Unfortunately, an adverse side effect of radiation therapy is that healthy cells of the bone marrow, hair follicle, epidermis, and gastrointestinal tract are extremely sensitive to radiation-induced cell death. Other types of cancer strategies, such as bone marrow transplantation, evoke damaging immune responses in the host, resulting in rejection of the graft or graft-versus-host disease (GvHD).

Thus, there is an urgent need for alternative strategies to reduce the incidence of cell death associated with radiation GI syndrome and GvHD.

SUMMARY

The present disclosure provides compositions of anti-ceramide antibodies and antigen-binding fragments thereof. In some embodiments, the anti-ceramide antibodies and antigen-binding fragments thereof are humanized. In other embodiments, the anti-ceramide antibodies and antigen-binding fragments thereof are scFvs. In some embodiments, the disclosure further provides methods of preventing or inhibiting cell death in a subject in need thereof comprising administering the anti-ceramide antibodies or antigen-binding fragments to the subject. In some embodiments, the subject suffers from an autoimmune disease, GI syndrome, or GvHD.

In some embodiments, the present disclosure provides an anti-ceramide antibody or antigen-binding fragment thereof comprising an immunoglobulin heavy chain variable region (VH) comprising a heavy chain complementarity determining region (CDR) 1 (HCDR1), a heavy chain CDR2 (HCDR2), and a heavy chain CDR3 (HCDR3), and an immunoglobulin light chain variable region (VL) comprising a light chain complementarity determining region (CDR) 1 (LCDR1), a light chain CDR2 (LCDR2), and a light chain CDR3 (LCDR3), wherein: (a) the HCDR1 comprises an amino acid sequence selected from SEQ ID NO: 1 and 2; (b) the HCDR2 comprises an amino acid sequence selected from SEQ ID NO: 3, 4, 5, and 6; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises the amino acid sequence of SEQ ID NO: 10.

In some embodiments, the HCDR1 comprises SEQ ID NO: 1 and the HCDR2 comprises SEQ ID NO: 3. In some embodiments, the HCDR1 comprises SEQ ID NO: 1 and the HCDR2 comprises SEQ ID NO: 4. In some embodiments, the HCDR1 comprises SEQ ID NO: 1 and the HCDR2 comprises SEQ ID NO: 5. In some embodiments, the HCDR1 comprises SEQ ID NO: 1 and the HCDR2 comprises SEQ ID NO: 6. In some embodiments, the HCDR1 comprises SEQ ID NO: 2 and the HCDR2 comprises SEQ ID NO: 3. In some embodiments, the HCDR1 comprises SEQ ID NO: 2 and the HCDR2 comprises SEQ ID NO: 4. In some embodiments, the HCDR1 comprises SEQ ID NO: 2 and the HCDR2 comprises SEQ ID NO: 5. In some embodiments, the HCDR1 comprises SEQ ID NO: 2 and the HCDR2 comprises SEQ ID NO: 6.

In some embodiments, the VH comprises an amino acid sequence that is at least 90%, at least 95%, or at least 97% identical to SEQ ID NO: 17 and the VL comprises an amino acid sequence that is at least 90%, at least 95%, or at least 97% identical to SEQ ID NO: 22. In some embodiments, the VH comprises an amino acid sequence that is 100% identical to SEQ ID NO: 17 and the VL comprises an amino acid sequence that is 100% identical to SEQ ID NO: 22. In some embodiments, VH amino acid sequence consists of SEQ ID NO: 17 and the VL amino acid sequence consists of SEQ ID NO: 22.

In some embodiments, VH comprises an amino acid sequence that is at least 90%, at least 95%, or at least 97% identical to SEQ ID NO: 17 and the VL comprises an amino acid sequence that is at least 90%, at least 95%, or at least 97% identical to SEQ ID NO: 23. In some embodiments, the VH comprises an amino acid sequence that is 100% identical to SEQ ID NO: 17 and the VL comprises an amino acid sequence that is 100% identical to SEQ ID NO: 23. In some embodiments, the VH amino acid sequence consists of SEQ ID NO: 17 and the VL amino acid sequence consists of SEQ ID NO: 23.

In some embodiments, the VH comprises an amino acid sequence that is at least 90%, at least 95%, or at least 97% identical to SEQ ID NO: 17 and the VL comprises an amino acid sequence that is at least 90%, at least 95%, or at least 97% identical to SEQ ID NO: 24. In some embodiments, the VH comprises an amino acid sequence that is 100% identical to SEQ ID NO: 17 and the VL comprises an amino acid sequence that is 100% identical to SEQ ID NO: 24. In some embodiments, the VH amino acid sequence consists of SEQ ID NO: 17 and the VL amino acid sequence consists of SEQ ID NO: 24.

In some embodiments, the VH comprises an amino acid sequence that is at least 90%, at least 95%, or at least 97% identical to SEQ ID NO: 18 and the VL comprises an amino acid sequence that is at least 90%, at least 95%, or at least 97% identical to SEQ ID NO: 22. In some embodiments, the VH comprises an amino acid sequence that is 100% identical to SEQ ID NO: 18 and the VL comprises an amino acid sequence that is 100% identical to SEQ ID NO: 22. In some embodiments, the VH amino acid sequence consists of SEQ ID NO: 18 and the VL amino acid sequence consists of SEQ ID NO: 22.

In some embodiments, the VH comprises an amino acid sequence that is at least 90%, at least 95%, or at least 97% identical to SEQ ID NO: 18 and the VL comprises an amino acid sequence that is at least 90%, at least 95%, or at least 97% identical to SEQ ID NO: 23. In some embodiments, the VH comprises an amino acid sequence that is 100% identical to SEQ ID NO: 18 and the VL comprises an amino acid sequence that is 100% identical to SEQ ID NO: 23. In some embodiments, the VH amino acid sequence consists of SEQ ID NO: 18 and the VL amino acid sequence consists of SEQ ID NO: 23.

In some embodiments, the VH comprises an amino acid sequence that is at least 90%, at least 95%, or at least 97% identical to SEQ ID NO: 18 and the VL comprises an amino acid sequence that is at least 90%, at least 95%, or at least 97% identical to SEQ ID NO: 24. In some embodiments, the VH comprises an amino acid sequence that is 100% identical to SEQ ID NO: 18 and the VL comprises an amino acid sequence that is 100% identical to SEQ ID NO: 24. In some embodiments, the VH amino acid sequence consists of SEQ ID NO: 18 and the VL amino acid sequence consists of SEQ ID NO: 24.

In some embodiments, the VH comprises an amino acid sequence that is at least 90%, at least 95%, or at least 97% identical to SEQ ID NO: 19 and the VL comprises an amino acid sequence that is at least 90%, at least 95%, or at least 97% identical to SEQ ID NO: 22. In some embodiments, the VH comprises an amino acid sequence that is 100% identical to SEQ ID NO: 19 and the VL comprises an amino acid sequence that is 100% identical to SEQ ID NO: 22. In some embodiments, the VH amino acid sequence consists of SEQ ID NO: 19 and the VL amino acid sequence consists of SEQ ID NO: 22.

In some embodiments, the VH comprises an amino acid sequence that is at least 90%, at least 95%, or at least 97% identical to SEQ ID NO: 19 and the VL comprises an amino acid sequence that is at least 90%, at least 95%, or at least 97% identical to SEQ ID NO: 23. In some embodiments, the VH comprises an amino acid sequence that is 100% identical to SEQ ID NO: 19 and the VL comprises an amino acid sequence that is 100% identical to SEQ ID NO: 23. In some embodiments, the VH amino acid sequence consists of SEQ ID NO: 19 and the VL amino acid sequence consists of SEQ ID NO: 23.

In some embodiments, the VH comprises an amino acid sequence that is at least 90%, at least 95%, or at least 97% identical to SEQ ID NO: 19 and the VL comprises an amino acid sequence that is at least 90%, at least 95%, or at least 97% identical to SEQ ID NO: 24. In some embodiments, the VH comprises an amino acid sequence that is 100% identical to SEQ ID NO: 19 and the VL comprises an amino acid sequence that is 100% identical to SEQ ID NO: 24. In some embodiments, the VH amino acid sequence consists of SEQ ID NO: 19 and the VL amino acid sequence consists of SEQ ID NO: 24.

In some embodiments, the VH comprises an amino acid sequence that is at least 90%, at least 95%, or at least 97% identical to SEQ ID NO: 20 and the VL comprises an amino acid sequence that is at least 90%, at least 95%, or at least 97% identical to SEQ ID NO: 22. In some embodiments, the VH comprises an amino acid sequence that is 100% identical to SEQ ID NO: 20 and the VL comprises an amino acid sequence that is 100% identical to SEQ ID NO: 22. In some embodiments, the VH amino acid sequence consists of SEQ ID NO: 20 and the VL amino acid sequence consists of SEQ ID NO: 22.

In some embodiments, the VH comprises an amino acid sequence that is at least 90%, at least 95%, or at least 97% identical to SEQ ID NO: 21 and the VL comprises an amino acid sequence that is at least 90%, at least 95%, or at least 97% identical to SEQ ID NO: 22. In some embodiments, the VH comprises an amino acid sequence that is 100% identical to SEQ ID NO: 21 and the VL comprises an amino acid sequence that is 100% identical to SEQ ID NO: 22. In some embodiments, the VH amino acid sequence consists of SEQ ID NO: 21 and the VL amino acid sequence consists of SEQ ID NO: 22.

In some embodiments, the present disclosure provides an anti-ceramide antibody or antigen-binding fragment thereof comprising an immunoglobulin heavy chain variable region (VH) and an immunoglobulin light chain variable region (VL), wherein the VH comprises an amino acid sequence that is at least 90%, 95%, or 97% identical to a sequence selected from SEQ ID NO: 17, 18, 19, 20, and 21; and wherein the VL comprises an amino acid sequence that is at least 90%, 95%, or 97% identical to a sequence selected from SEQ ID NO: 22, 23 and 24.

In some embodiments, the VH comprises an amino acid sequence that is at least 90%, 95%, or 97% identical to SEQ ID NO: 17 and the VL comprises an amino acid sequence that is at least 90%, 95%, or 97% identical to SEQ ID NO: 22. In some embodiments, the VH comprises an amino acid sequence that is 100% identical to SEQ ID NO: 17 and the VL comprises an amino acid sequence that is 100% identical to SEQ ID NO: 22. In some embodiments, the VH amino acid sequence consists of SEQ ID NO: 17 and the VL amino acid sequence consists of SEQ ID NO: 22.

In some embodiments, the VH comprises an amino acid sequence that is at least 90%, 95%, or 97% identical to SEQ ID NO: 17 and the VL comprises an amino acid sequence that is at least 90%, 95%, or 97% identical to SEQ ID NO: 23. In some embodiments, the VH comprises an amino acid sequence that is 100% identical to SEQ ID NO: 17 and the VL comprises an amino acid sequence that is 100% identical to SEQ ID NO: 23. In some embodiments, the VH amino acid sequence consists of SEQ ID NO: 17 and the VL amino acid sequence consists of SEQ ID NO: 23.

In some embodiments, the VH comprises an amino acid sequence that is at least 90%, 95%, or 97% identical to SEQ ID NO: 17 and the VL comprises an amino acid sequence that is at least 90%, 95%, or 97% identical to SEQ ID NO: 24. In some embodiments, the VH comprises an amino acid sequence that is 100% identical to SEQ ID NO: 17 and the VL comprises an amino acid sequence that is 100% identical to SEQ ID NO: 24. In some embodiments, the VH amino acid sequence consists of SEQ ID NO: 17 and the VL amino acid sequence consists of SEQ ID NO: 24.

In some embodiments, the VH comprises an amino acid sequence that is at least 90%, 95%, or 97% identical to SEQ ID NO: 18 and the VL comprises an amino acid sequence that is at least 90%, 95%, or 97% identical to SEQ ID NO: 22. In some embodiments, the VH comprises an amino acid sequence that is 100% identical to SEQ ID NO: 18 and the VL comprises an amino acid sequence that is 100% identical to SEQ ID NO: 22. In some embodiments, the VH amino acid sequence consists of SEQ ID NO: 18 and the VL amino acid sequence consists of SEQ ID NO: 22.

In some embodiments, the VH comprises an amino acid sequence that is at least 90%, 95%, or 97% identical to SEQ ID NO: 18 and the VL comprises an amino acid sequence that is at least 90%, 95%, or 97% identical to SEQ ID NO: 23. In some embodiments, the VH comprises an amino acid sequence that is 100% identical to SEQ ID NO: 18 and the VL comprises an amino acid sequence that is 100% identical to SEQ ID NO: 23. In some embodiments, the VH amino acid sequence consists of SEQ ID NO: 18 and the VL amino acid sequence consists of SEQ ID NO: 23.

In some embodiments, the VH comprises an amino acid sequence that is at least 90%, 95%, or 97% identical to SEQ ID NO: 18 and the VL comprises an amino acid sequence that is at least 90%, 95%, or 97% identical to SEQ ID NO: 24. In some embodiments, the VH comprises an amino acid sequence that is 100% identical to SEQ ID NO: 18 and the VL comprises an amino acid sequence that is 100% identical to SEQ ID NO: 24. In some embodiments, the VH amino acid sequence consists of SEQ ID NO: 18 and the VL amino acid sequence consists of SEQ ID NO: 24.

In some embodiments, the VH comprises an amino acid sequence that is at least 90%, 95%, or 97% identical to SEQ ID NO: 19 and the VL comprises an amino acid sequence that is at least 90%, 95%, or 97% identical to SEQ ID NO: 22. In some embodiments, the VH comprises an amino acid sequence that is 100% identical to SEQ ID NO: 19 and the VL comprises an amino acid sequence that is 100% identical to SEQ ID NO: 22. In some embodiments, the VH amino acid sequence consists of SEQ ID NO: 19 and the VL amino acid sequence consists of SEQ ID NO: 22.

In some embodiments, the VH comprises an amino acid sequence that is at least 90%, 95%, or 97% identical to SEQ ID NO: 19 and the VL comprises an amino acid sequence that is at least 90%, 95%, or 97% identical to SEQ ID NO: 23. In some embodiments, the VH comprises an amino acid sequence that is 100% identical to SEQ ID NO: 19 and the VL comprises an amino acid sequence that is 100% identical to SEQ ID NO: 23. In some embodiments, the VH amino acid sequence consists of SEQ ID NO: 19 and the VL amino acid sequence consists of SEQ ID NO: 23.

In some embodiments, VH comprises an amino acid sequence that is at least 90%, 95%, or 97% identical to SEQ ID NO: 19 and the VL comprises an amino acid sequence that is at least 90%, 95%, or 97% identical to SEQ ID NO: 24. In some embodiments, the VH comprises an amino acid sequence that is 100% identical to SEQ ID NO: 19 and the VL comprises an amino acid sequence that is 100% identical to SEQ ID NO: 24. In some embodiments, the VH amino acid sequence consists of SEQ ID NO: 19 and the VL amino acid sequence consists of SEQ ID NO: 24.

In some embodiments, the VH comprises an amino acid sequence that is at least 90%, 95%, or 97% identical to SEQ ID NO: 20 and the VL comprises an amino acid sequence that is at least 90%, 95%, or 97% identical to SEQ ID NO: 22. In some embodiments, the VH comprises an amino acid sequence that is 100% identical to SEQ ID NO: 20 and the VL comprises an amino acid sequence that is 100% identical to SEQ ID NO: 22. In some embodiments, the VH amino acid sequence consists of SEQ ID NO: 20 and the VL amino acid sequence consists of SEQ ID NO: 22.

In some embodiments, the VH comprises an amino acid sequence that is at least 90%, 95%, or 97% identical to SEQ ID NO: 21 and the VL comprises an amino acid sequence that is at least 90%, 95%, or 97% identical to SEQ ID NO: 22. In some embodiments, the VH comprises an amino acid sequence that is 100% identical to SEQ ID NO: 21 and the VL comprises an amino acid sequence that is 100% identical to SEQ ID NO: 22. In some embodiments, the VH amino acid sequence consists of SEQ ID NO: 21 and the VL amino acid sequence consists of SEQ ID NO: 22.

In some embodiments, the antibody or antigen-binding fragment is humanized. In some embodiments, the antibody or antigen-binding fragment is fully human. In some embodiments, the anti-ceramide antibody comprises one or more point mutations in the Fc domain of the antibody.

In some embodiments, the antigen-binding fragment is a single chain variable fragment (scFv). In some embodiments, the scFv comprises an amino acid sequence that is at least 90%, at least 95%, or at least 97% identical to a sequence selected from the group consisting of SEQ ID NOs: 48-61. In some embodiments, the scFv comprises an amino acid sequence that is 100% identical to a sequence selected from the group consisting of SEQ ID NOs: 48-61. In some embodiments, the scFv consists of a sequence selected from the group consisting of SEQ ID NOs: 48-61.

In some embodiments, the light chain variable region of said scFv is carboxy-terminal to the heavy chain variable region of said scFv. In some embodiments, the light chain variable region of said scFv is amino-terminal to the heavy chain variable region of said scFv.

In some embodiments, the scFv comprises a linker polypeptide. In some embodiments, the linker polypeptide is between the light chain variable region and the heavy chain variable region of the said scFv. In some embodiments, the linker polypeptide comprises a Gly4Ser linker. In some embodiments, the linker polypeptide comprises the formula (Gly4Ser)n, wherein n=1-5.

In some embodiments, the present disclosure provides an anti-ceramide single chain variable fragment (scFv) comprising an amino acid sequence that is at least 80%, at least 85%, at least 90%, at least 95%, or at least 97% identical to a sequence selected from the group consisting of SEQ ID NOs: 48-61. In some embodiments, the scFv comprises an amino acid sequence that is 100% identical to a sequence selected from the group consisting of SEQ ID NOs: 48-61. In some embodiments, the scFv consists of an amino acid sequence selected from the group consisting of SEQ ID NOs: 48-61.

In some embodiments, the present disclosure provides a polynucleotide encoding the anti-ceramide antibody or anti-gen-binding fragment thereof described herein.

In some embodiments, the present disclosure provides an anti-ceramide single chain variable fragment (scFv) comprising an amino acid sequence that is at least 80%, at least 85%, at least 90%, at least 95%, or at least 97% identical to SEQ ID NO: 48 or 51. In some embodiments, the scFv comprises an amino acid sequence that is 100% identical to SEQ ID NO: 48 or 51. In some embodiments, the scFv consists of the amino acid sequence of SEQ ID NO: 48 or 51.

In some embodiments, the present disclosure provides a polynucleotide encoding the anti-ceramide single chain vari-able fragments (scFvs) described herein. In some embodiments, the present disclosure provides an expression vector comprising said polynucleotide.

In some embodiments, the present disclosure provides a host cell comprising a polynucleotide or expression vector described herein.

In some embodiments, the present disclosure provides a method of manufacturing an anti-ceramide antibody or antigen-binding fragment thereof described herein or an anti-ceramide single chain variable fragment (scFv) described herein, comprising introducing the expression vector of Embodiment 98 into a host cell.

In some embodiments, the present disclosure provides a method of inhibiting apoptosis in a subject in need thereof, comprising administering to the subject a therapeutically effective amount of an anti-ceramide antibody or antigen-binding fragment thereof described herein or an anti-ceramide single chain variable fragment (scFv) described herein. In some embodiments, the apoptosis is associated with a disease selected from the group consisting of graft versus host disease, radiation disease, GI syndrome, and autoimmune disease. In some embodiments, the disease is radiation disease or GI syndrome and the anti-ceramide antibody or antigen-binding fragment thereof is administered before the subject is exposed to radiation. In some embodiments, the disease is graft versus host disease and the anti-ceramide antibody or antigen-binding fragment thereof is administered before the subject receives a transplant. In some embodiments, the transplant is a bone marrow transplant.

In some embodiments, the anti-ceramide antibody or antigen-binding fragment thereof is administered intravenously, intramuscularly, intraperitoneally, intracerobrospinally, subcutaneously, intrasynovially, intrathecally, orally, topically, or via inhalation.

In some embodiments, the present disclosure provides a method for mitigating apoptosis in a subject with GI syndrome comprising administering to the subject an effective amount of the anti-ceramide antibody or antigen-binding fragment thereof of any one of Embodiments 1-89 or the anti-ceramide scFv of any one of Embodiments 94-96, after the subject is exposed to penetrating radiation. In some embodiments, the anti-ceramide antibody or antigen-binding fragment thereof is administered immediately after the subject is exposed to penetrating radiation. In some embodiments, the anti-ceramide antibody or antigen-binding fragment thereof is administered within 24 hours after the subject is exposed to penetrating radiation.

In some embodiments, the present disclosure provides a method for inhibiting apoptosis in a subject with GvHD comprising administering to the subject an effective amount of anti-ceramide antibody or antigen binding fragment thereof of any one of Embodiments 1-89 or the anti-ceramide scFv of any one of Embodiments 94-96, either before the subject receives a transplant or after the subject receives a transplant prior to the onset of GvHD. In some embodiments, the transplant is a bone marrow transplant.

BRIEF DESCRIPTION OF THE DRAWINGS

The accompanying drawings illustrate one or more embodiments of the present disclosure and, together with the written description, serve to explain the principles of exemplary embodiments of the present disclosure.

FIG. 4A shows the amino acid sequence alignments of the humanized VH regions. The CDRs are underlined. CDR amino acids that differ from the parental murine CDR sequence are shown in bold. Framework region amino acids that differ from the human germline framework sequence are shown in bold.

FIG. 4B shows the amino acid sequence alignments of the humanized VL regions. The CDRs are underlined.

DETAILED DESCRIPTION

Figure 1:
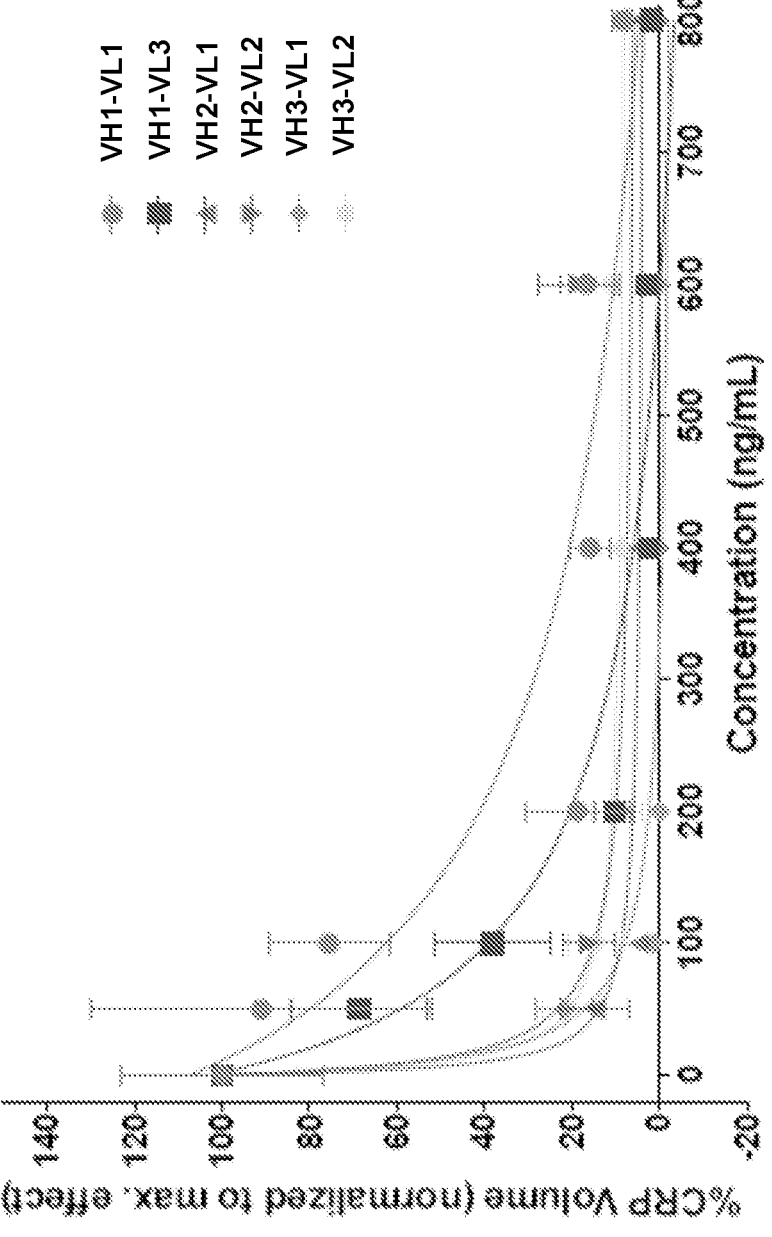
FIG. 1 shows a dose-response curve of CD28-induced ceramide-rich platform formation (CRP) in T cells with increasing concentrations of 6B5 scFvs.

The details of the disclosure are set forth in the accompanying description below. Although methods and materials similar or equivalent to those described herein can be used in the practice or testing of the present disclosure, illustrative methods, and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The term "antibody" refers to an immunoglobulin (Ig) molecule capable of binding to a specific target, such as a carbohydrate, polynucleotide, lipid, or polypeptide, through at least one epitope recognition site located in the variable region of the Ig molecule. As used herein, the term encompasses intact polyclonal or monoclonal antibodies and antigen-binding fragments thereof. For example, a native immunoglobulin molecule is comprised of two heavy chain polypeptides and two light chain polypeptides. Each of the heavy chain polypeptides associate with a light chain polypeptide by virtue of interchain disulfide bonds between the heavy and light chain polypeptides to form two heterodimeric proteins or polypeptides (i.e., a protein comprised of two heterologous polypeptide chains). The two heterodimeric proteins then associate by virtue of additional interchain disulfide bonds between the heavy chain polypeptides to form an immunoglobulin protein or polypeptide.

The term "antigen-binding fragment" as used herein refers to a polypeptide fragment that contains at least one Complementarity-determining region (CDR) of an immunoglobulin heavy and/or light chain that binds to at least one epitope of the antigen of interest. In this regard, an antigen-binding fragment of the herein described antibodies may comprise 1, 2, 3, 4, 5, or all 6 CDRs of a variable heavy chain (VH) and variable light chain (VL) sequence from antibodies that specifically bind ceramide. Antigen-binding fragments include proteins that comprise a portion of a full length antibody, generally the antigen binding or variable region thereof, such as Fab, F(ab')2, Fab', Fv fragments, minibodies, diabodies, single domain antibody (dAb), single-chain variable fragments (scFv), multispecific antibodies formed from antibody fragments, and any other modified configuration of the immunoglobulin molecule that comprises an antigen-binding site or fragment of the required specificity. In certain embodiments of the disclosure, an antigen-binding fragment, rather than an intact antibody, is used to increase tissue penetration or tumor penetration. In other embodiments, antigen-binding fragments are further modified to increase serum half-life.

The term "F(ab)" refers to two of the protein fragments resulting from proteolytic cleavage of IgG molecules by the enzyme papain. Each F(ab) comprises a covalent heterodimer of the VH chain and VL chain and includes an intact antigen-binding site. Each F(ab) is a monovalent antigen-binding fragment. The term "Fab'" refers to a fragment derived from F(ab')2 and may contain a small portion of Fc. Each Fab' fragment is a monovalent antigen-binding fragment.

The term "F(ab')2" refers to a protein fragment of IgG generated by proteolytic cleavage by the enzyme pepsin. Each F(ab')2 fragment comprises two F(ab') fragments and is therefore a bivalent antigen-binding fragment.

An "Fv fragment" refers to a non-covalent VH::VL heterodimer which includes an antigen-binding site that retains much of the antigen recognition and binding capabilities of the native antibody molecule, but lacks the CH1 and CL domains contained within a Fab. Inbar et al. (1972) Proc. Nat. Acad. Sci. USA 69:2659-2662; Hochman et al. (1976) Biochem 15:2706-2710; and Ehrlich et al. (1980) Biochem 19:4091-4096. In some embodiments, the Fv fragment can be produced by preferential proteolytic cleavage of an IgM, and on rare occasions of an IgG or IgA immunoglobulin molecule. Fv fragments are, however, more commonly derived using recombinant techniques known in the art.

Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "diabody" refers to a bispecific antibody in which VH and VL domains are expressed in a single polypeptide chain using a linker that is too short to allow for pairing between the two domains on the same chain, thereby forcing the domains to pair with complementary domains of another chain and creating two antigen-binding sites (see, e.g., Holliger et al., Proc. Natl. Acad. Sci. USA 90:6444-48 (1993) and Poljak et al., Structure 2:1121-23 (1994)).

The term "nanobody" or a "single domain antibody" refers to an antigen-binding fragment consisting of a single monomeric variable antibody domain. The Nanoclone method is a method for generating Nanobodies against a desired target based on automated high-throughput selection of B-cells. (See, WO 2006/079372)

The term "monoclonal antibody" as used herein refers to an antibody obtained from a population of substantially homogeneous antibodies, i.e., the individual antibodies comprising the population are identical except for possible naturally occurring mutations that may be present in minor amounts.

In some embodiments, the term "chimeric antibody" as used herein refers to a monoclonal antibody in which a portion of the heavy and/or light chain is identical or homologous to corresponding sequences in antibodies derived from a particular species or belonging to a particular antibody class or subclass, while the remainder of the chain(s) is identical or homologous to corresponding sequences in antibodies derived from another species or belonging to another antibody class or subclass, as well as fragments of such antibodies, so long as they exhibit the desired biological activity.

The term "single chain variable fragment" or "scFv" refers to a fusion protein of the variable regions of the heavy (VH) and light chains (VL) of immunoglobulins, connected with a short linker peptide of ten to about 25 amino acids. Huston et al. (1988) *Proc. Nat. Acad. Sci. USA* 85(16):5879-5883. The linker can connect the N-terminus of the VH with the C-terminus of the VL, or vice versa. A number of methods have been described to discern chemical structures for converting the naturally aggregated—but chemically separated—light and heavy polypeptide chains from an antibody V region into an scFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

The term "antigen" refers to a molecule or a portion of a molecule capable of being bound by an antibody or an antigen-binding fragment thereof and additionally capable of being used in an animal to produce antibodies capable of binding to an epitope of that antigen. An antigen may have one or more epitopes. Embodiments herein contemplate the use of ceramide, or ceramide conjugated to a hapten, as an antigen.

The term "epitope" refers to a region of an antigen that is bound by an antibody. Epitope determinants can include chemically active surface groupings of molecules such as amino acids, sugar side chains, phosphoryl, or sulfonyl and may have specific three-dimensional structural characteristics, and/or specific charge characteristics.

Herein, the term "specifically binds" refers to the ability of an antibody or antigen-binding fragment thereof to bind a target antigen with a binding affinity (Ka) of at least $10^5$ $M^{-1}$ while not significantly binding other components or antigens present in a mixture. Reference to an anti-ceramide antibody herein refers to an antibody or antigen-binding fragment thereof that specifically binds to ceramide.

Binding affinity (Ka) refers to an equilibrium association of a particular interaction expressed in the units of 1/M or $M^{-1}$. Antibodies or antigen-binding fragments thereof can be classified as "high affinity" antibodies or antigen-binding fragments thereof and "low affinity" antibodies or antigen-binding fragments thereof. "High affinity" antibodies or antigen-binding fragments thereof refer to those antibodies or antigen-binding fragments thereof with a Ka of at least $10^7 M^{-1}$, at least $10^8 M^{-1}$, at least $10^9 M^{-1}$, at least $10^{10} M^{-1}$, at least $10^{11} M^{-1}$, at least $10^{12} M^{-1}$, or at least $10^{13} M^{-1}$. "Low affinity" antibodies or antigen-binding fragments thereof refer to those antibodies or antigen-binding fragments thereof with a Ka of up to $10^7 M^{-1}$, up to $10^6 M^{-1}$, up to $10^5 M^{-1}$. Alternatively, affinity can be defined as an equilibrium dissociation constant (Kd) of a particular binding interaction with units of M (e.g., $10^{-5}$ M to $10^{-13}$, or about 500 nM, about 300 nM, about 250 nM, about 200 nM, about 150 nM, about 100 nM, about 50 nM, about 25 nM, about 10 nM, or about 5 nM). Affinities of binding domain polypeptides and single chain polypeptides according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

A "conservative substitution" is recognized in the art as a substitution of one amino acid for another amino acid that has similar properties. Exemplary conservative substitutions are well-known in the art (see, e.g., PCT Application Publication No. WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, MA (1990), p. 8).

As used herein, the term "derivative" refers to a modification of one or more amino acid residues of a peptide by chemical or biological means, either with or without an enzyme, e.g., by glycosylation, alkylation, acylation, ester formation, or amide formation.

As used herein, a polypeptide or polynucleotide from which another polypeptide or polynucleotide is derived from is referred to as the "parental" or "reference" polynucleotide or polypeptide. For example, a humanized antibody can be derived from a parental murine antibody.

The term "variant" or "variants" as used herein refers to a polynucleotide or polypeptide with a sequence differing from that of a reference polynucleotide or polypeptide, but retaining essential properties of the parental polynucleotide or polypeptide. Generally, variant polynucleotide or polypeptide sequences are overall closely similar, and, in many regions, identical to the parental polynucleotide or polypeptide. For instance, a variant polynucleotide or polypeptide may exhibit at least about 70%, at least about 80%, at least about 90%, at least about 91%, at least about 92%, at least about 93%, at least about 94%, at least about 95%, at least about 96%, at least about 97%, at least about 98% at least about 99%, or at least about 99.5% sequence identity compared to the parental polynucleotide or polypeptide.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage sequence identity is calculated by determining the number of positions at which the identical nucleic acid base or amino acid residue occurs in both sequences to yield the number of identical positions. The number of identical positions is then divided by the total number of positions in the comparison window and multiplied by 100 to yield the percentage of sequence identity. Percentage of sequence identity is determined by comparing two optimally aligned sequences over a comparison window. The comparison window for polynucleotide sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

The term "substantially identical" refers to a polypeptide sequence that contains a sufficient number of identical amino acids to a second polypeptide sequence such that the first and second polypeptide sequence have similar activity. Polypeptides that are substantially identical are at least about 80%, at least about 85%, at least about 90%, at least about 95%, at least about 96%, at least about 97%, at least about 98%, at least about 99%, or at least about 100% identical in amino acid sequence.

"Fc region" or "Fc domain" refers to a polypeptide sequence corresponding to or derived from the portion of an antibody that is capable of binding to Fc receptors on cells and/or the C1q component of complement, thereby mediating the effector function of an antibody. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc region is a homodimeric protein comprising two polypeptides that are associated by disulfide bonds, and each comprising a hinge region, a CH2 domain, and a CH3 domain. However, more recently the term has been applied to the single chain monomer component consisting of CH3, CH2, and at least a portion of the hinge sufficient to form a disulfide-linked dimer with a second such chain. As such, and depending on the context, use of the terms "Fc region" or "Fc domain" will refer herein to either the dimeric form or the individual monomers that associate to form the dimeric protein. For a review of immunoglobulin structure and function, see Putnam, The Plasma Proteins, Vol. V (Academic Press, Inc., 1987), pp. 49-140; and Padlan, Mol. Immunol. 31:169-217, 1994. As used herein, the term Fc domain includes variants of naturally occurring sequences.

The term "immunoglobulin constant region" or "constant region" refers to a peptide or polypeptide sequence that corresponds to or is derived from part or all of one or more constant domains of an immunoglobulin (e.g., CH1, CH2, CH3). In certain embodiments, the constant region does not comprise a CH1 domain. In certain embodiments, the constant domains making up the constant region are human The terms "light chain variable region" (also referred to as "light chain variable domain" or "VL") and "heavy chain variable region" (also referred to as "heavy chain variable domain" or "VH") refer to the variable binding region from an antibody light and heavy chain, respectively. The variable binding regions are made up of discrete, well-defined subregions known as "complementarity determining regions" (CDRs) and "framework regions" (FRs).

The term "immunoglobulin light chain constant region" (also referred to as "light chain constant region" or "CL") is a constant region from an antibody light chain.

The term "immunoglobulin heavy chain constant region" (also referred to as "heavy chain constant region" or "CH") refers to the constant region from the antibody heavy chain. The CH is further divisible, depending on the antibody isotype into CH1, CH2, and CH3 (IgA, IgD, IgG), or CH1, CH2, CH3, and CH4 domains (IgE, IgM).

As used herein, the term "complementarity determining region" or "CDR" refer to an immunoglobulin (antibody) molecule. There are three CDRs per variable domain: CDR1, CDR2 and CDR3 in the variable domain of the light chain and CDR1, CDR2 and CDR3 in the variable domain of the heavy chain.

In some embodiments, a "hinge" or a "hinge region" refers to a polypeptide derived from an immunoglobulin hinge region and located between an antigen-binding domain (e.g., a ceramide-binding domain) and an immunoglobulin constant region in a polypeptide described herein. A "wild-type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a wild type immunoglobulin hinge region sequence is human, and can comprise a human IgG hinge region (e.g., and IgG1, IgG2, IgG3, or IgG4 hinge region).

An "altered immunoglobulin hinge region" or "variant immunoglobulin hinge region" refers to a hinge region polypeptide with one or more mutations, substitutions, insertions, or deletions compared to a corresponding parental wild-type immunoglobulin hinge region. Typically, an altered immunoglobulin hinge region that is a fragment of a wild type immunoglobulin hinge region comprises an IgG core hinge region (e.g., a polypeptide comprising the sequence C-X-X-C, wherein X is any amino acid) as disclosed in U.S. Patent Application Publication Nos. 2013/0129723 and 2013/0095097.

As used herein, the term "humanized" refers to an antibody or antigen-binding fragment thereof derived from a non-human species that retains the antigen-binding properties of the original non-human antibody. In some embodiments, the binding fragments of an antibody (e.g., light and heavy chain variable regions, Fab, scFv) are humanized. Non-human antigen-binding fragments can be humanized using techniques known as CDR grafting (Jones et al., Nature 321:522 (1986)) and variants thereof, including "reshaping" (Verhoeyen, et al., 1988 Science 239:1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312). If derived from a non-human source, other regions of the antibody, such as the hinge region and constant region domains, can also be humanized.

As used herein, the term "pharmaceutically acceptable" refers to molecular entities and compositions that do not generally produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

The term "polynucleotide" as referred to herein means single-stranded or double-stranded nucleic acid polymers. In certain embodiments, the nucleotides comprising the polynucleotide can be RNA or DNA or a modified form of either type of nucleotide, such as a modified messenger RNA. Said modifications may include, but are not limited to, base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

As used herein, a "polypeptide" or "protein" refers to a single, linear, and contiguous arrangement of covalently linked amino acids. Polypeptides can form one or more intrachain disulfide bonds. The terms polypeptide and protein also encompass embodiments where two polypeptide chains link together in a non-linear fashion, such as via an interchain disulfide bond. Herein, a protein or polypeptide may be an antibody or an antigen-binding fragment of an antibody.

As used herein, the term "transformation," "transfection," and "transduction" refer to the transfer of a polynucletide into a cell. As used herein, the term "genetic transformation" refers to the transfer and incorporation of DNA, especially recombinant DNA, into a cell. The transferred nucleic acid can be introduced into a cell via an expression vector.

As used herein, the terms "treatment," "treating," or "ameliorating" refers to either a therapeutic treatment or prophylactic/preventative treatment. A treatment is therapeutic if at least one symptom of disease in an individual receiving treatment improves or a treatment can delay worsening of a progressive disease in an individual or prevent onset of additional associated diseases.

As used herein, the term "LD90" refers to "Lethal Dose, 90%" or "median lethal dose" and is the amount of a substance required to kill 90% of a test population.

As used in this specification and the appended claims, the singular forms "a," "an" and "the" include plural references unless the content clearly dictates otherwise.

As used in this specification, the term "and/or" is used in this disclosure to either "and" or "or" unless indicated otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Anti-Ceramide Antibodies

The present disclosure provides antibodies or antigen-binding fragments thereof that specifically bind to ceramide. In some embodiments, the anti-ceramide antibody or antigen binding fragments thereof is humanized. In other embodiments, the anti-ceramide antibody is a humanized 6B5 scFv antibody.

The term "ceramide" as used herein refers to a lipid second messenger molecule comprised of sphingosine and a fatty acid. Ceramide regulates stress signaling within the cell through reorganization of the plasma membrane and formation of lateral liquid-ordered microdomains (a type of 'raft' termed 'ceramide-rich platforms'). These CRPs serve as signaling platforms that cluster activated receptor molecules (e.g., members of the TNF-receptor superfamily including Fas), thereby providing feed forward mechanisms that ultimately result in signaling amplification and signal transduction. CRP formation is particularly important for Fas-mediated cell death and ceramide-rich regions on the plasma membrane of target cells are critical for sensitivity to cytotoxic T lymphocyte (CTL)-induced cell death. Exemplary ceramides are glucosylceramides, galactosylceramides and gangliosides (oligosaccharide-linked ceramides).

In some embodiments, the present disclosure provides an antibody or antigen-binding fragment that specifically binds to ceramide and comprises an immunoglobulin heavy chain variable region (VH) comprising a heavy chain complementarity determining region (CDR) 1 (HCDR1), a heavy chain CDR2 (HCDR2), and a heavy chain CDR3 (HCDR3), and an immunoglobulin light chain variable region (VL) comprising a light chain complementarity determining region (CDR) 1 (LCDR1), a light chain CDR2 (LCDR2), and a light chain CDR3 (LCDR3), wherein the HCDR1 comprises an amino acid sequence selected from SEQ ID NO: 1 and 2; the HCDR2 comprises an amino acid sequence selected from SEQ ID NO: 3, 4, 5, and 6; the HCDR3 comprises the amino acid sequence of SEQ ID NO: 7; the LCDR1 comprises the amino acid sequence of SEQ ID NO: 8; the LCDR2 comprises the amino acid sequence of SEQ ID NO: 9; and the LCDR3 comprises the amino acid sequence of SEQ ID NO: 10.

The CDRs of exemplary anti-ceramide antibodies are shown in Table 1.

TABLE 1

Exemplary anti-ceramide antibody sequences

| Seq Desc. | Chain | Amino Acid Sequence | SEQ ID NO. |
|---|---|---|---|
| HCDR1-IH | Heavy | GYTFTDHTIH | 1 |
| HCDR1-IH-MH | Heavy | GYTFTDHTMH | 2 |
| HCDR2-DG | Heavy | YNYPRDGSTKYNEKFQG | 3 |
| HCDR2-DG-EG | Heavy | YNYPREGSTKYNEKFQG | 4 |
| HCDR2-DG-DV | Heavy | YNYPRDVSTKYNEKFQG | 5 |
| HCDR2-NE-AE | Heavy | YNYPRDGSTKYAEKFQG | 6 |
| HCDR3 | Heavy | GFITTWPSAY | 7 |
| LCDR1 | Light | RASKSISKYLA | 8 |
| LCDR2 | Light | SGSTLQS | 9 |

TABLE 1-continued

Exemplary anti-ceramide antibody sequences

| Seq Desc. | Chain | Amino Acid Sequence | SEQ ID NO. |
|---|---|---|---|
| LCDR3 | Light | QQHNEYPWT | 10 |
| Parental 6B5 HCDR1 | Heavy | GYTFTDHTIH | 11 |
| Parental 6B5 HCDR2 | Heavy | YNYPRDGSTKYNEKFKG | 12 |
| Parental 6B5 HCDR3 | Heavy | GFITTWPSAY | 13 |
| Parental 6B5 LCDR1 | Light | RASKSISKYLA | 14 |
| Parental 6B5 LCDR2 | Light | SGSTLQS | 15 |
| Parental 6B5 LCDR3 | Light | QQHNEYPWT | 16 |

In some embodiments, the anti-ceramide antibody or antigen-binding fragment thereof is an scFv comprising an immunoglobulin heavy chain variable region (VH) comprising a heavy chain complementarity determining region (CDR) 1 (HCDR1), a heavy chain CDR2 (HCDR2), and a heavy chain CDR3 (HCDR3), and an immunoglobulin light chain variable region (VL) comprising a light chain complementarity determining region (CDR) 1 (LCDR1), a light chain CDR2 (LCDR2), and a light chain CDR3 (LCDR3), wherein the HCDR1 comprises an amino acid sequence selected from SEQ ID NO: 1 and 2; the HCDR2 comprises an amino acid sequence selected from SEQ ID NO: 3, 4, 5, and 6; the HCDR3 comprises the amino acid sequence of SEQ ID NO: 7; the LCDR1 comprises the amino acid sequence of SEQ ID NO: 8; the LCDR2 comprises the amino acid sequence of SEQ ID NO: 9; and the LCDR3 comprises the amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 1; (b) the HCDR2 comprises the amino acid sequence of SEQ ID NO: 3; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 1; (b) the HCDR2 comprises the amino acid sequence of SEQ ID NO: 4; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 1; (b) the HCDR2 comprises the amino acid sequence of SEQ ID NO: 5; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 2; (b) the HCDR2 comprises the amino acid sequence of SEQ ID NO: 6; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 1; (b) the HCDR2 comprises the amino acid sequence of SEQ ID NO: 6; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 2; (b) the HCDR2 comprises the amino acid sequence of SEQ ID NO: 3; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 2; (b) the HCDR2 comprises the amino acid sequence of SEQ ID NO: 4; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 2; (b) the HCDR2 comprises the amino acid sequence of SEQ ID NO: 5; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 1; (b) the HCDR2 comprises the amino acid sequence of SEQ ID NO: 6; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 2; (b) the HCDR2 comprises the amino acid sequence of SEQ ID NO: 3; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 2; (b) the HCDR2 comprises the amino acid sequence of SEQ ID NO: 4; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises an HCDR1, HCDR2, HCDR3, LCDR1, LCDR2, and LCDR3, wherein (a) the HCDR1 comprises the amino acid sequence of SEQ ID NO: 2; (b) the HCDR2 comprises the amino acid sequence of SEQ ID NO: 5; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises an amino acid sequence of SEQ ID NO: 10.

In some embodiments, the anti-ceramide antibody or antigen-binding fragment thereof comprises a VH and a VL chain, wherein the VH chain comprises or consists of an amino acid sequence that is at least about 85%%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence selected from the group consisting of SEQ ID NOs: 17-21.

In some embodiments, the anti-ceramide antibody or antigen-binding fragment thereof comprises a VH and a VL chain, wherein the VL chain comprises or consists of an amino acid sequence that is at least about 85%%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence selected from the group consisting of SEQ ID NOs: 22-24.

In some embodiments, the anti-ceramide antibody or antigen-binding fragment thereof comprises a VH and a VL chain, wherein the VH chain comprises or consists of an amino acid sequence that is at least about 85%%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence selected from the group consisting of SEQ ID NOs: 17-21, and the VL chain comprises or consists of an amino acid sequence that is at least about 85%%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence selected from the group consisting of SEQ ID NOs: 22-24.

In some embodiments, the anti-ceramide antibody or antigen-binding fragment thereof is an scFv comprising a VH and a VL chain, wherein the VH chain comprises or consists of an amino acid sequence that is at least about 85%%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence selected from the group consisting of SEQ ID NOs: 17-21, and the VL chain comprises or consists of an amino acid sequence that is at least about 85%%, at least about 90%, at least about 91%, at least about 92%, at least about 93%, at least about 94%, at least about 95%, at least about 96%, at least about 97%, at least about 98%, at least about 99%, at least about 99.5%, or 10000 identical to an amino acid sequence selected from the group consisting of SEQ ID NOs: 22-24.

of SEQ ID NO: 22. In some embodiments, the antibody or antigen-fragment thereof comprises a VH amino acid sequence of SEQ ID NO: 18 and a VL amino acid sequence of SEQ ID NO: 23. In some embodiments, the antibody or antigen-fragment thereof comprises a VH amino acid sequence of SEQ ID NO: 18 and a VL amino acid sequence of SEQ ID NO: 24. In some embodiments, the antibody or antigen-fragment thereof comprises a VH amino acid sequence of SEQ ID NO: 19 and a VL amino acid sequence of SEQ ID NO: 22. In some embodiments, the antibody or antigen-fragment thereof comprises a VH amino acid sequence of SEQ ID NO: 19 and a VL amino acid sequence of SEQ ID NO: 23. In some embodiments, the antibody or antigen-fragment thereof comprises a VH amino acid sequence of SEQ ID NO: 19 and a VL amino acid sequence of SEQ ID NO: 24. In some embodiments, the antibody or antigen-fragment thereof comprises a VH amino acid sequence of SEQ ID NO: 20 and a VL amino acid sequence of SEQ ID NO: 22. In some embodiments, the antibody or antigen-fragment thereof comprises a VH amino acid sequence of SEQ ID NO: 20 and a VL amino acid sequence

TABLE 2

| Exemplary VH and VL Amino Acid Sequences | | | |
| --- | --- | --- | --- |
| Seq Desc. | Chain | Amino Acid Sequence | SEQ ID NO. |
| Humanized VH1 | Heavy | QVQLVQSGAEVKKPGASVKVSCKASGYTFTDHTMHWVRQA PGQGLEWMGYNYPRDGSTKYAEKFQGRVTMTADKSTSTVY MELSSLRSEDTAVYYCAKGFITTVVPSAYWGQGTLVTVSS | 17 |
| Humanized VH2 | Heavy | QVQLVQSGAEVKKPGASVKVSCKVSGYTFTDHTIHWMRQA PGQGLEWMGYNYPRDGSTKYNEKFQGRVTMTADKSTSTVY MELSSLRSEDTAVYYCAKGFITTVVPSAYWGQGTLVTVSS | 18 |
| Humanized VH3 | Heavy | QVQLVQSGAEVKKPGATVKISCKVSGYTFTDHTIHWMQQA PGKGLEWMGYNYPRDGSTKYNEKFQGRVTITADKSTSTAY MELSSLRSEDTAVYYCAKGFITTVVPSAYWGQGTLVTVSS | 19 |
| Humanized VH4 | Heavy | QVQLVQSGAEVKKPGASVKVSCKVSGYTFTDHTIHWMRQA PGQGLEWMGYNYPREGSTKYNEKFQGRVTMTADKSTSTVY MELSSLRSEDTAVYYCAKGFITTVVPSAYWGQGTLVTVSS | 20 |
| Humanized VH5 | Heavy | QVQLVQSGAEVKKPGASVKVSCKVSGYTFTDHTIHWMRQA PGQGLEWMGYNYPRDVSTKYNEKFQGRVTMTADKSTSTVY MELSSLRSEDTAVYYCAKGFITTVVPSAYWGQGTLVTVSS | 21 |
| Humanized VLI | Light | DIQLTQSPSFLSASVGDRVTITCRASKSISKYLAWYQQKP GKAPKLLIYSGSTLQSGVPSRFSGSGSGTEFTLTISSLQP EDFATYYCQQHNEYPWTFGGGTKVEIK | 22 |
| Humanized VL2 | Light | DVQITQSPSFLSASVGDRVTITCRASKSISKYLAWYQQKP GKANKLLIYSGSTLQSGVPSRFSGSGSGTDFTLTISSLQP EDFATYYCQQHNEYPWTFGGGTKVEIK | 23 |
| Humanized VL3 | Light | DVQLTQSPSSVSASVGDRVTITCRASKSISKYLAWYQQKP GKAPKLLIYSGSTLQSGVPSRFSGSGSGTDFTLTISSLQP EDFATYYCQQHNEYPWTFGPGTKVEIK | 24 |

In some embodiments, the anti-ceramide antibody or antigen-fragment thereof comprises a VH amino acid sequence of SEQ ID NO: 17 and a VL amino acid sequence of SEQ ID NO: 22. In some embodiments, the antibody or antigen-fragment thereof comprises a VH amino acid sequence of SEQ ID NO: 17 and a VL amino acid sequence of SEQ ID NO: 23. In some embodiments, the antibody or antigen-fragment thereof comprises a VH amino acid sequence of SEQ ID NO: 17 and a VL amino acid sequence of SEQ ID NO: 24. In some embodiments, the antibody or antigen-fragment thereof comprises a VH amino acid sequence of SEQ ID NO: 18 and a VL amino acid sequence of SEQ ID NO: 23. In some embodiments, the antibody or antigen-fragment thereof comprises a VH amino acid sequence of SEQ ID NO: 20 and a VL amino acid sequence of SEQ ID NO: 24. In some embodiments, the antibody or antigen-fragment thereof comprises a VH amino acid sequence of SEQ ID NO: 21 and a VL amino acid sequence of SEQ ID NO: 22. In some embodiments, the antibody or antigen-fragment thereof comprises a VH amino acid sequence of SEQ ID NO: 21 and a VL amino acid sequence of SEQ ID NO: 23. In some embodiments, the antibody or antigen-fragment thereof comprises a VH amino acid sequence of SEQ ID NO: 21 and a VL amino acid sequence of SEQ ID NO: 24.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 17 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 22. In some embodiments, the anti-ceramide antibody or antigen-binding fragment thereof comprises a VH chain and a VL chain, wherein the VH chain amino acid sequence consisting of SEQ ID NO: 17 and the VL amino acid sequence consists of SEQ ID NO: 22.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 17 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 23. In some embodiments, the anti-ceramide antibody or antigen-binding fragment thereof comprises a VH amino acid sequences consisting of 17 and a VL amino acid sequence consisting of 23.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 17 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 24. In some embodiments, the anti-ceramide antibody or antigen-binding fragment thereof comprises a VH chain and a VL chain, wherein the VH chain amino acid sequence consisting of SEQ ID NO: 17 and the VL amino acid sequence consists of SEQ ID NO: 24.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 18 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 22. In some embodiments, the anti-ceramide antibody or antigen-binding fragment thereof comprises a VH chain and a VL chain, wherein the VH chain amino acid sequence consisting of SEQ ID NO: 18 and the VL amino acid sequence consists of SEQ ID NO: 22.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 18 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 23. In some embodiments, the anti-ceramide antibody or antigen-binding fragment thereof comprises a VH chain and a VL chain, wherein the VH chain amino acid sequence consisting of SEQ ID NO: 18 and the VL amino acid sequence consists of SEQ ID NO: 23.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 18 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 24. In some embodiments, the anti-ceramide antibody or antigen-binding fragment thereof comprises a VH chain and a VL chain, wherein the VH chain amino acid sequence consisting of SEQ ID NO: 18 and the VL amino acid sequence consists of SEQ ID NO: 24.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 19 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 22. In some embodiments, the anti-ceramide antibody or antigen-binding fragment thereof comprises a VH chain and a VL chain, wherein the VH chain amino acid sequence consisting of SEQ ID NO: 19 and the VL amino acid sequence consists of SEQ ID NO: 22.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 19 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 23. In some embodiments, the anti-ceramide antibody or antigen-binding fragment thereof comprises a VH chain and a VL chain, wherein the VH chain amino acid sequence consisting of SEQ ID NO: 19 and the VL amino acid sequence consists of SEQ ID NO: 23.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 19 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 24. In some embodiments, the anti-ceramide antibody or antigen-binding fragment thereof comprises a VH chain and a VL chain, wherein the VH chain amino acid sequence consisting of SEQ ID NO: 19 and the VL amino acid sequence consists of SEQ ID NO: 24.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 20 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 22. In some embodiments, the anti-ceramide antibody or antigen-binding fragment thereof comprises a VH chain and a VL chain, wherein the VH chain amino acid sequence consisting of SEQ ID NO: 20 and the VL amino acid sequence consists of SEQ ID NO: 22.

In some embodiments, the anti-ceramide antibody or antigen-binding fragment thereof comprises a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 21 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 22. In some embodiments, the anti-ceramide antibody or antigen-binding fragment thereof comprises a VH chain and a VL chain, wherein the VH chain amino acid sequence consisting of SEQ ID NO: 21 and the VL amino acid sequence consists of SEQ ID NO: 22.

In some embodiments, the anti-ceramide antigen-binding fragment is an scFv comprising a VH amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 18 and a VL amino acid sequence that is at least about 85%, at least about 90%, at least about 91%, at least about 92%, at least about 93%, at least about 94%, at least about 95%, at least about 96%, at least about 97%, at least about 98%, at least about 99%, at least about 99.5%, or 100% identical to SEQ ID NO: 22. In some embodiments, the anti-ceramide scFv comprises a VH chain and a VL chain, wherein the VH chain amino acid sequence consisting of SEQ ID NO: 18 and the VL amino acid sequence consists of SEQ ID NO: 22.

In some embodiments, the anti-ceramide antigen-binding fragment thereof is an scFv. In some embodiments, the anti-ceramide scFv comprises an amino acid sequence that is at least about 80%, at least about 82%, at least about 85%, at least about 87%, at least about 90%, at least about 91%, at least about 92%, at least about 93%, at least about 94%, at least about 95%, at least about 96%, at least about 97%, at least about 98%, at least about 99%, or 100% identical to an amino acid sequence selected from the group consisting of SEQ ID NOs: 48-61. In some embodiments, the anti-ceramide scFv consists of an amino acid sequence selected from the group consisting of SEQ ID NOs: 48-61 In some embodiments, the anti-ceramide scFv comprises or consists of the amino acid sequence of SEQ ID NOs: 48 or 51.

In some embodiments, the anti-ceramide scFv comprises the following structure: VH-linker-VL or VL-linker-VH. As used herein, the term "linker" generally refers to a short polypeptide sequence connecting two sub-domains of a polypeptide. Non-limiting examples of linkers include flexible linkers comprising glycine-serine repeats, and linkers derived from (a) an interdomain region of a transmembrane protein (e.g., a type I transmembrane protein); (b) a stalk region of a type II C-lectin; or (c) an immunoglobulin hinge. In some embodiments, a linker provides a spacer function compatible with interaction of the two sub-binding domains so that the resulting polypeptide retains a specific binding affinity to the same target molecule as an antibody that comprises the same light and heavy chain variable regions. In certain embodiments, a linker is comprised of five to about 35 amino acids, for instance, about 15 to about 25 amino acids. Exemplary linkers are shown in Table 3.

TABLE 3

| Exemplary linkers | | |
|---|---|---|
| Linker | Amino Acid Sequence | SEQ ID |
| STD1 | NYGGGGSGGGGSGGGGSGNS | 25 |
| STD2 | NYGGGGSGGGGSGGGGSGNY GGGGSGGGGSGGGGSGNS | 26 |
| H1 | NS | 27 |
| H2 | GGGGSGNS | 28 |
| H3 | NYGGGGSGNS | 29 |
| H4 | GGGGSGGGGSGNS | 30 |
| H5 | NYGGGGSGGGGSGNS | 31 |
| H6 | GGGGSGGGGSGGGGSGNS | 32 |
| H7 | GCPPCPNS | 33 |
| Gly$_4$Ser | GGGGS | 34 |
| (G$_4$S)$_3$ | GGGGSGGGGSGGGGS | 35 |
| H105 | SGGGGSGGGGSGGGGS | 36 |
| (G$_4$S)$_4$ | GGGGSGGGGSGGGGSGGGGS | 37 |
| H75 (NKG2A quadruple mutant) | QRHNNSSLNTGTQMAGHSPNS | 38 |
| H83 (NKG2A derived) | SSLNTGTQMAGHSPNS | 39 |
| H106 (NKG2A derived) | QRHNNSSLNTGTQMAGHS | 40 |

TABLE 3-continued

Exemplary linkers

| Linker | Amino Acid Sequence | SEQ ID |
|---|---|---|
| H81 (NKG2D derived) | EVQIPLTESYSPNS | 41 |
| H91 (NKG2D derived) | NSLANQEVQIPLTESYSPNS | 42 |
| H94 | SGGGGSGGGGSGGGGSPNS | 43 |
| H111 | SGGGGSGGGGSGGGGSPGS | 44 |
| H113 | SGGGGSGGGGSGGGGSPAS | 45 |
| H114 | SGGGGSGGGGSGGGGSPS | 46 |
| H115 | SGGGGSGGGGSGGGGSPGS | 47 |

In some embodiments, the anti-ceramide antibody or antigen-binding fragments thereof is produced with an N-terminal signal sequence to promote secretion of the scFv protein. In some embodiments, the signal sequence comprises SEQ ID NO: 75. One of skill in the art will understand that these signal sequences are not a part of the mature, secreted protein. Therefore, in some embodiments, the signal sequence of SEQ ID NO: 75 is cleaved from the mature anti-ceramide antibody or antigen-binding fragment protein.

In some embodiments, the anti-ceramide antibody or antigen-binding fragments thereof are produced with a C-terminal tag sequence to facilitate purification during manufacturing. In some embodiments, the C-terminal tag comprises the amino acid sequence of SEQ ID NO: 76. In some embodiments, the anti-ceramide antibody or antigen-binding fragments thereof are produced without a C-terminal tag sequence. Therefore, in some embodiments, the amino sequences of the anti-ceramide antibody or antigen-binding fragments thereof do not comprise the C-terminal tag of SEQ ID NO: 76.

Exemplary amino acid sequences for the anti-ceramide scFvs are provided in Table 4 below. The CDRs of the scFvs are indicated by underlined text. Linker sequences are indicated by italicized text. Signal sequences are indicated by bold text. C-terminal tag sequences are indicated by bold and italicized text.

TABLE 4

Amino Acid Sequences of Exemplary anti-ceramide scFvs

| scFv | Amino Acid Sequence | SEQ ID ID | SEQ ID SEQforVH CDRs | SEQ ID forVL CDRs |
|---|---|---|---|---|
| VH2-VL1 (with signal sequence) | MEWSWVFLFFLSVTTGVHSQVQLVQSGAEVKKPGASVKVSCKV SGYTFTDHTIHWMRQAPGQGLEWMGYNYPRDGSTKYNEKFQGR VTMTADKSTSTVYMELSSLRSEDTAVYYCAKGFITTVVPSAYW GQGTLVTVSSGGGGSGGGGSGGGGSDIQLTQSPSFLSASVGDR VTITCRASKSISKYLAWYQQKPGKAPKLLIYSGSTLQSGVPSR FSGSGSGTEFTLTISSLQPEDFATYYCQQHNEYPWTFGGGTKV EIKRAAAGGGGSGGGGSHHHHHHHH | 48 | 1, 3, 7 | 8, 9, 10 |
| VH4-VL1 (with signal sequence) | MEWSWVFLFFLSVTTGVHSQVQLVQSGAEVKKPGASVKVSCKV SGYTFTDHTIHWMRQAPGQGLEWMGYNYPREGSTKYNEKFQGR VTMTADKSTSTVYMELSSLRSEDTAVYYCAKGFITTVVPSAYW GQGTLVTVSSGGGGSGGGGSGGGGSDIQLTQSPSFLSASVGDR VTITCRASKSISKYLAWYQQKPGKAPKLLIYSGSTLQSGVPSR FSGSGSGTEFTLTISSLQPEDFATYYCQQHNEYPWTFGGGTKV EIKRAAAGGGGSGGGGSHHHHHHHH | 49 | 1, 4, 7 | 8, 9, 10 |
| VH5-VL1 (with signal sequence) | MEWSWVFLFFLSVTTGVHSQVQLVQSGAEVKKPGASVKVSCKV SGYTFTDHTIHWMRQAPGQGLEWMGYNYPRDVSTKYNEKFQGR VTMTADKSTSTVYMELSSLRSEDTAVYYCAKGFITTVVPSAYW GQGTLVTVSSGGGGSGGGGSGGGGSDIQLTQSPSFLSASVGDR VTITCRASKSISKYLAWYQQKPGKAPKLLIYSGSTLQSGVPSR FSGSGSGTEFTLTISSLQPEDFATYYCQQHNEYPWTFGGGTKV EIKRAAAGGGGSGGGGSHHHHHHHH | 50 | 1, 5, 7 | 8, 9, 10 |
| VH2-VL1 ("scFv #4") | QVQLVQSGAEVKKPGASVKVSCKVSGYTFTDHTIHWMRQAPGQ GLEWMGYNYPRDGSTKYNEKFQGRVTMTADKSTSTVYMELSSL RSEDTAVYYCAKGFITTVVPSAYWGQGTLVTVSSGGGGSGGGG SGGGGSDIQLTQSPSFLSASVGDRVTITCRASKSISKYLAWYQ QKPGKAPKLLIYSGSTLQSGVPSRFSGSGSGTEFTLTISSLQP EDFATYYCQQHNEYPWTFGGGTKVEIKRAAAGGGGS GGGGSHHHHHHHH | 51 | 1, 3, 7 | 8, 9, 10 |
| VH4-VL1 | QVQLVQSGAEVKKPGASVKVSCKVSGYTFTDHTIHWMRQAPGQ GLEWMGYNYPREGSTKYNEKFQGRVTMTADKSTSTVYMELSSL RSEDTAVYYCAKGFITTVVPSAYWGQGTLVTVSSGGGGSGGGG SGGGGSDIQLTQSPSFLSASVGDRVTITCRASKSISKYLAWYQ QKPGKAPKLLIYSGSTLQSGVPSRFSGSGSGTEFTLTISSLQP EDFATYYCQQHNEYPWTFGGGTKVEIKRAAAGGGGS GGGGSHHHHHHHH | 52 | 1, 4, 7 | 8, 9, 10 |

TABLE 4-continued

Amino Acid Sequences of Exemplary anti-ceramide scFvs

| scFv | Amino Acid Sequence | SEQ ID forVH ID CDRs | SEQ ID forVL CDRs |
|---|---|---|---|
| VH5-VL1 | QVQLVQSGAEVKKPGASVKVSCKVSGYTFTDHTIHWMRQAPGQ GLEWMGYNYPRDVSTKYNEKFQGRVTMTADKSTSTVYMELSSL RSEDTAVYYCAKGFITTVVPSAYWGQGTLVTVSSGGGGSGGGG SGGGGSDIQLTQSPSFLSASVGDRVTITCRASKSISKYLAWYQ QKPGKAPKLLIYSGSTLQSGVPSRFSGSGSGTEFTLTISSLQP EDFATYYCQQHNEYPWTFGGGTKVEIKRAAAGGGGS GGGGSHHHHHHH | 53 1, 5, 7 | 8, 9, 10 |
| VH1-VL1 ("scFv #1") | QVQLVQSGAEVKKPGASVKVSCKASGYTFTDHTMHWVRQAPGQ GLEWMGYNYPRDGSTKYAEKFQGRVTMTADKSTSTVYMELSSL RSEDTAVYYCAKGFITTVVPSAYWGQGTLVTVSSGGGGSGGGG SGGGGSDIQLTQSPSFLSASVGDRVTITCRASKSISKYLAWYQ QKPGKAPKLLIYSGSTLQSGVPSRFSGSGSGTEFTLTISSLQP EDFATYYCQQHNEYPWTFGGGTKVEIKRAAAGGGGS GGGGSHHHHHHH | 54 2, 6, 7 | 8, 9, 10 |
| VH1-VL2 | QVQLVQSGAEVKKPGASVKVSCKASGYTFTDHTMHWVRQAPGQ GLEWMGYNYPRDGSTKYAEKFQGRVTMTADKSTSTVYMELSSL RSEDTAVYYCAKGFITTVVPSAYWGQGTLVTVSSGGGGSGGGG SGGGGSDVQITQSPSFLSASVGDRVTITCRASKSISKYLAWYQ QKPGKANKLLIYSGSTLQSGVPSRFSGSGSGTDFTLTISSLQP EDFATYYCQQHNEYPWTFGGGTKVEIKRAAAGGGGS GGGGSHHHHHHH | 55 2, 6, 7 | 8, 9, 10 |
| VH1-VL3 ("scFv #3") | QVQLVQSGAEVKKPGASVKVSCKASGYTFTDHTMHWVRQAPGQ GLEWMGYNYPRDGSTKYAEKFQGRVTMTADKSTSTVYMELSSL RSEDTAVYYCAKGFITTVVPSAYWGQGTLVTVSSGGGGSGGGG SGGGGSDVQLTQSPSSVSASVGDRVTITCRASKSISKYLAWYQ QKPGKAPKLLIYSGSTLQSGVPSRFSGSGSGTDFTLTISSLQP EDFATYYCQQHNEYPWTFGPGTKVEIKRAAAGGGGS GGGGSHHHHHHH | 56 2, 6, 7 | 8, 9, 10 |
| VH2-VL2 ("scFv #5") | QVQLVQSGAEVKKPGASVKVSCKVSGYTFTDHTIHWMRQAPGQ GLEWMGYNYPRDGSTKYNEKFQGRVTMTADKSTSTVYMELSSL RSEDTAVYYCAKGFITTVVPSAYWGQGTLVTVSSGGGGSGGGG SGGGGSDVQITQSPSFLSASVGDRVTITCRASKSISKYLAWYQ QKPGKANKLLIYSGSTLQSGVPSRFSGSGSGTDFTLTISSLQP EDFATYYCQQHNEYPWTFGGGTKVEIKRAAAGGGGS GGGGSHHHHHHH | 57 1, 3, 7 | 8, 9, 10 |
| VH2-VL3 | QVQLVQSGAEVKKPGASVKVSCKVSGYTFTDHTIHWMRQAPGQ GLEWMGYNYPRDGSTKYNEKFQGRVTMTADKSTSTVYMELSSL RSEDTAVYYCAKGFITTVVPSAYWGQGTLVTVSSGGGGSGGGG SGGGGSDVQLTQSPSSVSASVGDRVTITCRASKSISKYLAWYQ QKPGKAPKLLIYSGSTLQSGVPSRFSGSGSGTDFTLTISSLQP EDFATYYCQQHNEYPWTFGPGTKVEIKRAAAGGGGS GGGGSHHHHHHH | 58 1, 3, 7 | 8, 9, 10 |
| VH3-VL1 ("scFv #7") | QVQLVQSGAEVKKPGATVKISCKVSGYTFTDHTIHWMQQAPGK GLEWMGYNYPRDGSTKYNEKFQGRVTITADKSTSTAYMELSSL RSEDTAVYYCAKGFITTWPSAYWGQGTLVTVSSGGGGSGGGG SGGGGSDIQLTQSPSFLSASVGDRVTITCRASKSISKYLAWYQ QKPGKAPKLLIYSGSTLQSGVPSRFSGSGSGTEFTLTISSLQP EDFATYYCQQHNEYPWTFGGGTKVEIKRAAAGGGGS GGGGSHHHHHHH | 59 1, 3, 7 | 8, 9, 10 |
| VH3-VL2 ("scFv #8") | QVQLVQSGAEVKKPGATVKISCKVSGYTFTDHTIHWMQQAPGK GLEWMGYNYPRDGSTKYNEKFQGRVTITADKSTSTAYMELSSL RSEDTAVYYCAKGFITTVVPSAYWGQGTLVTVSSGGGGSGGGG SGGGGSDVQITQSPSFLSASVGDRVTITCRASKSISKYLAWYQ QKPGKANKLLIYSGSTLQSGVPSRFSGSGSGTDFTLTISSLQP EDFATYYCQQHNEYPWTFGGGTKVEIKRAAAGGGGS GGGGSHHHHHHH | 60 1, 3, 7 | 8, 9, 10 |
| VH3-VL3 | QVQLVQSGAEVKKPGATVKISCKVSGYTFTDHTIHWMQQAPGK GLEWMGYNYPRDGSTKYNEKFQGRVTITADKSTSTAYMELSSL RSEDTAVYYCAKGFITTVVPSAYWGQGTLVTVSSGGGGSGGGG SGGGGSDVQLTQSPSSVSASVGDRVTITCRASKSISKYLAWYQ QKPGKAPKLLIYSGSTLQSGVPSRFSGSGSGTDFTLTISSLQP EDFATYYCQQHNEYPWTFGPGTKVEIKRAAAGGGGS GGGGSHHHHHHH | 61 1, 3, 7 | 8, 9, 10 |

TABLE 4-continued

Amino Acid Sequences of Exemplary anti-ceramide scFvs

| scFv | Amino Acid Sequence | SEQ ID ID CDRs | SEQforVH | SEQ ID forVL CDRs |
|------|---------------------|----------------|----------|-------------------|
| Mouse 6B5 | MKKTAIAIAVALAGFATVAQAQVQLQQSDAELVKPGASVKISC KVSGYTFTDHTIHWMKQRPEQGLEWIGYNYPRDGSTKYNEKFK GKATLTADKSSSTAYMQLNSLTSEDSAVYFCAKGFITTVVPSA YWGQGTLVTVSAGGGGSGGGGSGGGGSDVQITQSPSYLAASPG ETITINCRASKSISKYLAWYQEKPGKTNKLLIYSGSTLQSGIP SRFSGSGSGTDFTLTISSLEPEDFAMYYCQQHNEYPWTFGGGT KLEIKGSHHHHHH | 62 | 1, 12, 7 | 8, 9, 10 |

15

In some embodiments, the anti-ceramide antibody is a full-length antibody comprising a full length antibody light chain and a full length antibody heavy chain. In some embodiments, the anti-ceramide antibody is an IgG isotype (e.g. IgG1, IgG2, IgG3, IgG4). In some embodiments, the Fc domain of the anti-ceramide antibody comprises a wild-type IgG amino acid sequence. Such sequences are known in the art, see e.g. Shields et al., J Biol Chem, (2001) 276:9; 6591-6604. In some embodiments, the CH2 or CH3 domain of the Fc domain comprises one or more amino acid mutations that alter the function and/or stability of the antibody. For example, in some embodiments, the Fc domain of an anti-ceramide antibody described herein lacks or has minimal effector functions while retaining the ability to bind some Fc receptors such as the neonatal Fc receptor (FcRn) and retaining a relatively long half-life in vivo. In some embodiments, anti-ceramide antibodies described do not result in, or substantially reduce the induction of, antibody-dependent cell-mediated cytotoxicity (ADCC), antibody-dependent cell-mediated phagocytosis (ADCP), complement activation, and/or complement-dependent cytotoxicity (CDC). Such mutations are well known in the art, see for example Shields et al., J Biol Chem, (2001) 276:9; 6591-6604; Arduin et al., Mol Immunol (2015) 63:2; 456-463; Vafa et al., Methods (2014) 65:1; 114-126.

In some embodiments, the anti-ceramide antibodies described are IgG1 isotype antibodies, wherein the IgG1 constant region has a mutation at one or more of the following positions: 228 (S228), 234 (L234), 235 (L235), 237 (G237), 297 (N297), 318 (E318), 320 (K320), 322 (K322), or any combination thereof (numbering according to EU). In some embodiments, the IgG1 Fc domain has an L234A and L235A mutation. In some embodiments, the IgG1 Fc domain has an S228P mutation.

As used herein, unless otherwise provided, a position of an amino acid residue in an immunoglobulin molecule is numbered according to EU nomenclature (Ward et al., 1995 *Therap. Immunol.* 2:77-94). Other numbering systems for amino acid positions within antibodies are known in the art. For example, the IMGT system (Brochet et al, Nucl. Acids Res. (2008) 36, W503-508) and the Kabat numbering system (Kabat, Sequences of Proteins of Immunological Interest, 5th edition, Bethesda, MD: Public Health Service, National Institutes of Health (1991)). Methods and information to convert between one numbering system and the other are known in the art. See, for example, the IMGT Scientific Chart—Correspondence between C numberings, available at imgt.org.

In certain embodiments, the anti-ceramide antibodies and antigen-binding fragments thereof may be prepared using standard molecular biology techniques with regard to selecting antibodies that have a desired specificity. In some embodiments, the anti-ceramide antibodies and antigen-binding fragments thereof are produced using recombinant DNA technologies. Procedures for the expression and purification of recombinant proteins are well established in the art.

Polynucleotides and Methods of Protein Expression

The disclosure also includes polynucleotides (e.g., DNA or RNA) encoding the anti-ceramide antibodies and antigen-binding fragments thereof of the present disclosure. In some embodiments, the polynucleotides encode a polypeptide that is substantially identical to a polypeptide listed in Tables 1, 2, 3 and 4. In some embodiments, the polynucleotides encode a polypeptide that is at least about 80%, at least about 90%, at least about 95%, at least about 96%, at least about 97%, at least about 98%, at about least 99%, or at about least 100% identical to a polypeptide listed in Tables 1, 2, 3 and 4. Polynucleotides of the disclosure also include complementary nucleic acids. In some instances, the sequences will be fully complementary (no mismatches) when aligned. In other instances, there can be up to about a 20% mismatch in the sequences. The polynucleotide sequences provided herein can be exploited using codon optimization, degenerate sequence, silent mutations, and other DNA techniques to optimize expression in a particular host, and the present disclosure encompasses such sequence modifications.

In some embodiments, the disclosure provides an isolated polynucleotide encoding an anti-ceramide antibody or antigen-binding fragment thereof, wherein said polynucleotide is at least 80%, at least 85%, at least 90%, at least 95%, at least 96%, at least 97%, at least 98%, at least 99%, or is 100% identical to a nucleic acid sequence selected from the group consisting of SEQ ID NOs: 65-73. In some embodiments, the disclosure provides an isolated polynucleotide encoding an anti-ceramide antibody or antigen-binding fragment thereof, wherein said polynucleotide comprises or consists of a nucleic acid sequence selected from the group consisting of SEQ ID NOs: 65-73.

In some embodiments, the polynucleotides of the present disclosure are inserted into a nucleic acid vector. The nucleic acid vector may be a viral vector or a non-viral vector, e.g. a plasmid. Vectors include, without limitation, plasmids, phagemids, cosmids, transposons, artificial chromosomes such as yeast artificial chromosome (YAC), bacterial artificial chromosome (BAC), or P1-derived artificial chromosome (PAC), bacteriophages such as lambda phage or M13 phage, and animal viruses. In some embodiments, the vector is a plasmid selected from pXT1, pSG5 (Stratagene), pSVK3, pBPV, pMSG, and pSVLSV40 (Pharmacia). In some embodiments, the vector is a viral vector selected from viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., U.S. Pat. No. 7,078,387; Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166: 154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Examples of vectors are pClneo vectors (Promega) for expression in mammalian cells; pLenti4/V5-DEST™, pLenti6/V5-DEST™, and pLenti6.2/V5-GW/lacZ (Invitrogen™) for lentivirus-mediated gene transfer and expression in mammalian cells.

In some embodiments, the polynucleotide is inserted into a nucleic acid vector and is operably linked to one or more regulatory sequences that control transcription, such as promoters, enhancers, terminators, inducers, or repressors. Exemplary promoters include Non-limiting examples of suitable eukaryotic promoters (promoters functional in a eukaryotic cell) include those from cytomegalovirus (CMV) immediate early, herpes simplex virus (HSV) thymidine kinase, a viral simian virus 40 (SV40) (e.g., early and late SV40), a spleen focus forming virus (SFFV) promoter, long terminal repeats (LTRs) from retrovirus (e.g., a Moloney murine leukemia virus (MoMLV) LTR promoter or a Rous sarcoma virus (RSV) LTR), a herpes simplex virus (HSV) (thymidine kinase) promoter, H5, P7.5, and P11 promoters from vaccinia virus, an elongation factor 1-alpha (EF1$\alpha$) promoter, early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a $\beta$-kinesin ($\beta$-KIN) promoter, the human ROSA 26 locus (Irions et al., Nature Biotechnology 25, 1477-1482 (2007)), a Ubiquitin C (UBC) promoter, a phosphoglycerate kinase-1 (PGK) promoter, a cytomegalovirus enhancer/ chicken $\beta$-actin (CAG) promoter, a $\beta$-actin promoter and a myeloproliferative sarcoma virus enhancer, negative control region deleted, dl587rev primer-binding site substituted (MND) promoter, and mouse metallothionein-1.

In some embodiments, the vector is introduced into a host cell for expression of the anti-ceramide antibody or antigen-binding fragment thereof. Accordingly, proteins for use within the present disclosure can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells.

Techniques for manipulating cloned DNA molecules and introducing exogenous DNA into a variety of host cells are disclosed by Sambrook and Russell, Molecular Cloning: A Laboratory Manual (3rd ed., Cold Spring Harbor Laboratory Press, Cold Spring Harbor, NY, 2001), and Ausubel et al., Short Protocols in Molecular Biology (4th ed., John Wiley & Sons, 1999).

The gene product encoded by a polynucleotide of the disclosure is expressed in any convenient expression system, including, for example, bacterial, yeast, insect, amphibian, and mammalian systems. Examples of suitable mammalian host cells include African green monkey kidney cells (Vero; American Type Culture Collection (ATCC) CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, UT); see also, e.g., Chasin et al., Som. Cell. Molec. Genet. 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Virginia. Introduction of the DNA construct can use any convenient method, including, e.g. conjugation, bacterial transformation, calcium-precipitated DNA, electroporation, fusion, transfection, infection with viral vectors, biolistics, and the like.

For example, for recombinant expression of an anti-ceramide antibody or antigen-binding fragment thereof as described herein, an expression vector will generally include a nucleic acid segment encoding one or more of the amino acid sequences provided in Tables 1, 2, 3 and 4, operably linked to a promoter. The expression vector is introduced to a host cell by conventional techniques, and the host cells are then cultured by conventional techniques to produce the encoded polypeptide(s) to produce the corresponding anti-ceramide antibodies or antigen-binding fragments thereof.

To direct a recombinant protein into the secretory pathway of a host cell, a secretory signal sequence (also known as a leader sequence) is provided in the expression vector. The secretory signal sequence can be that of the native form of the recombinant protein or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., U.S. Pat. Nos. 5,037,743 and 5,143,830). In some embodiments, the secretory signal sequence is SEQ ID NO: 75.

Cultured mammalian cells are suitable hosts for production of recombinant polypeptides and proteins of the present disclosure (e.g., anti-ceramide antibodies and antigen-binding fragments thereof). Methods for introducing exogenous DNA into mammalian host cells include calcium phosphate-mediated transfection (Wigler et al., Cell 14:725, 1978; Corsaro and Pearson, Somatic Cell Genetics 7:603, 1981: Graham and Van der Eb, Virology 52:456, 1973), electroporation (Neumann et al., EMBO J. 1:841-845, 1982), DEAE-dextran mediated transfection (Ausubel et al., supra), and liposome-mediated transfection (Hawley-Nelson et al., Focus 15:73, 1993; Ciccarone et al., Focus 15:80, 1993). The production of recombinant polypeptides in cultured mammalian cells is disclosed by, for example, U.S. Pat. Nos. 4,713,339; 4,784,950; 4,579,821; and 4,656,134.

Transformed or transfected host cells to produce the polypeptides and proteins of the present disclosure (e.g., ceramide-binding polypeptides) are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins, and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The anti-ceramide antibodies and antigen-binding fragments thereof of the present disclosure may be purified by conventional protein purification methods, typically by a combination of chromatographic techniques. See generally *Affinity Chromatography: Principles & Methods* (Pharmacia LKB Biotechnology, Uppsala, Sweden, 1988); Scopes, *Protein Purification: Principles and Practice* (Springer-Verlag, New York 1994). Proteins comprising an immunoglobulin Fc region can be purified by affinity chromatography on immobilized protein A or protein G. Additional purification steps, such as gel filtration, can be used to obtain the desired level of purity or to provide for desalting, buffer exchange, and the like.

Methods of Humanized Antibody Generation

The present disclosure discloses humanized anti-ceramide antibodies and antigen-binding fragments thereof. Humanized antibodies have the same or similar binding specificity and affinity as a mouse or other nonhuman antibody that provides the starting material for construction of a humanized antibody. A preferred antibody for humanization is the murine 6B5 antibody described in US 2017-0333413, incorporated herein by reference in its entirety. The VH and VL sequences of the murine 6B5 antibody are provided below in Table 5. The CDRs are indicated by underlined text. Linker sequences are indicated by italicized text. Signal sequences are indicated by bold text. C-terminal tag sequences are indicated by bold and italicized text.

The substitution of mouse CDRs into a human variable domain framework is most likely to result in retention of their correct spatial orientation if the human variable domain framework adopts the same or similar conformation to the murine variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human variable framework region sequences can be the sequences of naturally occurring human antibodies or can be consensus sequences of several human antibodies. See Kettleborough et al., *Protein Engineering* 4:773 (1991); Kolbinger et al., *Protein Engineering* 6:971 (1993) and Carter et al., WO 92/22653.

Having identified the CDRs of the murine donor immunoglobulin and appropriate human acceptor framework region, the next step is to determine which, if any, residues from these components should be modified to optimize the properties of the resulting humanized antibody. In general, substitution of human amino acid residues with murine residues should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials.

In some embodiments, the selection of amino acid residues for modification is determined, in part, by computer modeling. Computer hardware and software are described herein for producing three-dimensional images of immunoglobulin molecules. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90%, or more sequence identity are selected for modeling. The solved starting structures are modified to allow for differences between the actual amino acids in the immunoglobulin chains or domains being modeled, and those in the starting structure. The modified structures are then assembled into a

TABLE 5

| Murine 6B5 VH and VL sequences from anti-ceramide antibodies | | |
|---|---|---|
| 6B5 Fragment | Amino Acid Seq | SEQ ID: |
| 6B5 VH | QVQLQQSDAELVKPGASVKISCKVSGYTFTDHTIHWMKQRPEQGLEWIG<u>YNYPRD</u> <u>GSTKYNEKFKG</u>KATLTADKSSSTAYMQLNSLTSEDSAVYFCAKG<u>FITTVVPSAYW</u> <u>G</u>QGTLVTVSA | 63 |
| 6B5 VL | DVQITQSPSYLAASPGETITINC<u>RASKSISKYLA</u>WYQEKPGKTNKLLIY<u>SGSTLQ</u> <u>S</u>GIPSRFSGSGSGTDFTLTISSLEPEDFAMYYC<u>QQHNEYPWT</u>FGGGTKLEIK | 64 |
| 6B5 scFv | MKKTAIAIAVALAGFATVAQAQVQLQQSDAELVKPGASVKISCKVS<u>GYTFTDHTI</u> <u>H</u>WMKQRPEQGLEWIG<u>YNYPRDGSTKYNEKFKG</u>KATLTADKSSSTAYMQLNSLTSE DSAVYFCAKG<u>FITTVVPSAYW</u>GQGTLVTVSAGGGGSGGGGSGGGGSDVQITQSPS YLAASPGETITINC<u>RASKSISKYLA</u>WYQEKPGKTNKLLIY<u>SGSTLQ</u>SGIPSRFSG SGSGTDFTLTISSLEPEDFAMYYC<u>QQHNEYPWT</u>FGGGTKLEIK*GSHHHHHHHH* | 62 | composite immunoglobulin. Finally, the model is refined by energy minimization and by verifying that all atoms are within appropriate distances from one another and that bond lengths and angles are within chemically acceptable limits.

The selection of amino acid residues for modification can also be determined, in part, by examination of the characteristics of the amino acids at particular locations, or empirical observation of the effects of substitution or mutagenesis of particular amino acids.

Additional exemplary humanization techniques that can be used for humanizing the immunoglobulins of the disclosure are described in, for example, Presta et al., J. Immunol., 151: 2623-2632 (1993); Carter et al., Proc. Natl. Acad. Sci. USA., 89: 4285-4289 (1992); Couto et al., Cancer Res., 55: 5973s-77s (1995); O'Conner et al., Protein Eng., 11: 321-328 (1998); and Antibody Engineering—Methods and Protocols by Lo, Vol. 248 (2004).

Usually the CDR regions in humanized antibodies are identical to the corresponding CDR regions of the murine donor antibody. For example, in some embodiments, the CDR amino acid sequences of the humanized antibodies and fragments thereof are identical to the CDR amino acid sequences of the murine 6B5 antibody (e.g., SEQ ID NOs: 11-16).

In some embodiments, it may be desirable to modify one or more CDR regions to modify the antigen binding specificity of the antibody and/or reduce the immunogenicity of the antibody. In some embodiments, one or more residues of a CDR are altered to modify binding to achieve a more favored on-rate of binding, a more favored off-rate of binding, or both, such that an idealized binding constant is achieved. Using this strategy, an antibody having high binding affinity of, for example, $10^{10}$ M$^{-1}$ or more, can be achieved. Affinity maturation techniques, as described herein, can be used to alter the parent CDR region(s) followed by screening of the resultant binding molecules for the desired change in binding. The method may also be used to alter the parent CDR to be less immunogenic such that a potential human anti-mouse antibody (HAMA) response is minimized or avoided. Accordingly, as CDR(s) are altered, changes in binding affinity as well as immunogenicity can be monitored and scored such that an antibody optimized for the best combined binding and low immunogenicity are achieved (see, e.g., U.S. Pat. No. 6,656,467 and U.S. Pat. Pub. US20020164326A1). Moreover, it is sometimes possible to make one or more conservative amino acid substitutions of CDR residues without appreciably affecting the binding affinity of the resulting humanized immunoglobulin. Conservative substitutions are intended combinations such as gly, ala; val, ile, leu; asp, glu; asn, gln; ser, thr; lys, arg; and phe, tyr.

In some embodiments, the humanized anti-ceramide antibodies and antigen-binding fragments thereof comprise one or more mutations relative to the corresponding CDR sequence of the murine 6B5 antibody (e.g., relative to one or more of SEQ ID NOs: 11-16). Exemplary mutations to the CDR amino acid sequences of the murine 6B5 CDRs are shown in bold text in FIG. 4A.

The framework regions of humanized immunoglobulins are usually substantially identical, and more usually, identical to the framework regions of the human antibodies from which they were derived. In some embodiments, humanized antibodies of the disclosure include a variable region framework sequence selected from human antibody genes (e.g., germline antibody gene segments) which include one or more canonical CDR structure types that are identical or similar to the canonical CDR structure types for the corresponding non-human antibody (e.g., murine) which is humanized. See, U.S. Pat. No. 6,881,557 and Tan et al., *Journal of Immunol* 169:1119-1125 (2002) (incorporated by reference in their entirety for all purposes).

Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Framework residues can be analyzed to determine which, if any, residues should be substituted to optimize the properties of the resulting humanized antibody. For example, computer modeling can be used to identify residues which have a good probability of directly or indirectly influencing antigen binding.

Thus, in one embodiment the variable framework region of the humanized anti-ceramide antibody or antigen-binding fragment thereof shares at least 85% sequence identity to a human variable framework region sequence or consensus of such sequences. In some embodiments, the variable framework region of the humanized anti-ceramide antibody or antigen-binding fragment thereof shares at least 90%, preferably 95%, more preferably 96%, 97%, 98%, or 99% sequence identity to a human variable framework region sequence or consensus of such sequences.

In some embodiments, the humanized anti-ceramide antibody or antigen-binding fragment thereof exhibits a specific binding affinity for antigen of at least $10^7$ M$^{-1}$, $10^8$ M$^{-1}$, $10^9$ M$^{-1}$, or $10^{10}$ M$^{-1}$. Usually the upper limit of binding affinity of the humanized antibodies for antigen is within a factor of three, four, or five of that of the parental immunoglobulin. Often the lower limit of binding affinity is also within a factor of three, four, or five of that of the parent immunoglobulin. Alternatively, the binding affinity can be compared to that of a humanized antibody having no substitutions (e.g., an antibody having donor CDRs and acceptor FRs, but no FR substitutions). In such instances, the binding of the optimized antibody (with substitutions) is preferably at least two- to three-fold greater, or three- to four-fold greater, than that of the unsubstituted antibody. For making comparisons, activity of the various antibodies can be determined, for example, by BIACORE (i.e., surface plasmon resonance using unlabelled reagents) or competitive binding assays.

Methods of Treatment

The present application discloses a method of inhibiting cell death in a subject in need thereof, comprising administering to the subject a therapeutically effective amount of an anti-ceramide antibody or antigen-binding fragment thereof of the present disclosure. In some embodiments, the antibody or antigen-binding fragment thereof is a humanized scFv that specifically binds to ceramide.

In some embodiments, the cell death is associated with a disease selected from the group consisting of graft versus host disease, radiation disease, GI syndrome, and autoimmune disease. In some further embodiments, the disease is radiation disease or GI syndrome and the anti-ceramide antibody or antigen-binding fragment thereof is administered before the subject is exposed to radiation.

Radiation targets both the gastrointestinal microvasculature and intestinal stem cell compartments. Dysfunction of the microvascular endothelium, detected as apoptosis at four hours following radiation, represents a principle lesion leading to the GI syndrome. Endothelial dysfunction converts lesions to cycling crypt base columnar (CBC) cells from sublethal to lethal, resulting in loss of regenerative crypts and promoting GI toxicity. Immunohistochemical and labeling studies with [3H]TdR and BrdUrd revealed that crypt stem cell death does not occur acutely after radiation exposure. Rather, the earliest detectable response is a temporary dose-dependent delay in progression through a late S-phase checkpoint and mitotic arrest, apparently signaled by radiation-induced DNA double strand breaks (DSBs). A rapid apoptotic death occurs in growth arrested cells during the first 24 hours post irradiation that, at 12 Gy, equals 33% of the total death. In mammalian cells, DNA dsbs activate pathways of DNA damage recognition and repair, and a coordinated regulation of cell cycle checkpoint activity. The intestinal stem cell mitotic arrest appears to represent a regulated event in this pathway. A mitotic form of death occurs during this second 24 hours, representing 66% of overall death. No significant change in crypt number per intestinal circumference is apparent at this stage although crypt size progressively decreases due to continued normal migration of crypt transit and differentiated cells from the crypt into the epithelial lining of the villus and loss from the villus tip. Resumption of mitotic activity at 12-18 hours is associated with a rapid depletion of crypt stem cell clonogens and reduction in crypt number per circumference. Stem cell clonogen loss leads to a near total collapse of the crypt-villus system, mucosal denudation, and death from the GI syndrome.

Ceramide mediated raft clustering is involved in radiation-induced apoptosis and clonogenic cell death. It has long been accepted that the clonogenic compartment of the gastrointestinal (GI) mucosa is the specific and direct target for radiation in inducing GI damage.

The present disclosure is directed to a method for the mitigation of cell death in GI syndrome in a subject in need thereof. The method comprises the administration of an effective amount of an anti-ceramide antibody or antigen-binding fragment thereof. In some embodiments, the method comprises administering said anti-ceramide antibody or antigen-binding fragment thereof to said subject immediately after exposure of said subject to penetrating radiation. In other embodiments, the method comprises administering said anti-ceramide antibody or antigen-binding fragment thereof to said subject within one hour after exposure of said subject to penetrating radiation. In some embodiments, the method comprises administering said anti-ceramide antibody or antigen-binding fragment thereof to said subject within 2, 3, 4, 5, 6, 7, 8, 9, 10, 11, 12 or 18 hours after exposure of said subject to penetrating radiation. In some embodiments, the method comprises administering said anti-ceramide antibody or antigen-binding fragment thereof to said subject within 24 hours after exposure of said subject to penetrating radiation. In other embodiments, the method comprises administering said anti-ceramide antibody or antigen-binding fragment thereof to said subject within 30, 36, 42, 48, 54, 60, 66 or 72 hours after exposure of said subject to penetrating radiation. In other embodiments, the method comprises administering said anti-ceramide antibody or antigen-binding fragment thereof to said subject within 48, 36, 24, 18, 12, 10, 8, 6, 4, 2 or 1 hour(s), or within 45, 30 or 15 minutes before exposure of said subject to penetrating radiation.

In some embodiments, the disease is graft versus host disease and the anti-ceramide antibody or antigen-binding fragment thereof is administered before the subject receives a transplant. In some embodiments, the transplant is a bone marrow transplant. In other embodiments, the anti-ceramide antibody or antigen-binding fragment thereof is administered after the subject receives a transplant, but before the onset of graft versus host disease. In some embodiments, the anti-ceramide antibody or antigen-binding fragment thereof is administered to a subject in need thereof after the onset of graft versus host disease in an amount effective for the mitigation of apoptosis in graft versus host disease.

The disclosure also encompasses anti-ceramide antibodies and antigen-binding fragments thereof for the manufacture of a medicament for treatment of a disorder (e.g., GI syndrome or GvHD) characterized by expression of ceramide. In some embodiments, the protein or polypeptide comprises an anti-ceramide binding domain and inhibits formation of ceramide rich platforms. In some embodiments, the disclosure relates to a method for treating a disorder in a subject, wherein said disorder is characterized by expression of ceramide rich platforms, the method comprising administering to the subject a therapeutically effective amount of a protein or polypeptide of the present disclosure comprising a ceramide binding domain that specifically binds an epitope of human ceramide (e.g., ceramide-binding polypeptides).

In some embodiments, the disclosure provides a method of treating a patient with GI syndrome or GvHD, comprising administering to the patient an anti-ceramide antibody or antigen-binding fragment thereof comprising the amino acid sequence set forth herein (e.g., an amino acid sequence selected from the group consisting of SEQ ID NOs: 48-61). In some embodiments, the disclosure provides a method of treating a patient with GI syndrome or GvHD comprising administering the anti-ceramide antibody or antigen-binding fragment thereof of SEQ ID NO: 48 or 51.

In some embodiments, the anti-ceramide antibodies and antigen-binding fragments thereof prevent radiation-induced cell death or cell death associated with GvHD or autoimmune disease. Cell death can be measured by a variety of means known in the art including flow cytometry, immunofluorescence, and immunohistochemistry to assess changes in marker expression in dying cells, cell counts to assess viability, qPCR to assess changes in gene expression, and the like.

In some embodiments, the anti-ceramide antibodies and antigen-binding fragments thereof prevent cell death by inhibiting ceramide-rich platform formation. For example, in some embodiments, the anti-ceramide scFvs inhibit ceramide-rich platform formation in irradiated Jurkat T cells (See, Example 3 and FIG. 1). In some embodiments, the anti-ceramide antibody or antigen-binding fragment thereof reduces ceramide-rich platform formation by about 10%, about 20%, about 30%, about 40%, about 50%, about 60%, about 70%, about 75%, about 80%, about 85%, about 90%, about 95% or about 100%.

In some embodiments, the anti-ceramide antibodies and antigen-binding fragments thereof inhibit cell death. For example, in some embodiments, the anti-ceramide scFvs inhibit cell death in irradiated Jurkat T cells (See, Example 4 and FIGS. 2A-2D). In some embodiments, the anti-ceramide antibody or antigen-binding fragment thereof reduces cell death or apoptosis by about 10%, about 20%, about 30%, about 40%, about 50%, about 60%, about 70%, about 75%, about 80%, about 85%, about 90%, about 95% or about 100%.

In some embodiments, for treatment methods and uses described herein, the anti-ceramide antibody or antigen-binding fragment thereof is delivered in a manner consistent with conventional methodologies associated with management of the disease or disorder for which treatment is sought. In accordance with the disclosure herein, a therapeutically effective amount of the protein or polypeptide is administered to a subject in need of such treatment for a time and under conditions sufficient to prevent or treat the disease or disorder.

In prophylactic applications, pharmaceutical compositions or medicants comprising the anti-ceramide antibody or antigen-binding fragment thereof are administered to a patient susceptible to, or otherwise at risk of, a particular disorder in an amount sufficient to eliminate or reduce the risk or delay the onset of the disorder. In therapeutic applications, compositions or medicants comprising a protein of the present disclosure are administered to a patient suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents are usually administered in several dosages until a sufficient response (e.g., inhibition of inappropriate angiogenesis activity) has been achieved. Typically, the response is monitored and repeated dosages are given if the desired response starts to fade.

For administration, the anti-ceramide antibody or antigen-binding fragment thereof may be formulated as a pharmaceutical composition. A pharmaceutical composition may comprise: (i) a ceramide-binding polypeptide; and (ii) a pharmaceutically acceptable carrier, diluent or excipient. A pharmaceutical composition comprising a ceramide-binding polypeptide can be formulated according to known methods to prepare pharmaceutically useful compositions, whereby the therapeutic molecule is combined in a mixture with a pharmaceutically acceptable carrier, diluent, or excipient. A carrier is said to be a "pharmaceutically acceptable carrier" if its administration can be tolerated by a recipient patient. Sterile phosphate-buffered saline is one example of a pharmaceutically acceptable carrier. Other suitable carriers, diluents, or excipients are well-known to those in the art. (See, e.g., Gennaro (ed.), *Remington's Pharmaceutical Sciences* (Mack Publishing Company, 19th ed. 1995).) Formulations can further include one or more excipients, preservatives, solubilizers, buffering agents, albumin to prevent protein loss on vial surfaces, etc.

A pharmaceutical composition comprising a polypeptide or protein described herein may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. The oral unit dosage form may be selected from the group consisting of: tablets, pills, pellets, capsules, powders, lozenges, granules, solutions, suspensions, emulsions, syrups, elixirs, sustained-release formulations, aerosols, and sprays.

A pharmaceutical composition comprising the anti-ceramide antibody or antigen-binding fragment thereof may be administered to a subject in a therapeutically effective amount. According to the methods of the present disclosure, the anti-ceramide antibody or antigen-binding fragment thereof can be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, an agonist (e.g., ceramide-binding polypeptides) can be administered to a subject in a single bolus delivery, via continuous delivery (e.g., continuous transdermal delivery) over an extended time period, or in a repeated administration protocol (e.g., on an hourly, daily, weekly, or monthly basis).

Effective doses of the compositions of the present disclosure vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy.

Determination of effective dosages in this context is typically based on animal model studies followed up by human clinical trials and is guided by determining effective dosages and administration protocols that significantly reduce the occurrence or severity of the subject disorder in model subjects. Accordingly, a "therapeutically effective amount," as used herein, refers to an amount of a compound is an amount that achieves the desired biologic or therapeutic effect, namely an amount that prevents, reduces or ameliorates one or more symptoms of the enumerated diseases being treated or prevented. For example, the therapeutically effective amount of the antibody, or antigen-binding fragment thereof, will depend on the condition to be treated, the severity and course of the condition, whether the antibody is administered for preventive or therapeutic purposes, previous therapy, the patient's clinical history and response to the antibody, the type of antibody, or antigen-binding fragment thereof, used, and the discretion of the attending physician. The anti-ceramide antibody or antigen-binding fragment thereof is suitably administered to the patent at one time or over a series of treatments and may be administered to the patent at any time from diagnosis onwards. The anti-ceramide antibody or antigen-binding fragment thereof may be administered as the sole treatment or in conjunction with other drugs or therapies useful in treating the condition in question.

In some embodiments, the therapeutically effective amount of the anti-ceramide antibody or antigen-binding fragment thereof is between about 1 ng/kg body weight/day to about 100 mg/kg body weight/day. In some embodiments, the range of antibody administered is from about 1 ng/kg body weight/day to about 1 µg/kg body weight/day, 1 ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 µg/kg body weight/day, 1 µg/kg body weight/day to about 10 µg/kg body weight/day, 1 µg/kg body weight/day to about 100 µg/kg body weight/day, 10 µg/kg body weight/day to about 100 µg/kg body weight/day, 10 µg/kg body weight/day to about 1 mg/kg body weight/day, 100 µg/kg body weight/day to about 10 mg/kg body weight/day, 1 mg/kg body weight/day to about 100 mg/kg body weight/day and 10 mg/kg body weight/day to about 100 mg/kg body weight/day. Dosages within this range can be achieved by single or multiple administrations, including, e.g., multiple administrations per day or daily, weekly, bi-weekly, or monthly administrations. The anti-ceramide antibody or antigen-binding fragment thereof may be administered, as appropriate or indicated, as a single dose by bolus or by continuous infusion, or as multiple doses by bolus or by continuous infusion. Multiple doses may be administered, for example, multiple times per day, once daily, every 2, 3, 4, 5, 6 or 7 days, weekly, every 2, 3, 4, 5 or 6 weeks or monthly. However, other dosage regimens may be useful. The progress of this therapy is easily monitored by conventional techniques.

For administration to a human adult patient, the therapeutically effective amount may be administered in doses in the range of 0.0006 mg to 1000 mg per dose, including but not limited to 0.0006 mg per dose, 0.001 mg per dose, 0.003 mg per dose, 0.006 mg per dose, 0.01 mg per dose, 0.03 mg per dose, 0.06 mg per dose, 0.1 mg per dose, 0.3 mg per dose, 0.6 mg per dose, 1 mg per dose, 3 mg per dose, 6 mg per dose, 10 mg per dose, 30 mg per dose, 60 mg per dose, 100 mg per dose, 300 mg per dose, 600 mg per dose and 1000 mg per dose, and multiple, usually consecutive daily doses may be administered in a course of treatment. The anti-ceramide antibody or antigen-fragment thereof can be administered at different times of the day. In one embodiment the optimal therapeutic dose can be administered in the evening. In another embodiment the optimal therapeutic dose can be administered in the morning. As expected, the dosage will be dependent on the condition, size, age, and condition of the patient.

Dosage of the pharmaceutical composition comprising the anti-ceramide antibody or antigen-binding fragment thereof can be varied by the attending clinician to maintain a desired concentration at a target site. For example, if an intravenous mode of delivery is selected, local concentration of the agent in the bloodstream at the target tissue can be between about 0.01-50 nM, sometimes between about 1.0 nM and 10, 15, or 25 nM depending on the subject's status and projected measured response. Higher or lower concentrations can be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, trans-dermal formulations, etc. To achieve the same serum concentration level, for example, slow-release particles with a release rate of 5 nM (under standard conditions) would be administered at about twice the dosage of particles with a release rate of 10 nM.

Pharmaceutical compositions comprising the anti-ceramide antibody or antigen-binding fragment thereof can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

EXAMPLES

The present disclosure is further illustrated by the following examples which should not be construed as limiting. The contents of all references, patents and published patent applications cited throughout this application, as well as the Figures and Tables, are incorporated herein by reference.

Example 1: 6B5 Antibody Humanization and Production

The goal of the current study was to maximize the amount of human sequence in the humanized ceramide antibodies while retaining the original specificity of the 6B5 mouse antibody.

Antibody humanization design: Humanization design of the parental 6B5 mouse antibody) was performed using in silico analysis. Briefly, a 3D structure of the parental 6B5 antibody was generated using homology modeling and a profile of the parental antibody was created based on the 3D model. Two human heavy chain (HC) and two human light chain (LC) acceptor frameworks were selected based on overall sequence identity across the framework, matching interface position, similarly classed CDR canonical positions, and the presence of N-glycosylation sites. Humanized antibodies were then designed by creating multiple hybrid sequences that fused select parts of the parental antibody sequence with the human framework sequences. Using the 3D structure of the parental 6B5 antibody, these humanized sequences were methodically analyzed by eye and computer modeling to isolate the sequences that would most likely retain antigen binding. Three humanized HCs were designed based on the two different human HC acceptor frameworks and three humanized LCs were designed based on the two different human LC acceptor frameworks. The framework combinations are shown below in Table 6.

TABLE 6

| Acceptor frameworks for humanized 6B5 antibodies | |
| --- | --- |
| Chain Name | Human Acceptor Framework |
| VH1 + VL1 | HC framework 1/LC framework 1 |
| VH1 + VL2 | HC framework 1/LC framework 1 |
| VH1 + VL3 | HC framework 1/LC framework 2 |
| VH2 + VL1 | HC framework 1/LC framework 1 |
| VH2 + VL2 | HC framework 1/LC framework 1 |
| VH2 + VL3 | HC framework 1/LC framework 2 |
| VH3 + VL1 | HC framework 2/LC framework 1 |
| VH3 + VL2 | HC framework 2/LC framework 1 |
| VH3 + VL3 | HC framework 2/LC framework 2 |

Humanized VH1 and VL1 utilize the first respective framework and contain the most human sequence with minimal parental antibody framework sequence. VH2 and VL2 use the same framework as VH1 and VL1 but contain additional parental sequences. VH3 and VL3 utilize the second respective framework and similar to humanized VH2 and VL2, also contain additional parental sequences fused with the human framework.

The humanized heavy and light chains described above were combined to create fully humanized antibodies. The combinations of humanized heavy and light chains were tested for their expression level and antigen binding affinity to identify antibodies that perform similarly to the parental 6B5 mouse antibody.

Calculation of humanness scores of engineered antibodies: A tool was developed to calculate the humanness scores of engineered humanized antibodies (Gao et. al., BMC Biotechnology 2013, 13:55). The T20 score represents the degree of antibody humanness by analyzing the primary sequences of the variable regions. The T20 scores for the murine 6B5 and humanized 6B5 heavy and light chains are shown in Table 7 and 8 below.

TABLE 7

| Humanness scores of Humanized 6B5 VH Chains | | |
| --- | --- | --- |
| VH | Framework only Humanness | Framework + CDR Humanness |
| Murine 6B5 VH | 69 | 62 |
| Humanized VH1 | 90 | 82 |

TABLE 7-continued

| Humanness scores of Humanized 6B5 VH Chains | | |
| --- | --- | --- |
| VH | Framework only Humanness | Framework + CDR Humanness |
| Humanized VH2 | 87 | 78 |
| Humanized VH3 | 85 | 75 |

TABLE 8

| Humanness scores of Humanized 6B5 VL Chains | | |
| --- | --- | --- |
| VL | Framework only Humanness | Framework + CDR Humanness |
| Murine 6B5 VL | 79 | 76 |
| Humanized VL1 | 96 | 89 |
| Humanized VL2 | 93 | 86 |
| Humanized VL3 | 95 | 87 |

For full-length HCs, a score of 79 or above is indicative of a human-like heavy chain and for full-length kappa LCs, a score of 86 or above is indicative of a human-like light chain. As shown in Tables 7 and 8, the humanness scores of full-length VH1, VL1, VL2, and VL3 signified that these chains were human-like.

The T20 scores for the full-length antibodies are significantly influenced by the low humanness of the CDR regions from the mouse 6B5 antibody, which are generally kept untouched during humanization. Thus, the T20 scores for the framework only region, i.e., without the murine CDR sequences, was also calculated for the humanized antibodies. For HC frameworks, a score of 84 or above is indicative of human-like heavy chain and for kappa LC frameworks, a score of 90 or above is indicative of human-like light chain. As shown in Tables 7 and 8, the humanness scores of the 6B5 heavy and light chains (framework only) signified that the VH and VL regions were human-like.

Construction and small-scale production of humanized scFvs: The humanized VH and VL chains described above were reformatted into scFvs with octa-His tags at the C-terminus (SEQ ID NO: 76). The murine parental 6B5 scFv was expressed in parallel for comparison. For antibody production, plasmids for the indicated scFvs were transformed into BL21(DE3) E. coli, and scFvs were then purified from lysed cells using His-tag affinity purification columns.

Example 2: Production and Analysis of a Humanized Anti-Ceramide scFv

Expression of antibody constructs: The nucleotide sequences of the anti-ceramide VH2 and VL1 were cloned into a high expression mammalian vector (Lake Pharma) and nucleic acid sequences of the cloned constructs were verified. Each construct was then scaled up to the appropriate amount for transfection and quality of the plasmid DNA was assessed by gel electrophoresis.

CHO cells were seeded in a shake flask and expanded using serum-free chemically defined medium. On the day of transfection, the expanded cells were seeded into a new flask with fresh medium, and each antibody-expression construct was transiently transfected into CHO cells using standard procedures known in the art. The cells were maintained as a batch-fed culture (C4611 and C4612, Medna) until the end of production. The conditioned media from the transient transfection was harvested and clarified by centrifugation and filtration. Antibodies were then purified by Protein L or IMAC purification as described below.

Protein L Affinity Purification: The supernatant was loaded over a Protein L column pre-equilibrated with binding buffer. Washing buffer was passed through the column until the OD280 value (NanoDrop™, Thermo Scientific™) was zero. The target protein was eluted with a low pH buffer, fractions were collected, and the OD280 value of each fraction was recorded. Fractions containing the target protein were pooled and filtered through a 0.2 μm membrane. The protein concentration was calculated from the OD280 value and the calculated extinction coefficient.

IMAC Purification of His-tagged Protein: The supernatant was loaded over an Immobilized Metal (Nickel) Affinity Chromatography (IMAC) column pre-equilibrated with binding buffer. Washing buffer containing 40 mM imidazole was passed through the column until the OD280 value (NanoDrop™, Thermo Scientific™) was close to zero. The target protein was eluted with a linear gradient of increasing imidazole concentration up to 0.5 M. The eluate was collected in fractions and the OD280 value of each fraction was recorded. CE-SDS (LabChip® GXII, Perkin Elmer) of each fraction was performed and analyzed. Fractions containing the target protein were pooled and dialyzed into the client specified buffer. The protein was filtered through a 0.2 μm membrane and protein concentration was calculated from the OD280 value (NanoDrop™, Thermo Scientific™) and the calculated extinction coefficient.

Antibody analysis: Size exclusion chromatography (SEC) was performed using a HiLoad 26/600 Superdex 200 column (GE Healthcare Life Sciences). Collected fractions were analyzed by CE-SDS (LabChip® GXII, Perkin Elmer). Fractions containing the target protein were pooled and analyzed by SE-UPLC. A summary of the analysis report for antibody construct 2766 using each purification method is shown in Table 9.

TABLE 9

| Purification of the 2766 6B5 antibody | | | |
| --- | --- | --- | --- |
| Antibody | Purification method | Concentration (mg/mL) | Total yield (mg) |
| 2766 | IMAC | 0.77 | 32.34 |
| 2766 | Protein L | 0.60 | 35.52 |

Example 3: Humanized 6B5 scFvs Inhibit Formation of Ceramide-Rich Platforms In Vitro The humanized anti-ceramide scFvs produced in Example 1 and 2 were then tested for their ability to inhibit formation of ceramide-rich platforms.

For cell culture and stimulation, Jurkat T lymphocyte (clone E6-1, TIB-152, ATCC) were maintained in RPMI 1640 media supplemented with 10% heat inactivated FBS in a humidified incubator at 37° C. with 5% $CO_2$. Cells were washed and resuspended in RPMI 1640 media supplemented with 1% FBS or delipidated FBS. Briefly, cells were counted on a hemocytometer and $1 \times 10^6$ cells per 0.5 ml were plated in a 24 well plate at 37° C. After 2 h, cells were stimulated with 0.6 μg/ml human anti-CD28 antibody (AF-342-PB, R&D systems). In addition, Jurkat T lymphocytes were pre-treated with 50 ng/mL to 800 ng/mL of humanized 6B5 scFvs for 1 hour prior to stimulation with anti-CD28 antibody (0.6 μg/mL, Cat. No. AF-342-PB, R&D Systems) for 45 seconds. Cells were then immediately fixed with 4% paraformaldehyde for 10 min at 4° C.

Ceramide-rich platforms (CRPs) were detected as described previously (J. A. Rotolo et al., 2005; Stancevic et al., 2013). Non-specific sites were blocked by incubating cells with 2% normal donkey serum (D9663, Sigma) for 2 h on ice. Following a PBS wash, cells were stained for surface ceramide using mouse anti-ceramide 1° Ab MID 15B4 IgM (1:50, Alexis Biochemicals) overnight at 4° C. Irrelevant mouse IgM was used as isotype control. Cells were then washed 3× with PBST and stained with Cy3-conjugated anti-mouse IgM 2° Ab (1:400, Jackson Immu-noResearch) for 1 h at 4° C. Cells were washed 3× with PBST and mounted on glass slides using Vectashield® fluorescent mounting media containing DAPI (Vector Laboratories). Platforms were imaged on Leica SP5 Inverted microscope with HyD hybrid detector photon counter and HCX PL APO CS 63.0×1.40 oil objective lens with digital zoom at 7 for volumetric analysis and HCX PL APO CS 40.0×1.25 oil objective lens with digital zoom 1 for inci-dence analysis at room temperature. Z-stacks were acquired using Leica LAS AF software.

3-dimensional CRP volumetric analysis was conducted created using Imaris software (Bitplane AG, Zurich, Swit-zerland). Briefly, 10-12 individual Z-stacks for each sample were acquired under optimized conditions, and data were transported to Imaris software. Intensity normalization was performed for control and treated samples. Briefly, intensity mean threshold for z-column was obtained from untreated control samples. Based on intensity mean threshold, surfaces were created in for untreated control, CD28-treated and scFv-treated cells using the "Surfaces" feature in Imaris. Intensity mean threshold allows only a certain range of intensity values to be considered as positive value for surface volume quantitation, while anything outside this range is considered negative. Volume for each surface is generated by surface volume function of Imaris. Individual volume for each sample set is summed up and mean calcu-lated for final analysis. To calculate IC50 values, inhibitory effects of each antibody were normalized to a scale of 0-100% CRP inhibition, where 0% represents untreated control (CD28 antibody alone) and 100% represents anti-body treatment that achieved the best inhibitory effect. Data were plotted using Graph Pad Prism 8 and curves fitted using nonlinear regression analysis.

As shown in FIG. 1, pre-incubation with different con-centrations of 6B5 scFvs inhibited CRP formation in CD28-activated T cells. VH2-VL1 was the most effective at preventing CRP formation with an $IC_{50}$ value of 6.1 ng/mL. The $IC_{50}$ values for the various humanized 6B5 scFvs tested are shown in Table 10 below.

TABLE 10

| Inhibition of CRP formation with humanized 6B5 scFvs | | |
| --- | --- | --- |
| Humanized 6B5 scFv | SEQ ID NO | $IC_{50}$ (ng/mL) |
| VH1-VL1 | 54 | 180.8 |
| VH1-VL3 | 56 | 85.7 |
| VH2-VL1 | 51 | 6.1 |
| VH2-VL2 | 57 | 12.1 |
| VH3-VL1 | 59 | 12.7 |
| VH3-VL2 | 60 | 8.4 |

Example 4: Humanized 6B5 scFvs Inhibit Radiation-Induced Apoptosis In Vitro

The humanized anti-ceramide scFvs produced in Example 1 and 2 were then tested for their ability to inhibit radiation-induced cell death.

Figure 2A:
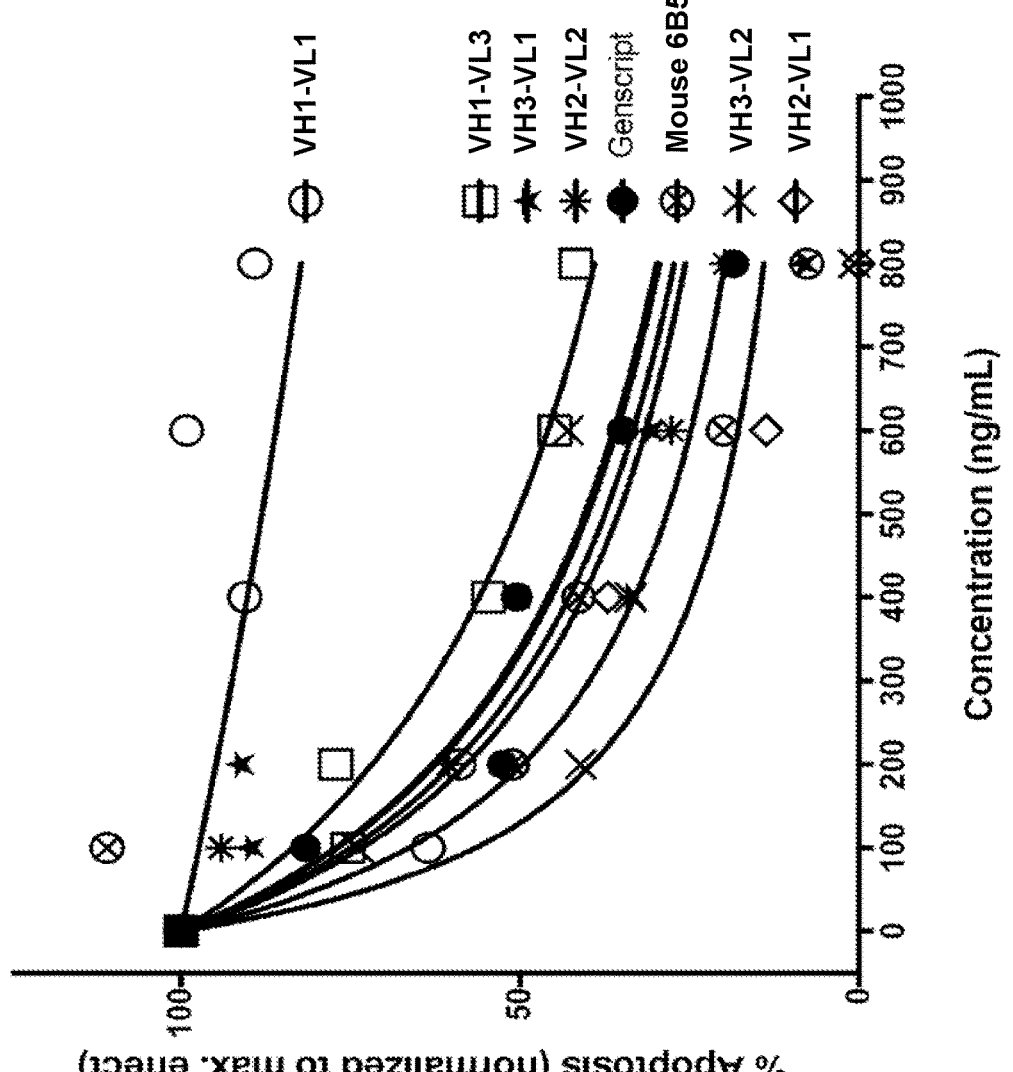
FIG. 2A shows a dose-response curve of radiation-induced T cell apoptosis with increasing concentrations of humanized 6B5 scFvs.

Apoptosis assay was performed as described (Haimovitz-Friedman et al., 1994; J. A. Rotolo et al., 2005). Jurkat T lymphocytes were resuspended in RPMI 1640 supplemented with 1% FBS and pre-treated with 100 ng/mL, 200 ng/mL, 400 ng/mL, 600 ng/mL, or 800 ng/mL of humanized 6B5 scFvs for 1 hour at 37° C. before exposure to 10 Gy (~1.5 Gy/minute) of radiation. Irradiated Jurkat T cells were incubated at 37° C. for 16 hours and then fixed in 4% paraformaldehyde. Cells were then washed with PBS, stained with 24 μg/ml of the fluorophore bisbenzimide trihydrochloride (Hoechst 33258; SIGMA-ALDRICH®), and placed on glass slides for counting on an Olympus® IMT-2 microscope using a 40× DPlanApo40UV 0.850160/ 0.11-0.23 objective lens at room temperature. Using a fluo-rescence microscope, apoptosis was quantified based on morphologic characteristics of apoptotic nuclei including chromatin condensation, segmentation, and compaction along with nuclear periphery and the appearance of apop-totic bodies, A minimum of 100 cells was counted per sample. Percent inhibition of apoptosis was determined by normalizing values to the radiation only control (FIG. 2A). $IC_{50}$ values were calculated using non-linear regression on GraphPad Prism v7 software.

As shown in FIG. 2A, pre-incubation with different concentrations of 6B5 scFvs inhibited apoptosis in irradiated Jurkat T cells. VH2-VL1 was the most effective at inhibiting radiation-induced apoptosis with an $IC_{50}$ value of 130.3 ng/mL. The $IC_{50}$ values for the various humanized 6B5 scFvs tested are shown in Table 11 below.

TABLE 11

| Inhibition of T cell apoptosis with humanized 6B5 scFvs | | |
| --- | --- | --- |
| 6B5 scFv | SEQ ID NO | $IC_{50}$ (ng/mL) |
| VH1-VL1 | 54 | 3707 |
| VH1-VL3 | 56 | 509.9 |
| VH2-VL1 | 51 | 130.3 |
| VH2-VL2 | 57 | 332.7 |
| VH3-VL1 | 59 | 339.8 |
| VH3-VL2 | 60 | 197.6 |
| Murine 6B5 antibody | 62 | 274.8 |
| Genscript | | 299.2 |

Figure 2B:
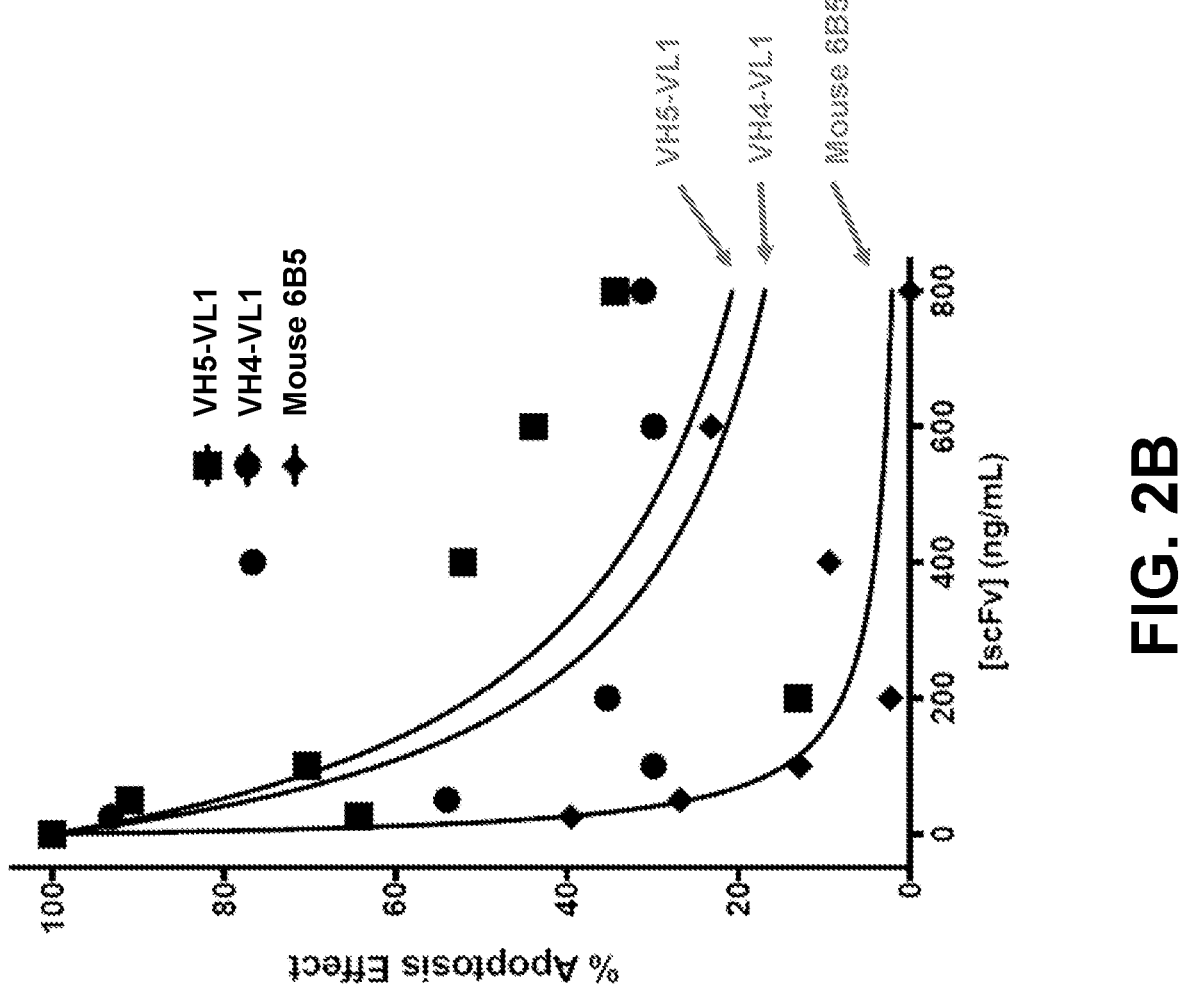
FIG. 2B shows a dose-response curve of radiation-induced T cell apoptosis with increasing concentrations of VH4-VL1, VH5-VL1, and parental murine 6B5 scFv.
Figure 2C:
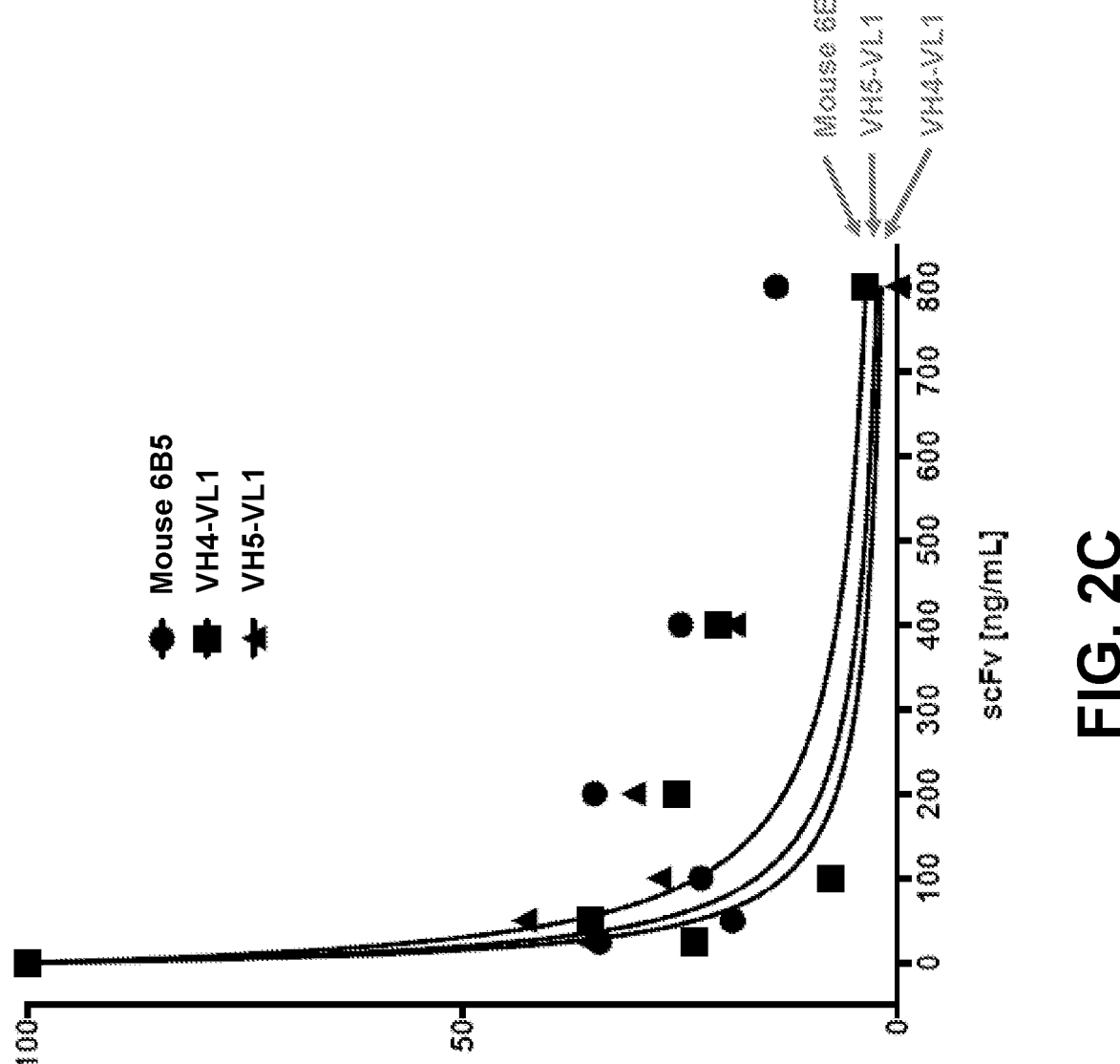
FIG. 2C shows a dose-response curve of radiation-induced T cell apoptosis with increasing concentrations of VH4-VL1, VH5-VL1, and parental murine 6B5 scFv.
Figure 2D:
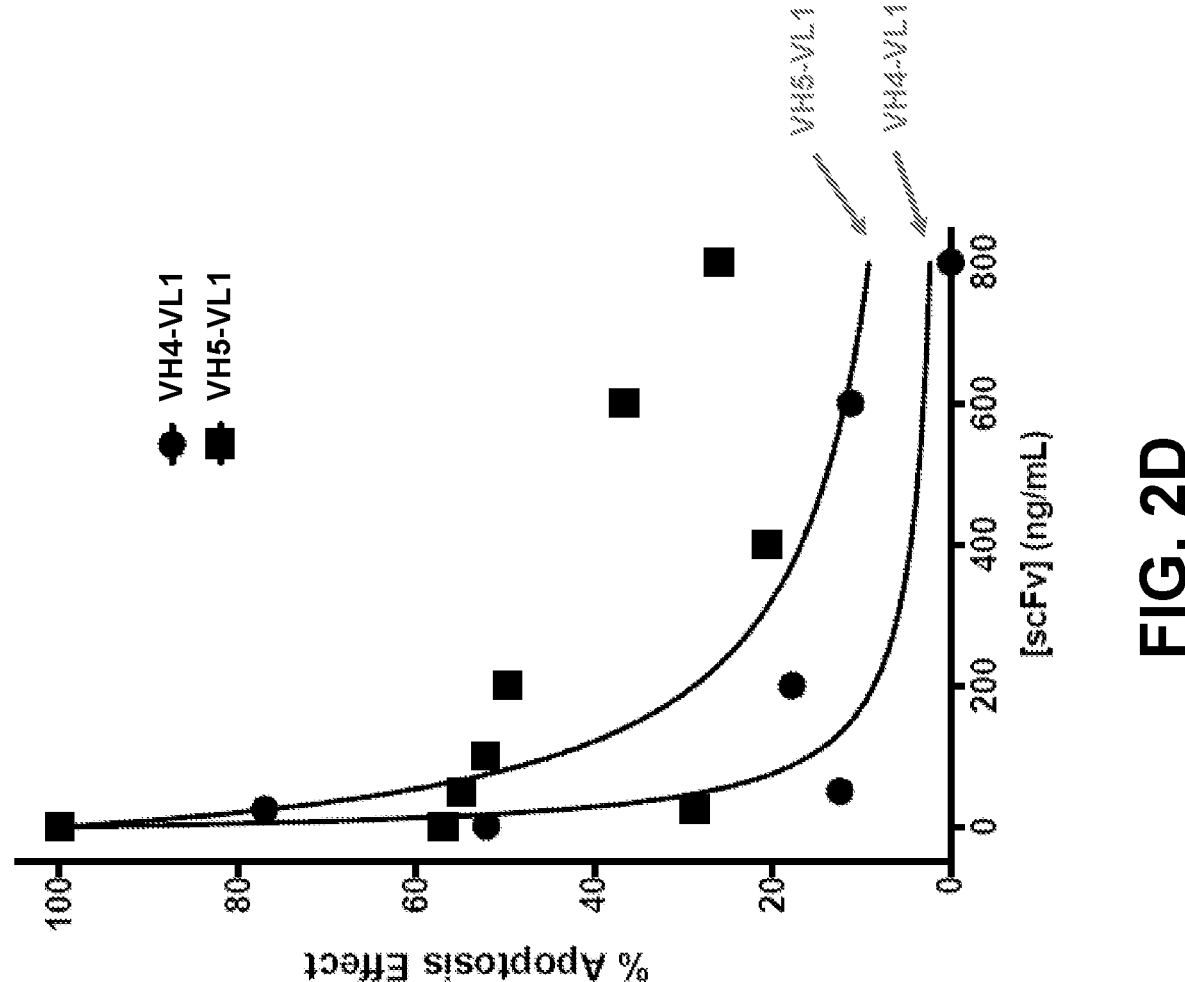
FIG. 2D shows a dose-response curve of radiation-induced T cell apoptosis with increasing concentrations of VH4-VL1 and VH5-VL1.

Two additional humanized 6B5 scFvs, VH4-VL1 (SEQ ID NO: 52) and VH5-VL1 (SEQ ID NO: 53) were tested for their ability to inhibit radiation-induced T cell apoptosis using a similar experimental setup (FIGS. 2B-2E). In FIG. 2B, each of VH4-VL1, VH5-VL1, and parental murine 6B5 scFv was incubated with Jurkat T cells at 25 ng/mL, 50 ng/mL, 100 ng/mL, 200 ng/mL, 400 ng/mL, 600 ng/mL or 800 ng/mL for 1 hour, and the ability of each scFv to inhibit radiation-induced apoptosis was normalized to the protec-tive effect of parental murine 6B5 scFv at 800 ng/mL. In FIG. 2C, each of VH4-VL1, VH5-VL1, and parental murine 6B5 scFv was incubated with Jurkat T cells at 25 ng/mL, 50 ng/mL, 100 ng/mL, 200 ng/mL, 400 ng/mL, or 800 ng/mL for 1 hour, and the ability of each scFv to inhibit radiation-induced apoptosis was normalized to the protective effect of VH5-VL1 at 800 ng/mL. In FIG. 2D, VH4-VL1 and VH5-VL1 was incubated with Jurkat T cells at 25 ng/mL, 50 ng/mL, 100 ng/mL, 200 ng/mL, 400 ng/mL, 600 ng/mL or 800 ng/mL for 1 hour, and the ability of each construct to inhibit radiation-induced apoptosis was normalized to the protective effector to the protective effect of VH4-VL1 at 800 ng/mL. $IC_{50}$ values based on these sets of experiments are provided below in Table 12.

TABLE 12

| | | | |
|---|---|---|---|
| Inhibition of T cell apoptosis with humanized 6B5 scFvs | | | |
| 6B5 scFv | SEQ ID NO | $IC_{50}$ (ng/mL) | Corresponding FIG. |
| Parental murine 6B5 scFv | 62 | 19.4 | FIG. 2C |
| VH4-VL1 | 52 | 15.1 | FIG. 2C |
| VH5-VL1 | 53 | 30.0 | FIG. 2C |
| VH4-VL1 | 52 | 18.9 | FIG. 2D |
| VH5-VL1 | 53 | 80.7 | FIG. 2D |

Figure 2E:
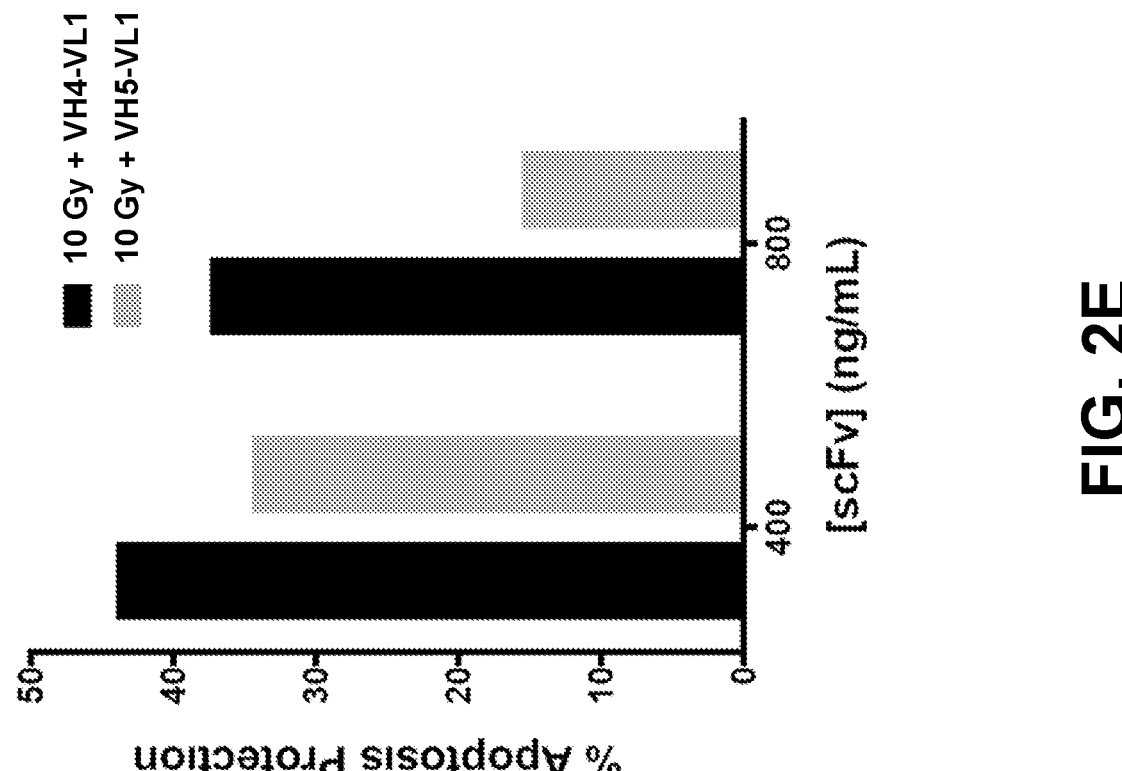
FIG. 2E shows the percentage of radiation-induced apoptotic T cells with given concentrations of VH4-VL1 and VH5-VL1.

FIG. 2E shows the protective effect of VH4-VL1 and VH5-VL1 at given concentrations (400 ng/mL and 800 ng/mL) as evaluated by the percentage of radiation-induced apoptotic T cells under these conditions. Overall, these results demonstrate that humanized 6B5 scFvs can effectively protect T cells against radiation induced apoptosis.

Example 5: Treatment with Humanized 6B5 scFv Prevents Radiation-Induced Cell Death In Vivo Anti-ceramide VH2-VL1 (SEQ ID NO: 51) was tested in vivo for treatment in mice exposed to lethal doses of radiation. A $LD_{90}$ dose of 15 gray units (Gy) was delivered to C57BL/6 mice using a cesium irradiator and mice were left either untreated or intravenously treated with 6B5 VH2-VL1 (150 µg/25 g) 24 hours following irradiation. Mice were euthanized at different time points following irradiation and sequential segments of proximal jejunum from the ligament of Treitz were isolated, fixed in 4% paraformaldehyde, and embedded in paraffin. Tissue was sectioned at 5 µm and apoptotic endothelial cells were identified using lethal the Terminal deoxynucleotidyl transferase dUTP Nick-End Labeling (TUNEL) assay with MECA-32 antibody (pan-endothelial cell marker). Double-stained apoptotic endothelial cells were quantified.

Figure 3A:
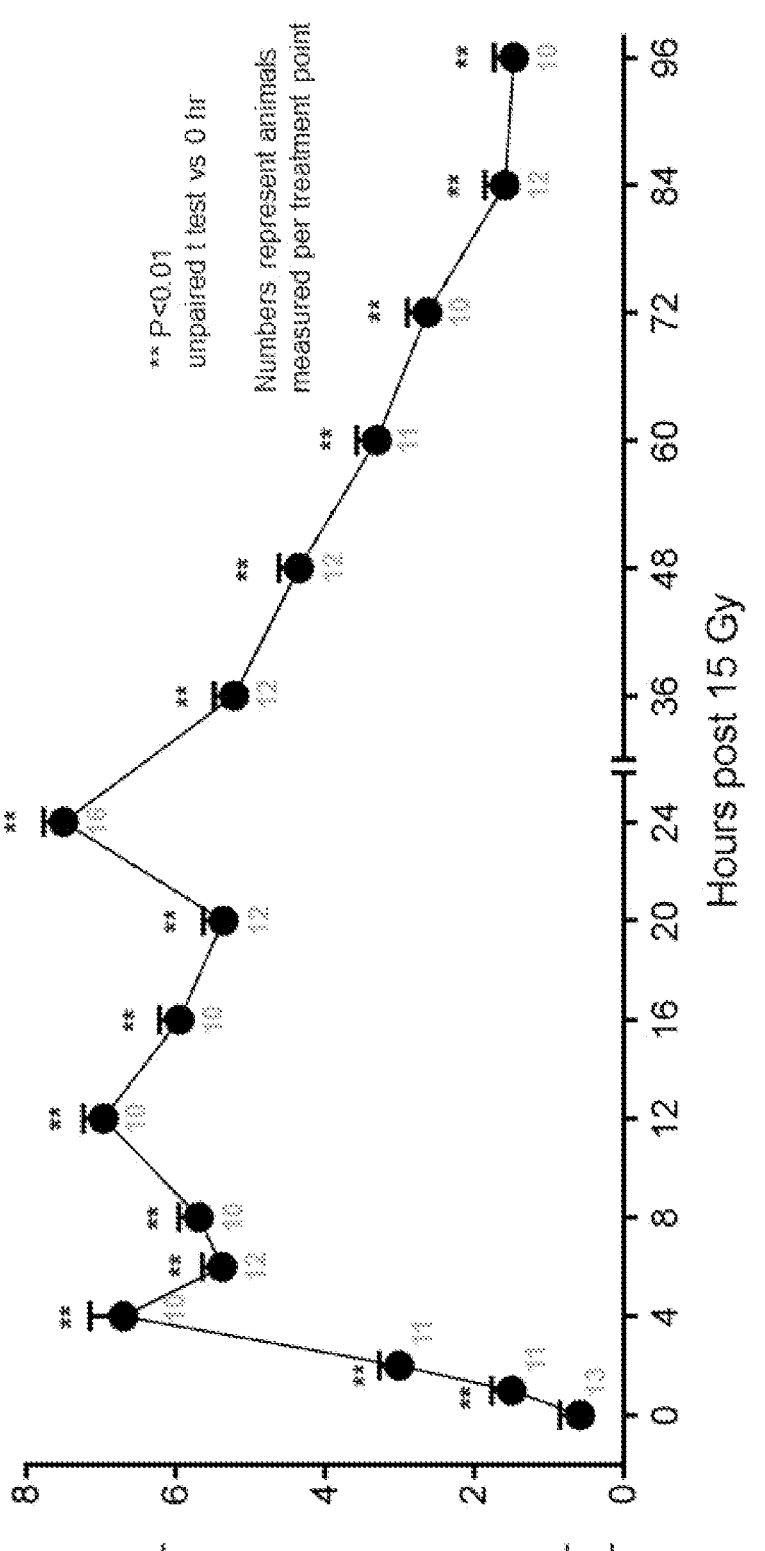
FIG. 3A shows the number of apoptotic endothelial cells per villus over time in mice exposed to an $LD_{90}$ dose of 15 gray units (Gy). The numbers adjacent to the symbols represent the number of animals measured per time point. Gy, gray unit of absorbed radiation.
Figure 3B:
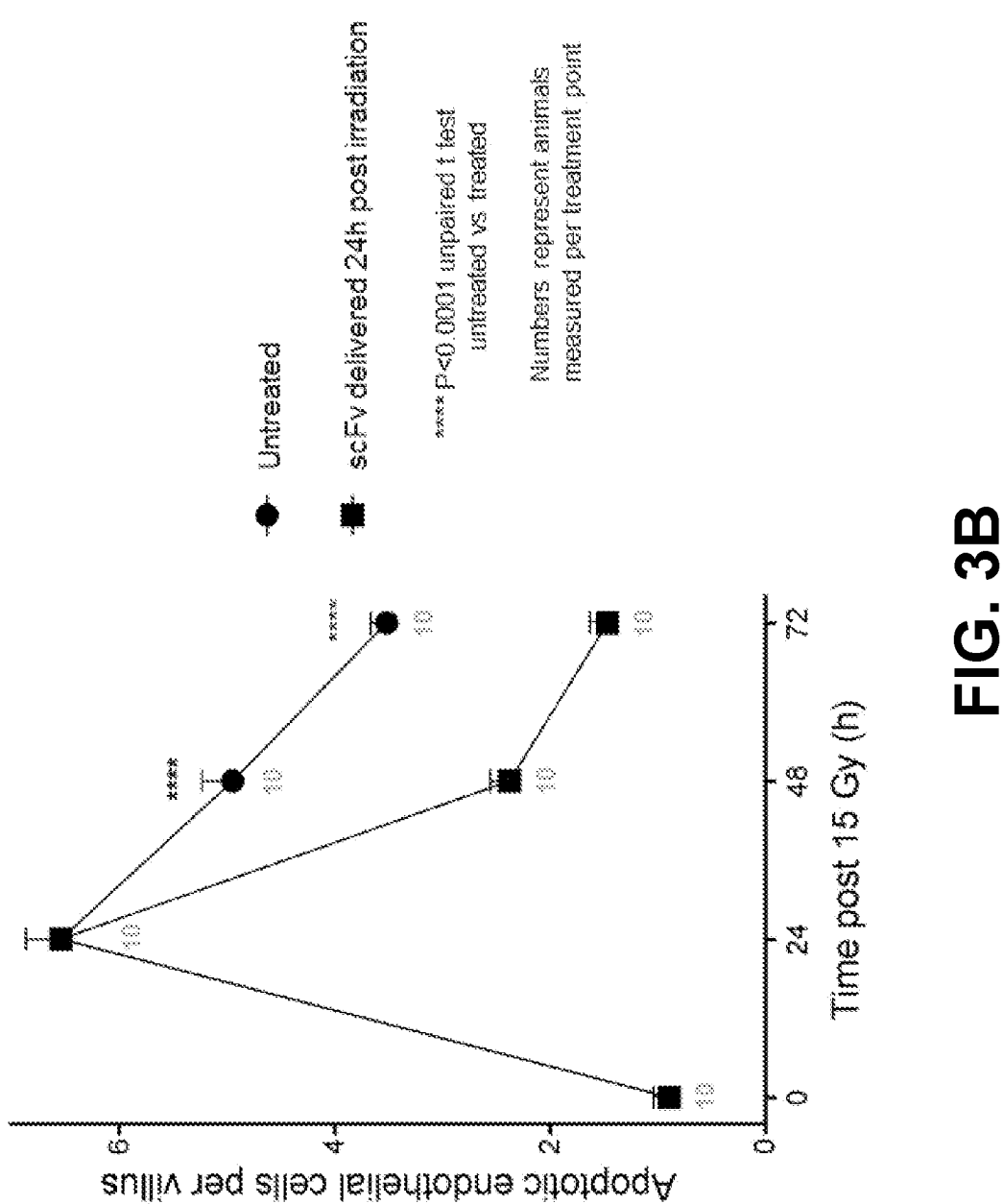
FIG. 3B shows the number of apoptotic endothelial cells per villus over time in mice exposed to an $LD_{90}$ dose of 15 gray units (Gy) and left untreated or treated with VH2-VL1 (SEQ ID NO: 51) 24 hours following irradiation. The numbers adjacent to the symbols represent the number of animals measured per time point. Gy, gray unit of absorbed radiation.

Mice irradiated with an $LD_{90}$ dose of 15 Gy resulted in cell death of the small intestinal endothelium, which peaked 24 hours following irradiation (FIG. 3A). Treatment with 6B5 VH2-VL1 24 hours after irradiation significantly reduced endothelial cell apoptosis compared to untreated mice (FIG. 3B). Overall, these data indicate that inhibiting ceramide prevents endothelial cell death in the gastrointestinal tract in a mouse model of GI syndrome. Humanized anti-ceramide scFvs may be beneficial for the treatment of diseases associated with increased cell death, including GI syndrome, GvHD, and autoimmunity.

FURTHER NUMBERED EMBODIMENTS

Further embodiments of the instant disclosure are provided in the numbered embodiments below:

Embodiment 1. An anti-ceramide antibody or antigen-binding fragment thereof comprising an immunoglobulin heavy chain variable region (VH) comprising a heavy chain complementarity determining region (CDR) 1 (HCDR1), a heavy chain CDR2 (HCDR2), and a heavy chain CDR3 (HCDR3), and an immunoglobulin light chain variable region (VL) comprising a light chain complementarity determining region (CDR) 1 (LCDR1), a light chain CDR2 (LCDR2), and a light chain CDR3 (LCDR3), wherein: (a) the HCDR1 comprises an amino acid sequence selected from SEQ ID NO: 1 and 2; (b) the HCDR2 comprises an amino acid sequence selected from SEQ ID NO: 3, 4, 5, and 6; (c) the HCDR3 comprises the amino acid sequence of SEQ ID NO: 7; (d) the LCDR1 comprises the amino acid sequence of SEQ ID NO: 8; (e) the LCDR2 comprises the amino acid sequence of SEQ ID NO: 9; and (f) the LCDR3 comprises the amino acid sequence of SEQ ID NO: 10.

Embodiment 2. The anti-ceramide antibody or antigen-binding fragment thereof of Embodiment 1, wherein the HCDR1 comprises SEQ ID NO: 1 and the HCDR2 comprises SEQ ID NO: 3.

Embodiment 3. The anti-ceramide antibody or antigen-binding fragment thereof of Embodiment 1, wherein the HCDR1 comprises SEQ ID NO: 1 and the HCDR2 comprises SEQ ID NO: 4.

Embodiment 4. The anti-ceramide antibody or antigen-binding fragment thereof of Embodiment 1, wherein the HCDR1 comprises SEQ ID NO: 1 and the HCDR2 comprises SEQ ID NO: 5.

Embodiment 5. The anti-ceramide antibody or antigen-binding fragment thereof of Embodiment 1, wherein the HCDR1 comprises SEQ ID NO: 1 and the HCDR2 comprises SEQ ID NO: 6.

Embodiment 6. The anti-ceramide antibody or antigen-binding fragment thereof of Embodiment 1, wherein the HCDR1 comprises SEQ ID NO: 2 and the HCDR2 comprises SEQ ID NO: 3.

Embodiment 7. The anti-ceramide antibody or antigen-binding fragment thereof of Embodiment 1, wherein the HCDR1 comprises SEQ ID NO: 2 and the HCDR2 comprises SEQ ID NO: 4.

Embodiment 8. The anti-ceramide antibody or antigen-binding fragment thereof of Embodiment 1, wherein the HCDR1 comprises SEQ ID NO: 2 and the HCDR2 comprises SEQ ID NO: 5.

Embodiment 9. The anti-ceramide antibody or antigen-binding fragment thereof of Embodiment 1, wherein the HCDR1 comprises SEQ ID NO: 2 and the HCDR2 comprises SEQ ID NO: 6.

Embodiment 10. The anti-ceramide antibody or antigen-binding fragment thereof of Embodiment 1, wherein the VH comprises an amino acid sequence that is at least 90%, at least 95%, or at least 97% identical to SEQ ID NO: 17 and the VL comprises an amino acid sequence that is at least 90%, at least 95%, or at least 97% identical to SEQ ID NO: 22.

Embodiment 11. The anti-ceramide antibody or antigen-binding fragment thereof of Embodiment 10, wherein the VH comprises an amino acid sequence that is 100% identical to SEQ ID NO: 17 and the VL comprises an amino acid sequence that is 100% identical to SEQ ID NO: 22.

Embodiment 12. The anti-ceramide antibody or antigen-binding fragment thereof of Embodiment 10, wherein the VH amino acid sequence consists of SEQ ID NO: 17 and the VL amino acid sequence consists of SEQ ID NO: 22.

Embodiment 13. The anti-ceramide antibody or antigen-binding fragment thereof of Embodiment 1, wherein the VH comprises an amino acid sequence that is at least 90%, at least 95%, or at least 97% identical to SEQ ID NO: 17 and the VL comprises an amino acid sequence that is at least 90%, at least 95%, or at least 97% identical to SEQ ID NO: 23.

Embodiment 14. The anti-ceramide antibody or antigen-binding fragment thereof of Embodiment 13, wherein the VH comprises an amino acid sequence that is 100% identical to SEQ ID NO: 17 and the VL comprises an amino acid sequence that is 100% identical to SEQ ID NO: 23.

Embodiment 15. The anti-ceramide antibody or antigen-binding fragment thereof of Embodiment 13, wherein the VH amino acid sequence consists of SEQ ID NO: 17 and the VL amino acid sequence consists of SEQ ID NO: 23.

Embodiment 16. The anti-ceramide antibody or antigen-binding fragment thereof of Embodiment 1, wherein the VH comprises an amino acid sequence that is at least 90%, at least 95%, or at least 97% identical to SEQ ID NO: 17 and the VL comprises an amino acid sequence that is at least 90%, at least 95%, or at least 97% identical to SEQ ID NO: 24.

Embodiment 17. The anti-ceramide antibody or antigen-binding fragment thereof of Embodiment 16, wherein the VH comprises an amino acid sequence that is 100% identical to SEQ ID NO: 17 and the VL comprises an amino acid sequence that is 100% identical to SEQ ID NO: 24.

Embodiment 18. The anti-ceramide antibody or antigen-binding fragment thereof of Embodiment 16, wherein the VH amino acid sequence consists of SEQ ID NO: 17 and the VL amino acid sequence consists of SEQ ID NO: 24.

Embodiment 19. The anti-ceramide antibody or antigen-binding fragment thereof of Embodiment 1, wherein the VH comprises an amino acid sequence that is at least 90%, at least 95%, or at least 97% identical to SEQ ID NO: 18 and the VL comprises an amino acid sequence that is at least 90%, at least 95%, or at least 97% identical to SEQ ID NO: 22.

Embodiment 20. The anti-ceramide antibody or antigen-binding fragment thereof of Embodiment 19, wherein the VH comprises an amino acid sequence that is 100% identical to SEQ ID NO: 18 and the VL comprises an amino acid sequence that is 100% identical to SEQ ID NO: 22.

Embodiment 21. The anti-ceramide antibody or antigen-binding fragment thereof of Embodiment 19, wherein the VH amino acid sequence consists of SEQ ID NO: 18 and the VL amino acid sequence consists of SEQ ID NO: 22.

Embodiment 22. The anti-ceramide antibody or antigen-binding fragment thereof of Embodiment 1, wherein the VH comprises an amino acid sequence that is at least 90%, at least 95%, or at least 97% identical to SEQ ID NO: 18 and the VL comprises an amino acid sequence that is at least 90%, at least 95%, or at least 97% identical to SEQ ID NO: 23.

Embodiment 23. The anti-ceramide antibody or antigen-binding fragment thereof of Embodiment 22, wherein the VH comprises an amino acid sequence that is 100% identical to SEQ ID NO: 18 and the VL comprises an amino acid sequence that is 100% identical to SEQ ID NO: 23.

Embodiment 24. The anti-ceramide antibody or antigen-binding fragment thereof of Embodiment 22, wherein the VH amino acid sequence consists of SEQ ID NO: 18 and the VL amino acid sequence consists of SEQ ID NO: 23.

Embodiment 25. The anti-ceramide antibody or antigen-binding fragment thereof of Embodiment 1, wherein the VH comprises an amino acid sequence that is at least 90%, at least 95%, or at least 97% identical to SEQ ID NO: 18 and the VL comprises an amino acid sequence that is at least 90%, at least 95%, or at least 97% identical to SEQ ID NO: 24.

Embodiment 26. The anti-ceramide antibody or antigen-binding fragment thereof of Embodiment 25, wherein the VH comprises an amino acid sequence that is 100% identical to SEQ ID NO: 18 and the VL comprises an amino acid sequence that is 100% identical to SEQ ID NO: 24.

Embodiment 27. The anti-ceramide antibody or antigen-binding fragment thereof of Embodiment 25, wherein the VH amino acid sequence consists of SEQ ID NO: 18 and the VL amino acid sequence consists of SEQ ID NO: 24.

Embodiment 28. The anti-ceramide antibody or antigen-binding fragment thereof of Embodiment 1, wherein the VH comprises an amino acid sequence that is at least 90%, at least 95%, or at least 97% identical to SEQ ID NO: 19 and the VL comprises an amino acid sequence that is at least 90%, at least 95%, or at least 97% identical to SEQ ID NO: 22.

Embodiment 29. The anti-ceramide antibody or antigen-binding fragment thereof of Embodiment 28, wherein the VH comprises an amino acid sequence that is 100% identical to SEQ ID NO: 19 and the VL comprises an amino acid sequence that is 100% identical to SEQ ID NO: 22.

Embodiment 30. The anti-ceramide antibody or antigen-binding fragment thereof of Embodiment 28, wherein the VH amino acid sequence consists of SEQ ID NO: 19 and the VL amino acid sequence consists of SEQ ID NO: 22.

Embodiment 31. The anti-ceramide antibody or antigen-binding fragment thereof of Embodiment 1, wherein the VH comprises an amino acid sequence that is at least 90%, at least 95%, or at least 97% identical to SEQ ID NO: 19 and the VL comprises an amino acid sequence that is at least 90%, at least 95%, or at least 97% identical to SEQ ID NO: 23.

Embodiment 32. The anti-ceramide antibody or antigen-binding fragment thereof of Embodiment 31, wherein the VH comprises an amino acid sequence that is 100% identical to SEQ ID NO: 19 and the VL comprises an amino acid sequence that is 100% identical to SEQ ID NO: 23.

Embodiment 33. The anti-ceramide antibody or antigen-binding fragment thereof of Embodiment 31, wherein the VH amino acid sequence consists of SEQ ID NO: 19 and the VL amino acid sequence consists of SEQ ID NO: 23.

Embodiment 34. The anti-ceramide antibody or antigen-binding fragment thereof of Embodiment 1, wherein the VH comprises an amino acid sequence that is at least 90%, at least 95%, or at least 97% identical to SEQ ID NO: 19 and the VL comprises an amino acid sequence that is at least 90%, at least 95%, or at least 97% identical to SEQ ID NO: 24.

Embodiment 35. The anti-ceramide antibody or antigen-binding fragment thereof of Embodiment 34, wherein the VH comprises an amino acid sequence that is 100% identical to SEQ ID NO: 19 and the VL comprises an amino acid sequence that is 100% identical to SEQ ID NO:

Embodiment 36. The anti-ceramide antibody or antigen-binding fragment thereof of Embodiment 34, wherein the VH amino acid sequence consists of SEQ ID NO: 19 and the VL amino acid sequence consists of SEQ ID NO: 24.

Embodiment 37. The anti-ceramide antibody or antigen-binding fragment thereof of Embodiment 1, wherein the VH comprises an amino acid sequence that is at least 90%, at least 95%, or at least 97% identical to SEQ ID NO: 20 and the VL comprises an amino acid sequence that is at least 90%, at least 95%, or at least 97% identical to SEQ ID NO: 22.

Embodiment 38. The anti-ceramide antibody or antigen-binding fragment thereof of Embodiment 37, wherein the VH comprises an amino acid sequence that is 100% identical to SEQ ID NO: 20 and the VL comprises an amino acid sequence that is 100% identical to SEQ ID NO: 22.

Embodiment 39. The anti-ceramide antibody or antigen-binding fragment thereof of Embodiment 37, wherein the VH amino acid sequence consists of SEQ ID NO: 20 and the VL amino acid sequence consists of SEQ ID NO: 22.

Embodiment 40. The anti-ceramide antibody or antigen-binding fragment thereof of Embodiment 1, wherein the VH comprises an amino acid sequence that is at least 90%, at least 95%, or at least 97% identical to SEQ ID NO: 21 and the VL comprises an amino acid sequence that is at least 90%, at least 95%, or at least 97% identical to SEQ ID NO: 22.

Embodiment 41. The anti-ceramide antibody or antigen-binding fragment thereof of Embodiment 40, wherein the VH comprises an amino acid sequence that is 100% identical to SEQ ID NO: 21 and the VL comprises an amino acid sequence that is 100% identical to SEQ ID NO: 22.

Embodiment 42. The anti-ceramide antibody or antigen-binding fragment thereof of Embodiment 40, wherein the VH amino acid sequence consists of SEQ ID NO: 21 and the VL amino acid sequence consists of SEQ ID NO: 22.

Embodiment 43. An anti-ceramide antibody or antigen-binding fragment thereof comprising an immunoglobu-lin heavy chain variable region (VH) and an immuno-globulin light chain variable region (VL), wherein the VH comprises an amino acid sequence that is at least 90%, 95%, or 97% identical to a sequence selected from SEQ ID NO: 17, 18, 19, 20, and 21; and wherein the VL comprises an amino acid sequence that is at least 90%, 95%, or 97% identical to a sequence selected from SEQ ID NO: 22, 23 and 24.

Embodiment 44. The anti-ceramide antibody or antigen-binding fragment thereof of Embodiment 43, wherein the VH comprises an amino acid sequence that is at least 90%, 95%, or 97% identical to SEQ ID NO: 17 and the VL comprises an amino acid sequence that is at least 90%, 95%, or 97% identical to SEQ ID NO: 22.

Embodiment 45. The anti-ceramide antibody or antigen-binding fragment thereof of Embodiment 43 or 44, wherein the VH comprises an amino acid sequence that is 100% identical to SEQ ID NO: 17 and the VL comprises an amino acid sequence that is 100% iden-tical to SEQ ID NO: 22.

Embodiment 46. The anti-ceramide antibody or antigen-binding fragment thereof of any one of Embodiments 43-45, wherein the VH amino acid sequence consists of SEQ ID NO: 17 and the VL amino acid sequence consists of SEQ ID NO: 22.

Embodiment 47. The anti-ceramide antibody or antigen-binding fragment thereof of Embodiment 43, wherein the VH comprises an amino acid sequence that is at least 90%, 95%, or 97% identical to SEQ ID NO: 17 and the VL comprises an amino acid sequence that is at least 90%, 95%, or 97% identical to SEQ ID NO: 23.

Embodiment 48. The anti-ceramide antibody or antigen-binding fragment thereof of Embodiment 43 or 47, wherein the VH comprises an amino acid sequence that is 100% identical to SEQ ID NO: 17 and the VL comprises an amino acid sequence that is 100% iden-tical to SEQ ID NO: 23.

Embodiment 49. The anti-ceramide antibody or antigen-binding fragment thereof of any one of Embodiments 43, 47 or 48, wherein the VH amino acid sequence consists of SEQ ID NO: 17 and the VL amino acid sequence consists of SEQ ID NO: 23.

Embodiment 50. The anti-ceramide antibody or antigen-binding fragment thereof of Embodiment 43, wherein the VH comprises an amino acid sequence that is at least 90%, 95%, or 97% identical to SEQ ID NO: 17 and the VL comprises an amino acid sequence that is at least 90%, 95%, or 97% identical to SEQ ID NO: 24.

Embodiment 51. The anti-ceramide antibody or antigen-binding fragment thereof of Embodiment 43 or 50, wherein the VH comprises an amino acid sequence that is 100% identical to SEQ ID NO: 17 and the VL comprises an amino acid sequence that is 100% iden-tical to SEQ ID NO: 24.

Embodiment 52. The anti-ceramide antibody or antigen-binding fragment thereof of any one of Embodiments 43, 50 or 51, wherein the VH amino acid sequence consists of SEQ ID NO: 17 and the VL amino acid sequence consists of SEQ ID NO: 24.

Embodiment 53. The anti-ceramide antibody or antigen-binding fragment thereof of Embodiment 43, wherein the VH comprises an amino acid sequence that is at least 90%, 95%, or 97% identical to SEQ ID NO: 18 and the VL comprises an amino acid sequence that is at least 90%, 95%, or 97% identical to SEQ ID NO: 22.

Embodiment 54. The anti-ceramide antibody or antigen-binding fragment thereof of Embodiment 43 or 53, wherein the VH comprises an amino acid sequence that is 100% identical to SEQ ID NO: 18 and the VL comprises an amino acid sequence that is 100% iden-tical to SEQ ID NO: 22.

Embodiment 55. The anti-ceramide antibody or antigen-binding fragment thereof of any one of Embodiments 43, 53 or 54, wherein the VH amino acid sequence consists of SEQ ID NO: 18 and the VL amino acid sequence consists of SEQ ID NO: 22.

Embodiment 56. The anti-ceramide antibody or antigen-binding fragment thereof of Embodiment 43, wherein the VH comprises an amino acid sequence that is at least 90%, 95%, or 97% identical to SEQ ID NO: 18 and the VL comprises an amino acid sequence that is at least 90%, 95%, or 97% identical to SEQ ID NO: 23.

Embodiment 57. The anti-ceramide antibody or antigen-binding fragment thereof of Embodiment 43 or 56, wherein the VH comprises an amino acid sequence that is 100% identical to SEQ ID NO: 18 and the VL comprises an amino acid sequence that is 100% iden-tical to SEQ ID NO: 23.

Embodiment 58. The anti-ceramide antibody or antigen-binding fragment thereof of any one of Embodiments 43, 56 or 57, wherein the VH amino acid sequence consists of SEQ ID NO: 18 and the VL amino acid sequence consists of SEQ ID NO: 23.

Embodiment 59. The anti-ceramide antibody or antigen-binding fragment thereof of Embodiment 43, wherein the VH comprises an amino acid sequence that is at least 90%, 95%, or 97% identical to SEQ ID NO: 18 and the VL comprises an amino acid sequence that is at least 90%, 95%, or 97% identical to SEQ ID NO: 24.

Embodiment 60. The anti-ceramide antibody or antigen-binding fragment thereof of Embodiment 43 or 59, wherein the VH comprises an amino acid sequence that is 100% identical to SEQ ID NO: 18 and the VL comprises an amino acid sequence that is 100% identical to SEQ ID NO: 24.

Embodiment 61. The anti-ceramide antibody or antigen-binding fragment thereof of any one of Embodiments 43, 59 or 60, wherein the VH amino acid sequence consists of SEQ ID NO: 18 and the VL amino acid sequence consists of SEQ ID NO: 24.

Embodiment 62. The anti-ceramide antibody or antigen-binding fragment thereof of Embodiment 43, wherein the VH comprises an amino acid sequence that is at least 90%, 95%, or 97% identical to SEQ ID NO: 19 and the VL comprises an amino acid sequence that is at least 90%, 95%, or 97% identical to SEQ ID NO: 22.

Embodiment 63. The anti-ceramide antibody or antigen-binding fragment thereof of Embodiment 43 or 62, wherein the VH comprises an amino acid sequence that is 100% identical to SEQ ID NO: 19 and the VL comprises an amino acid sequence that is 100% identical to SEQ ID NO: 22.

Embodiment 64. The anti-ceramide antibody or antigen-binding fragment thereof of any one of Embodiments 43, 62 or 63, wherein the VH amino acid sequence consists of SEQ ID NO: 19 and the VL amino acid sequence consists of SEQ ID NO: 22.

Embodiment 65. The anti-ceramide antibody or antigen-binding fragment thereof of Embodiment 43, wherein the VH comprises an amino acid sequence that is at least 90%, 95%, or 97% identical to SEQ ID NO: 19 and the VL comprises an amino acid sequence that is at least 90%, 95%, or 97% identical to SEQ ID NO: 23.

Embodiment 66. The anti-ceramide antibody or antigen-binding fragment thereof of Embodiment 43 or 65, wherein the VH comprises an amino acid sequence that is 100% identical to SEQ ID NO: 19 and the VL comprises an amino acid sequence that is 100% identical to SEQ ID NO: 23.

Embodiment 67. The anti-ceramide antibody or antigen-binding fragment thereof of any one of Embodiments 43, 65 or 66, wherein the VH amino acid sequence consists of SEQ ID NO: 19 and the VL amino acid sequence consists of SEQ ID NO: 23.

Embodiment 68. The anti-ceramide antibody or antigen-binding fragment thereof of Embodiment 43, wherein the VH comprises an amino acid sequence that is at least 90%, 95%, or 97% identical to SEQ ID NO: 19 and the VL comprises an amino acid sequence that is at least 90%, 95%, or 97% identical to SEQ ID NO: 24.

Embodiment 69. The anti-ceramide antibody or antigen-binding fragment thereof of Embodiment 43 or 68, wherein the VH comprises an amino acid sequence that is 100% identical to SEQ ID NO: 19 and the VL comprises an amino acid sequence that is 100% identical to SEQ ID NO: 24.

Embodiment 70. The anti-ceramide antibody or antigen-binding fragment thereof of any one of Embodiments 43, 68 or 69, wherein the VH amino acid sequence consists of SEQ ID NO: 19 and the VL amino acid sequence consists of SEQ ID NO: 24.

Embodiment 71. The anti-ceramide antibody or antigen-binding fragment thereof of Embodiment 43, wherein the VH comprises an amino acid sequence that is at least 90%, 95%, or 97% identical to SEQ ID NO: 20 and the VL comprises an amino acid sequence that is at least 90%, 95%, or 97% identical to SEQ ID NO: 22.

Embodiment 72. The anti-ceramide antibody or antigen-binding fragment thereof of Embodiment 43 or 71, wherein the VH comprises an amino acid sequence that is 100% identical to SEQ ID NO: 20 and the VL comprises an amino acid sequence that is 100% identical to SEQ ID NO: 22.

Embodiment 73. The anti-ceramide antibody or antigen-binding fragment thereof of any one of Embodiments 43, 71 or 72, wherein the VH amino acid sequence consists of SEQ ID NO: 20 and the VL amino acid sequence consists of SEQ ID NO: 22.

Embodiment 74. The anti-ceramide antibody or antigen-binding fragment thereof of Embodiment 43, wherein the VH comprises an amino acid sequence that is at least 90%, 95%, or 97% identical to SEQ ID NO: 21 and the VL comprises an amino acid sequence that is at least 90%, 95%, or 97% identical to SEQ ID NO: 22.

Embodiment 75. The anti-ceramide antibody or antigen-binding fragment thereof of Embodiment 43 or 74, wherein the VH comprises an amino acid sequence that is 100% identical to SEQ ID NO: 21 and the VL comprises an amino acid sequence that is 100% identical to SEQ ID NO: 22.

Embodiment 76. The anti-ceramide antibody or antigen-binding fragment thereof of any one of Embodiments 43, 74 or 75, wherein the VH amino acid sequence consists of SEQ ID NO: 21 and the VL amino acid sequence consists of SEQ ID NO: 22.

Embodiment 77. The anti-ceramide antibody or antigen-binding fragment thereof of any one of Embodiments 1-76, wherein the antibody or antigen-binding fragment is humanized.

Embodiment 78. The anti-ceramide antibody or antigen-binding fragment thereof of any one of Embodiments 1-76, wherein the antibody or antigen-binding fragment is fully human.

Embodiment 79. The anti-ceramide antibody or antigen-binding fragment thereof of any one of Embodiments 1-78, wherein the anti-ceramide antibody comprises one or more point mutations in the Fc domain of the antibody.

Embodiment 80. The anti-ceramide antibody or antigen-binding fragment thereof of any one of Embodiments 1-79, wherein the antigen-binding fragment is a single chain variable fragment (scFv).

Embodiment 81. The anti-ceramide antibody or antigen-binding fragment thereof of Embodiment 80, wherein the scFv comprises an amino acid sequence that is at least 90%, at least 95%, or at least 97% identical to a sequence selected from the group consisting of SEQ ID NOs: 48-61.

Embodiment 82. The anti-ceramide antibody or antigen-binding fragment thereof of Embodiment 80, wherein the scFv comprises an amino acid sequence that is 100% identical to a sequence selected from the group consisting of SEQ ID NOs: 48-61.

Embodiment 83. The anti-ceramide antibody or antigen-binding fragment thereof of Embodiment 80, wherein the scFv consists of a sequence selected from the group consisting of SEQ ID NOs: 48-61.

Embodiment 84. The anti-ceramide antibody or antigen-binding fragment thereof of Embodiment 80, wherein the light chain variable region of said scFv is carboxy-terminal to the heavy chain variable region of said scFv.

Embodiment 85. The anti-ceramide antibody or antigen-binding fragment thereof of Embodiment 80, wherein the light chain variable region of said scFv is amino-terminal to the heavy chain variable region of said scFv.

Embodiment 86. The anti-ceramide antibody or antigen-binding fragment thereof of any one of Embodiments 80-85, wherein the scFv comprises a linker polypeptide.

Embodiment 87. The anti-ceramide antibody or antigen-binding fragment thereof of Embodiment 86, wherein the linker polypeptide is between the light chain variable region and the heavy chain variable region of the said scFv.

Embodiment 88. The anti-ceramide antibody or antigen-binding fragment thereof of Embodiment 86 or 87, wherein the linker polypeptide comprises a Gly4Ser linker.

Embodiment 89. The anti-ceramide antibody or antigen-binding fragment thereof of any one of Embodiments 86-88, wherein the linker polypeptide comprises the formula (Gly4Ser)n, wherein n=1-5.

Embodiment 90. An anti-ceramide single chain variable fragment (scFv) comprising an amino acid sequence that is at least 80%, at least 85%, at least 90%, at least 95%, or at least 97% identical to a sequence selected from the group consisting of SEQ ID NOs: 48-61.

Embodiment 91. The anti-ceramide scFv of Embodiment 90, wherein the scFv comprises an amino acid sequence that is 100% identical to a sequence selected from the group consisting of SEQ ID NOs: 48-61.

Embodiment 92. The anti-ceramide scFv of Embodiment 90, consisting of an amino acid sequence selected from the group consisting of SEQ ID NOs: 48-61.

Embodiment 93. A polynucleotide encoding the anti-ceramide antibody or antigen-binding fragment thereof of any one of Embodiments 1-92.

Embodiment 94. An anti-ceramide single chain variable fragment (scFv) comprising an amino acid sequence that is at least 80%, at least 85%, at least 90%, at least 95%, or at least 97% identical to SEQ ID NO: 48 or 51.

Embodiment 95. The anti-ceramide scFv of Embodiment 94, wherein the scFv comprises an amino acid sequence that is 100% identical to SEQ ID NO: 48 or 51.

Embodiment 96. The anti-ceramide scFv of Embodiment 94, consisting of the amino acid sequence of SEQ ID NO: 48 or 51.

Embodiment 97. A polynucleotide encoding the anti-ceramide single chain variable fragment (scFv) of any one of Embodiments 94-96.

Embodiment 98. An expression vector comprising the polynucleotide of any one of Embodiments 93 or 97.

Embodiment 99. A host cell comprising the polynucleotide of any one of Embodiments 93 or 97 or the expression vector of Embodiment 97.

Embodiment 100. A method of manufacturing the anti-ceramide antibody or antigen-binding fragment thereof of any one of Embodiments 1-89 or the anti-ceramide single chain variable fragment (scFv) of any one of Embodiments 94-96, comprising introducing the expression vector of Embodiment 98 into a host cell.

Embodiment 101. A method of inhibiting apoptosis in a subject in need thereof, comprising administering to the subject a therapeutically effective amount of the anti-ceramide antibody or antigen-binding fragment thereof of any one of Embodiments 1-88 or the anti-ceramide scFv of any one of Embodiments 94-96.

Embodiment 102. The method of Embodiment 101, wherein the apoptosis is associated with a disease selected from the group consisting of graft versus host disease, radiation disease, GI syndrome, and autoimmune disease.

Embodiment 103. The method of Embodiment 102, wherein the disease is radiation disease or GI syndrome and the anti-ceramide antibody or antigen-binding fragment thereof is administered before the subject is exposed to radiation.

Embodiment 104. The method of Embodiment 102, wherein the disease is graft versus host disease and the anti-ceramide antibody or antigen-binding fragment thereof is administered before the subject receives a transplant.

Embodiment 105. The method of Embodiment 104, wherein the transplant is a bone marrow transplant.

Embodiment 106. The method of Embodiment 101, wherein the anti-ceramide antibody or antigen-binding fragment thereof is administered intravenously, intramuscularly, intraperitoneally, intracerobrospinally, subcutaneously, intrasynovially, intrathecally, orally, topically, or via inhalation.

Embodiment 107. A method for mitigating apoptosis in a subject with GI syndrome comprising administering to the subject an effective amount of the anti-ceramide antibody or antigen-binding fragment thereof of any one of Embodiments 1-89 or the anti-ceramide scFv of any one of Embodiments 94-96, after the subject is exposed to penetrating radiation.

Embodiment 108. The method of Embodiment 107, wherein the anti-ceramide antibody or antigen-binding fragment thereof is administered immediately after the subject is exposed to penetrating radiation.

Embodiment 109. The method of Embodiment 107, wherein the anti-ceramide antibody or antigen-binding fragment thereof is administered within 24 hours after the subject is exposed to penetrating radiation.

Embodiment 110. A method for inhibiting apoptosis in a subject with GvHD comprising administering to the subject an effective amount of anti-ceramide antibody or antigen binding fragment thereof of any one of Embodiments 1-89 or the anti-ceramide scFv of any one of Embodiments 94-96, either before the subject receives a transplant or after the subject receives a transplant prior to the onset of GvHD.

Embodiment 111. The method of Embodiment 110, wherein the transplant is a bone marrow transplant.

Embodiment 112. An anti-ceramide antibody or antigen-binding fragment thereof comprising an immunoglobulin heavy chain variable region (VH) comprising a heavy chain complementarity determining region (CDR) 1 (HCDR1), a heavy chain CDR2 (HCDR2), and a heavy chain CDR3 (HCDR3), and an immunoglobulin light chain variable region (VL) comprising a light chain complementarity determining region (CDR) 1 (LCDR1), a light chain CDR2 (LCDR2), and a light chain CDR3 (LCDR3), wherein: (a) the HCDR1 comprises an amino acid sequence selected from GYTFTDHTIH (SEQ ID NO: 1) and GYTFTDHTMH (SEQ ID NO: 2); (b) the HCDR2 comprises an amino acid sequence selected from YNYPRDGST-KYNEKFQG (SEQ ID NO: 3), YNYPREGST-KYNEKFQG (SEQ ID NO: 4), YNYPRDVST-KYNEKFQG (SEQ ID NO: 5), and YNYPRDGSTKYAEKFQG (SEQ ID NO: 6); (c) the HCDR3 comprises the amino acid sequence of GFIT-TVVPSAY (SEQ ID NO: 7); (d) the LCDR1 comprises the amino acid sequence of RASKSISKYLA (SEQ ID NO: 8); (e) the LCDR2 comprises the amino acid sequence of SGSTLQS (SEQ ID NO: 9); and (f) the LCDR3 comprises the amino acid sequence of QQH-NEYPWT (SEQ ID NO: 10).

Embodiment 113. The anti-ceramide antibody or antigen-binding fragment thereof of Embodiment 112, wherein the HCDR1 comprises GYTFTDHTIH (SEQ ID NO: 1) and the HCDR2 comprises YNYPRDGST-KYNEKFQG (SEQ ID NO: 3).

Embodiment 114. The anti-ceramide antibody or antigen-binding fragment thereof of Embodiment 112, wherein the HCDR1 comprises GYTFTDHTIH (SEQ ID NO: 1) and the HCDR2 comprises YNYPREGST-KYNEKFQG (SEQ ID NO: 4).

Embodiment 115. The anti-ceramide antibody or antigen-binding fragment thereof of Embodiment 112, wherein the HCDR1 comprises GYTFTDHTIH (SEQ ID NO: 1) and the HCDR2 comprises YNYPRDVST-KYNEKFQG (SEQ ID NO: 5).

Embodiment 116. The anti-ceramide antibody or antigen-binding fragment thereof of Embodiment 112, wherein the HCDR1 comprises GYTFTDHTIH (SEQ ID NO: 1) and the HCDR2 comprises YNYPRDGSTKY-AEKFQG (SEQ ID NO: 6).

Embodiment 117. The anti-ceramide antibody or antigen-binding fragment thereof of Embodiment 112, wherein the HCDR1 comprises GYTFTDHTMH (SEQ ID NO: 2) and the HCDR2 comprises YNYPRDGST-KYNEKFQG (SEQ ID NO: 3).

Embodiment 118. The anti-ceramide antibody or antigen-binding fragment thereof of Embodiment 112, wherein the HCDR1 comprises GYTFTDHTMH (SEQ ID NO: 2) and the HCDR2 comprises YNYPREGST-KYNEKFQG (SEQ ID NO: 4).

Embodiment 119. The anti-ceramide antibody or antigen-binding fragment thereof of Embodiment 112, wherein the HCDR1 comprises GYTFTDHTMH (SEQ ID NO: 2) and the HCDR2 comprises YNYPRDVST-KYNEKFQG (SEQ ID NO: 5).

Embodiment 120. The anti-ceramide antibody or antigen-binding fragment thereof of Embodiment 112, wherein the HCDR1 comprises GYTFTDHTMH (SEQ ID NO: 2) and the HCDR2 comprises YNYPRDGSTKY-AEKFQG (SEQ ID NO: 6).

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

| Sequence Listing of the Present Disclosure: | | | |
|---|---|---|---|
| Seq Desc. | Chain | Sequence | SEQ ID |
| HCDR1-IH | Heavy | GYTFTDHTIH | 1 |
| HCDRI-IH-MH | Heavy | GYTFTDHTMH | 2 |
| HCDR2-DG | Heavy | YNYPRDGSTKYNEKFQG | 3 |
| HCDR2-DG-EG | Heavy | YNYPREGSTKYNEKFQG | 4 |
| HCDR2-DG-DV | Heavy | YNYPRDVSTKYNEKFQG | 5 |
| HCDR2-NE-AE | Heavy | YNYPRDGSTKYAEKFQG | 6 |
| HCDR3 | Heavy | GFITTWPSAY | 7 |
| LCDR1 | Light | RASKSISKYLA | 8 |
| LCDR2 | Light | SGSTLQS | 9 |
| LCDR3 | Light | QQHNEYPWT | 10 |
| Parental 6B5 HCDR1 | Heavy | GYTFTDHTIH | 11 |
| Parental 6B5 HCDR2 | Heavy | YNYPRDGSTKYNEKFKG | 12 |
| Parental 6B5 HCDR3 | Heavy | GFITTWPSAY | 13 |
| Parental 6B5 LCDR1 | Light | RASKSISKYLA | 14 |

-continued

| | | Sequence Listing of the Present Disclosure: | |
|---|---|---|---|
| Seq Desc. | Chain | Sequence | SEQ ID |
| Parental 6B5 LCDR2 | Light | SGSTLQS | 15 |
| Parental 6B5 LCDR3 | Light | QQHNEYPWT | 16 |
| Humanized VH1 | Heavy | QVQLVQSGAEVKKPGASVKVSCKASGYTFTDHTMHWVRQAPGQGLEWMGYNY PRDGSTKYAEKFQGRVTMTADKSTSTVYMELSSLRSEDTAVYYCAKGFITTV VPSAYWGQGTLVTVSS | 17 |
| Humanized VH2 | Heavy | QVQLVQSGAEVKKPGASVKVSCKVSGYTFTDHTIHWMRQAPGQGLEWMGYNY PRDGSTKYNEKFQGRVTMTADKSTSTVYMELSSLRSEDTAVYYCAKGFITTV VPSAYWGQGTLVTVSS | 18 |
| Humanized VH3 | Heavy | QVQLVQSGAEVKKPGATVKISCKVSGYTFTDHTIHWMQQAPGKGLEWMGYNY PRDGSTKYNEKFQGRVTITADKSTSTAYMELSSLRSEDTAVYYCAKGFITTV VPSAYWGQGTLVTVSS | 19 |
| Humanized VH4 | Heavy | QVQLVQSGAEVKKPGASVKVSCKVSGYTFTDHTIHWMRQAPGQGLEWMGYNY PREGSTKYNEKFQGRVTMTADKSTSTVYMELSSLRSEDTAVYYCAKGFITTV VPSAYWGQGTLVTVSS | 20 |
| Humanized VH5 | Heavy | QVQLVQSGAEVKKPGASVKVSCKVSGYTFTDHTIHWMRQAPGQGLEWMGYNY PRDVSTKYNEKFQGRVTMTADKSTSTVYMELSSLRSEDTAVYYCAKGFITTV VPSAYWGQGTLVTVSS | 21 |
| Humanized VLI | Light | DIQLTQSPSFLSASVGDRVTITCRASKSISKYLAWYQQKPGKAPKLLIYSGS TLQSGVPSRFSGSGSGTEFTLTISSLQPEDFATYYCQQHNEYPWTFGGGTKV EIK | 22 |
| Humanized VL2 | Light | DVQITQSPSFLSASVGDRVTITCRASKSISKYLAWYQQKPGKANKLLIYSGS TLQSGVPSRFSGSGSGTDFTLTISSLQPEDFATYYCQQHNEYPWTFGGGTKV EIK | 23 |
| Humanized VL3 | Light | DVQLTQSPSSVSASVGDRVTITCRASKSISKYLAWYQQKPGKAPKLLIYSGS TLQSGVPSRFSGSGSGTDFTLTISSLQPEDFATYYCQQHNEYPWTFGPGTKV EIK | 24 |
| STD1 linker | | NYGGGGSGGGGSGGGGSGNS | 25 |
| STD2 linker | | NYGGGGSGGGGSGGGGSGNYGGGGSGGGGSGGGGSGNS | 26 |
| H1 linker | | NS | 27 |
| H2 linker | | GGGGSGNS | 28 |
| H3 linker | | NYGGGGSGNS | 29 |
| H4 linker | | GGGGSGGGGSGNS | 30 |
| H5 linker | | NYGGGGSGGGGSGNS | 31 |
| H6 linker | | GGGGSGGGGSGGGGSGNS | 32 |
| H7 linker | | GCPPCPNS | 33 |
| Gly$_4$Ser linker | | GGGGS | 34 |
| (G$_4$S)$_3$ linker | | GGGGSGGGGSGGGGS | 35 |
| H105 linker | | SGGGGSGGGGSGGGGS | 36 |
| (G$_4$S)$_4$ linker | | GGGGSGGGGSGGGGSGGGGS | 37 |
| H75 linker (NKG2A quadruple mutant) | | QRHNNSSLNTGTQMAGHSPNS | 38 |
| H83 linker (NKG2A derived) | | SSLNTGTQMAGHSPNS | 39 |

| Seq Desc. | Chain | Sequence | SEQ ID |
|---|---|---|---|
| H106 linker (NKG2A derived) | | QRHNNSSLNTGTQMAGHS | 40 |
| H81 linker (NKG2D derived) | | EVQIPLTESYSPNS | 41 |
| H91 linker (NKG2D derived) | | NSLANQEVQIPLTESYSPNS | 42 |
| H94 linker | | SGGGGSGGGGSGGGGSPNS | 43 |
| H111 linker | | SGGGGSGGGGSGGGGSPGS | 44 |
| H113 linker | | SGGGGSGGGGSGGGGSPAS | 45 |
| H114 linker | | SGGGGSGGGGSGGGGSPS | 46 |
| H115 linker | | SGGGGSGGGGSGGGGSPSS | 47 |
| VH2-VL1 (Lead) scFv | | MEWSWVFLFFLSVTTGVHSQVQLVQSGAEVKKPGASVKVSCKVSGYTFTDHT IHWMRQAPGQGLEWMGYNYPRDGSTKYNEKFQGRVTMTADKSTSTVYMELSS LRSEDTAVYYCAKGFITTVVPSAYWGQGTLVTVSSGGGGSGGGGSGGGGSDI QLTQSPSFLSASVGDRVTITCRASKSISKYLAWYQQKPGKAPKLLIYSGSTL QSGVPSRFSGSGSGTEFTLTISSLQPEDFATYYCQQHNEYPWTFGGGTKVEI KRAAAGGGGSGGGGSHHHHHHHH | 48 |
| VH4-VL1 scFv | | MEWSWVFLFFLSVTTGVHSQVQLVQSGAEVKKPGASVKVSCKVSGYTFTDHT IHWMRQAPGQGLEWMGYNYPREGSTKYNEKFQGRVTMTADKSTSTVYMELSS LRSEDTAVYYCAKGFITTVVPSAYWGQGTLVTVSSGGGGSGGGGSGGGGSDI QLTQSPSFLSASVGDRVTITCRASKSISKYLAWYQQKPGKAPKLLIYSGSTL QSGVPSRFSGSGSGTEFTLTISSLQPEDFATYYCQQHNEYPWTFGGGTKVEI KRAAAGGGGSGGGGSHHHHHHHH | 49 |
| VH5-VL1 scFv | | MEWSWVFLFFLSVTTGVHSQVQLVQSGAEVKKPGASVKVSCKVSGYTFTDHT IHWMRQAPGQGLEWMGYNYPRDVSTKYNEKFQGRVTMTADKSTSTVYMELSS LRSEDTAVYYCAKGFITTVVPSAYWGQGTLVTVSSGGGGSGGGGSGGGGSDI QLTQSPSFLSASVGDRVTITCRASKSISKYLAWYQQKPGKAPKLLIYSGSTL QSGVPSRFSGSGSGTEFTLTISSLQPEDFATYYCQQHNEYPWTFGGGTKVEI KRAAAGGGGSGGGGSHHHHHHHH | 50 |
| VH2-VL1 scFv-no signal sequence | | QVQLVQSGAEVKKPGASVKVSCKVSGYTFTDHTIHWMRQAPGQGLEWMGYNY PRDGSTKYNEKFQGRVTMTADKSTSTVYMELSSLRSEDTAVYYCAKGFITTV VPSAYWGQGTLVTVSS*GGGGSGGGGSGGGGS*DIQLTQSPSFLSASVGDRVTI TCRASKSISKYLAWYQQKPGKAPKLLIYSGSTLQSGVPSRFSGSGSGTEFTL TISSLQPEDFATYYCQQHNEYPWTFGGGTKVEIK*RAAAGGGGS GGGGSHHHHHHHH* | 51 |
| VH4-VL1 scFv-no signal sequence | | QVQLVQSGAEVKKPGASVKVSCKVSGYTFTDHTIHWMRQAPGQGLEWMGYNY PREGSTKYNEKFQGRVTMTADKSTSTVYMELSSLRSEDTAVYYCAKGFITTV VPSAYWGQGTLVTVSS*GGGGSGGGGSGGGGS*DIQLTQSPSFLSASVGDRVTI TCRASKSISKYLAWYQQKPGKAPKLLIYSGSTLQSGVPSRFSGSGSGTEFTL TISSLQPEDFATYYCQQHNEYPWTFGGGTKVEIK*RAAAGGGGS GGGGSHHHHHHHH* | 52 |
| VH5-VL1 scFv-no signal sequence | | QVQLVQSGAEVKKPGASVKVSCKVSGYTFTDHTIHWMRQAPGQGLEWMGYNY PRDVSTKYNEKFQGRVTMTADKSTSTVYMELSSLRSEDTAVYYCAKGFITTV VPSAYWGQGTLVTVSS*GGGGSGGGGSGGGGS*DIQLTQSPSELSASVGDRVTI TCRASKSISKYLAWYQQKPGKAPKLLIYSGSTLQSGVPSRFSGSGSGTEFTL TISSLQPEDFATYYCQQHNEYPWTFGGGTKVEIK*RAAAGGGGS GGGGSHHHHHHHH* | 53 |
| VHI-VL1 scFv | | QVQLVQSGAEVKKPGASVKVSCKASGYTFTDHTMHWVRQAPGQGLEWMGYNY PRDGSTKYAEKFQGRVTMTADKSTSTVYMELSSLRSEDTAVYYCAKGFITTV VPSAYWGQGTLVTVSS*GGGGSGGGGSGGGGS*DIQLTQSPSFLSASVGDRVTI TCRASKSISKYLAWYQQKPGKAPKLLIYSGSTLQSGVPSRFSGSGSGTEFTL TISSLQPEDFATYYCQQHNEYPWTFGGGTKVEIK*RAAAGGGGS GGGGSHHHHHHHH* | 54 |

-continued

| Sequence Listing of the Present Disclosure: | | | |
|---|---|---|---|
| Seq Desc. | Chain | Sequence | SEQ ID |
| VH1-VL2 scFv | | QVQLVQSGAEVKKPGASVKVSCKASGYTFTDHTMHWVRQAPGQGLEWMGYNY PRDGSTKYAEKFQGRVTMTADKSTSTVYMELSSLRSEDTAVYYCAKGFITTV VPSAYWGQGTLVTVSS*GGGGSGGGGSGGGGS*DVQITQSPSFLSASVGDRVTI TCRASKSISKYLAWYQQKPGKANKLLIYSGSTLQSGVPSRFSGSGSGTDFTL TISSLQPEDFATYYCQQHNEYPWTFGGGTKVEIK*RAAAGGGGS GGGGSHHHHHHH* | 55 |
| VH1-VL3 scFv | | QVQLVQSGAEVKKPGASVKVSCKASGYTFTDHTMHWVRQAPGQGLEWMGYNY PRDGSTKYAEKFQGRVTMTADKSTSTVYMELSSLRSEDTAVYYCAKGFITTV VPSAYWGQGTLVTVSS*GGGGSGGGGSGGGGS*DVQLTQSPSSVSASVGDRVTI TCRASKSISKYLAWYQQKPGKAPKLLIYSGSTLQSGVPSRFSGSGSGTDFTL TISSLQPEDFATYYCQQHNEYPWTFGPGTKVEIK*RAAAGGGGS GGGGSHHHHHHH* | 56 |
| VH2-VL2 scFv | | QVQLVQSGAEVKKPGASVKVSCKVSGYTFTDHTIHWMRQAPGQGLEWMGYNY PRDGSTKYNEKFQGRVTMTADKSTSTVYMELSSLRSEDTAVYYCAKGFITTV VPSAYWGQGTLVTVSS*GGGGSGGGGSGGGGS*DVQITQSPSFLSASVGDRVTI TCRASKSISKYLAWYQQKPGKANKLLIYSGSTLQSGVPSRFSGSGSGTDFTL TISSLQPEDFATYYCQQHNEYPWTFGGGTKVEIK*RAAAGGGGS GGGGSHHHHHHH* | 57 |
| VH2-VL3 scFv | | QVQLVQSGAEVKKPGASVKVSCKVSGYTFTDHTIHWMRQAPGQGLEWMGYNY PRDGSTKYNEKFQGRVTMTADKSTSTVYMELSSLRSEDTAVYYCAKGFITTV VPSAYWGQGTLVTVSS*GGGGSGGGGSGGGGS*DVQLTQSPSSVSASVGDRVTI TCRASKSISKYLAWYQQKPGKAPKLLIYSGSTLQSGVPSRFSGSGSGTDFTL TISSLQPEDFATYYCQQHNEYPWTFGPGTKVEIK*RAAAGGGGS GGGGSHHHHHHH* | 58 |
| VH3-VL1 scFv | | QVQLVQSGAEVKKPGATVKISCKVSGYTFTDHTIHWMQQAPGKGLEWMGYNY PRDGSTKYNEKFQGRVTITADKSTSTAYMELSSLRSEDTAVYYCAKGFITTV VPSAYWGQGTLVTVSS*GGGGSGGGGSGGGGS*DIQLTQSPSFLSASVGDRVTI TCRASKSISKYLAWYQQKPGKAPKLLIYSGSTLQSGVPSRFSGSGSGTEFTL TISSLQPEDFATYYCQQHNEYPWTFGGGTKVEIK*RAAAGGGGS GGGGSHHHHHHH* | 59 |
| VH3-VL2 scFv | | QVQLVQSGAEVKKPGATVKISCKVSGYTFTDHTIHWMQQAPGKGLEWMGYNY PRDGSTKYNEKFQGRVTITADKSTSTAYMELSSLRSEDTAVYYCAKGFITTV VPSAYWGQGTLVTVSS*GGGGSGGGGSGGGGS*DVQITQSPSFLSASVGDRVTI TCRASKSISKYLAWYQQKPGKANKLLIYSGSTLQSGVPSRFSGSGSGTDFTL TISSLQPEDFATYYCQQHNEYPWTFGGGTKVEIK*RAAAGGGGS GGGGSHHHHHHH* | 60 |
| VH3-VL3 scFv | | QVQLVQSGAEVKKPGATVKISCKVSGYTFTDHTIHWMQQAPGKGLEWMGYNY PRDGSTKYNEKFQGRVTITADKSTSTAYMELSSLRSEDTAVYYCAKGFITTV VPSAYWGQGTLVTVSS*GGGGSGGGGSGGGGS*DVQLTQSPSSVSASVGDRVTI TCRASKSISKYLAWYQQKPGKAPKLLIYSGSTLQSGVPSRFSGSGSGTDFTL TISSLQPEDFATYYCQQHNEYPWTFGPGTKVEIK*RAAAGGGGS GGGGSHHHHHHH* | 61 |
| Mouse 6B5 scFv | | MKKTAIAIAVALAGFATVAQAVQLQQSDAELVKPGASVKISCKVSGYTFTD HTIHWMKQRPEQGLEWIGYNYPRDGSTKYNEKFKGKATLTADKSSSTAYMQL NSLTSEDSAVYFCAKGFITTVVPSAYWGQGTLVTVSAGGGGSGGGGSGGGGS DVQITQSPSYLAASPGETITINCRASKSISKYLAWYQEKPGKTNKLLIYSGS TLQSGIPSRFSGSGSGTDFTLTISSLEPEDFAMYYCQQHNEYPWTFGGGTKL EIKGSHHHHHH | 62 |
| Murine 6B5 VH parental | | QVQLQQSDAELVKPGASVKISCKVSGYTFTDHTIHWMKQRPEQGLEWIGYNY PRDGSTKYNEKFKGKATLTADKSSSTAYMQLNSLTSEDSAVYFCAKGFITTV VPSAYWGQGTLVTVSA | 63 |
| Murine 6B5 VLparental | | DVQITQSPSYLAASPGETITINCRASKSISKYLAWYQEKPGKTNKLLIYSGS TLQSGIPSRFSGSGSGTDFTLTISSLEPEDFAMYYCQQHNEYPWTFGGGTKL EIK | 64 |
| VH3-VL3 scFv nucleic acid sequence | | ATGAAGTACCTTCTTCCCACCGCCGCGGCTGGGTTGTTGTTACTTGCAGCAC AACCGGCGATGGCTCAAGTCCAGTTAGTTCAGTCGGGGGCCGAAGTAAAGAA GCCAGGTGCTACTGTGAAAATTTCGTGCAAAGTGAGCGGATACACATTCACG GACCACACGATTCACTGGATGCAGCAAGCTCCGGGCAAGGGTCTTGAGTGGA TGGGCTACAACTATCGCGTGACGGATCAACAAAATACAATGAAAAATTTCA AGGGCGTGTTACAATTACCGCGGATAAATCCACGAGTACTGCCTACATGGAG TTGTCCTCACTTCGTTCAGAGGACACAGCAGTGTACTATTGTGCTAAAGGGT TCATCACGACCGTGGTCCCCTCTGCTTATTGGGGCCAAGGAACACTTGTGAC TGTGTCTTCTGGGGGCGGGGGGAGCGGAGGCGGAGGTAGCGGTGGCGGGGGT | 65 |

| Seq Desc. | Chain | Sequence | SEQ ID |
|-----------|-------|----------|--------|
| | | AGTGACGTTCAACTGACTCAATCGCCTTCATCCGTTAGCGCCAGCGTAGGCG<br>ACCGTGTGACCATCACGTGCCGCGCGTCCAAAAGTATCAGCAAGTACCTGGC<br>CTGGTACCAACAAAAACCCGGAAAGGCACCGAAGTTGTTGATTTATTCCGGT<br>TCAACATTACAAAGCGGCGTTCCGAGTCGTTTCAGTGGTAGCGGTTCCGGCA<br>CAGATTTTACCTTGACCATTTCCTCCCTGCAGCCAGAAGACTTTGCTACTTA<br>TTACTGTCAACAGCACAATGAGTACCCGTGGACGTTTGGGCCTGGAACTAAG<br>GTTGAGATTAAGCGTGCTGCTGCCGGGGGCGGTGGTTCCGGAGGAGGAGGAA<br>GTCACCACCACCATCACCATCATCATGGT | |
| VH3-VL2<br>scFv nucleic<br>acid sequence | | ATGAAATATCTGCTGCCAACTGCGGCAGCAGGTCTGTTGCTTCTGGCCGCTC<br>AACCGGCCATGGCTCAAGTCCAGTTAGTTCAGAGTGGGGCAGAGGTTAAAAA<br>ACCGGGAGCTACAGTAAAGATCAGCTGTAAAGTATCAGGTTATACATTTACT<br>GACCATACTATCCACTGGATGCAACAGGCGCCAGGGAAAGGTTTGGAGTGGA<br>TGGGATATAATTATCCACGCGACGGGTCAACTAAGTACAACGAGAAGTTTCA<br>AGGCCGTGTAACGATTACCGCGGACAAAAGCACGAGTACAGCGTACATGGAA<br>TTATCATCTTTGCGCTCGGAGGACACAGCGGTCTATTACTGTGCCAAGGGTT<br>TCATCACTACTGTGGTACCAAGTGCGTATTGGGGTCAAGGAACCCTTGTTAC<br>GGTGTCATCAGGGGGTGGCGGAAGTGGCGGTGGTGGATCGGGCGGAGGTGGA<br>AGCGATGTTCAGATCACACAGTCGCCCTCGTTCCTGAGTGCAAGTGTCGGTG<br>ATCGTGTGACTATTACGTGTCGTGCATCGAAATCAATCTCAAAGTATCTGGC<br>TTGGTACCAGCAAAAACCTGGAAAGGCTAACAAATTGTTGATCTATTCCGGC<br>AGCACCCTTCAAAGCGGTGTCCCCTCTCGTTTCTCCGGATCCGGGTCAGGGA<br>CCGACTTTACTCTGACTATTTCCAGTCTTCAGCCGGAAGATTTTGCGACTTA<br>CTATTGCCAGCAGCATAATGAGTACCCATGGACTTTTGGCGGTGGCACAAAG<br>GTCGAGATTAAGCGTGCAGCTGCCGGTGGTGGAGGTTCGGGTGGGGGCGGTT<br>CTCATCATCACCATCATCACCATCATGGT | 66 |
| VH3-VL1<br>scFv nucleic<br>acid sequence | | ATGAAATATTTGCTTCCGACTGCCGCCGCAGGTCTGTTACTTTTAGCAGCGC<br>AGCCCGCTATGGCACAGGTCCAGTTAGTTCAATCAGGAGCGGAGGTGAAGAA<br>GCCGGGAGCCACGGTTAAAATCTCATGCAAGGTGTCCGGCTATACATTTACC<br>GACCACACGATTCACTGGATGCAGCAAGCTCCCGGGAAGGGGCTTGAATGGA<br>TGGGGTACAATTATCCACGCGATGGTTCCACCAAGTATAACGAAAAATTTCA<br>AGGTCGTGTCACCATTACCGCTGACAAAAGCACGTCTACAGCGTACATGGAG<br>CTGAGTAGCTTGCGCTCAGAGGACACAGCCGTATACTATTGCGCAAAAGGTT<br>TCATCACGACCGTAGTCCCCTCTGCGTATTGGGGACAGGGGACCCTGGTCAC<br>GGTCTCCTCCGGGGGCGGAGGATCGGGAGGCGGGGGGTCTGGAGGTGGTGGA<br>TCTGACATCCAGCTTACCCAATCGCCTAGCTTCTTGAGTGCTAGTGTAGGCG<br>ACCGTGTTACTATCACTTGTCGCGCTTCTAAGAGCATTAGCAAATACTTAGC<br>CTGGTACCAACAAAAGCCGGGAAAGGCACCCAAGCTGTTAATTTATAGTGGG<br>TCTACCCTTCAGTCCGGCGTACCCTCACGCTTTTCCGGCAGTGGCTCGGGTA<br>CCGAATTTACCCTTACGATTTCTTCGCTTCAACCCGAAGATTTTGCAACGTA<br>CTACTGTCAGCAGCACAACGAGTATCCCTGGACATTCGGCGGAGGGACAAAA<br>GTAGAAATCAAGCGTGCAGCCGCAGGTGGCGGCGGGTCTGGCGGCGGAGGGA<br>GTCACCATCACCATCATCATCATGGA | 67 |
| VH2-VL3<br>scFv nucleic<br>acid sequence | | ATGAAATATTTGTTACCTACCGCTGCGGCAGGACTTCTGCTTTTGGCCGCTC<br>AGCCCGCAATGGCTCAAGTGCAATTGGTTCAGTCAGGGGCCGAAGTAAAAAA<br>GCCAGGCGCGAGCGTAAAAGTGAGTTGCAAGGTCTCCGGTTACACGTTTACC<br>GATCACACGATTCACTGGATGCGTCAAGCTCCAGGCCAGGGTCTTGAATGGA<br>TGGGTTACAACTATCCTCGCGATGGTTCGACCAAGTATAACGAGAAGTTTCA<br>GGGGCCGTGTCACAATGACCGCCGACAAATCAACGAGCACTGTCTACATGGAG<br>CTGTCATCCCTGCGCAGCGAGGATACAGCTGTGTACTACTGTGCCAAGGGCT<br>TCATTACTACCGTCGTCCCCAGCGCGTACTGGGGTCAAGGTACACTGGTAAC<br>AGTTTCATCCGGAGGAGGGGGAAGCGGCGGCGGTGGATCTGGCGGCGGTGGG<br>TCAGACGTTCAACTTACCCAGTCGCCTTCTTCCGTGAGTGCCTCTGTCGGGG<br>ATCGTGTTACCATCACTTGCCGCGCATCTAAGTCAATTTCTAAATATTTGGC<br>CTGGTATCAGCAGAAACCCGGTAAAGCGCCCAAATTGTTGATCTATTCCGGC<br>AGTACCTTGCAATCCGGGGTGCCTTCGCGCTTCTCGGGGAGTGGAAGCGGCA<br>CGGATTTCACTTTAACGATCTCGAGTTTGCAGCCGGAAGATTTTGCGACTTA<br>CTATTGTCAGCAGCATAACGAATATCCATGGACCTTTGGCCCTGGTACGAAA<br>GTAGAAATCAAACGTGCAGCAGCCGGTGGGGGTGGCTCCGGTGGCGGTGGGT<br>CGCATCACCACCACCATCATCATCACGGT | 68 |
| VH2-VL2<br>scFv nucleic<br>acid sequence | | ATGAAGTACCTGTTGCCCACAGCCGCTGCTGGGTTACTGCTTCTTGCTGCCC<br>AGCCCGCAATGGCGCAAGTGCAATTAGTCCAGTCTGGAGCAGAGGTTAAAAA<br>GCCGGGAGCTTCAGTGAAGGTCTCCTGTAAGGTAAGTGGTTATACATTCACC<br>GATCACACAATCCATTGGATGCGCCAGGCCCCAGGTCAGGGTCTTGAATGGA<br>TGGGCTATAACTACCCGCGTGATGGCTCAACTAAGTATAACGAGAAGTTTCA<br>GGGGCGCGTTACAATGACTGCGGATAAAAGCACGTCGACGGTGTACATGGAA<br>TTGTCAAGCCTTCGTTCCGAAGATACCGCAGTTTACTATTGTGCTAAGGGCT<br>TTATCACTACCGTGGTACCCAGTGCGTACTGGGGGCAGGGAACCCTGGTAAC<br>CGTGTCATCGGGCGGAGGCGGAAGCGGGGGAGGTGGCAGTGGAGGTGGCGGG<br>TCTGACGTTCAAATCACCCAGTCACCGTCATTTCTTCCGCGTCTGTGGGTG<br>ACCGCGTAACAATTACTTGCCGTGCTTCGAAAAGCATTTCGAAATACCTTGC | 69 |

| Seq Desc. | Chain | Sequence | SEQ ID |
|---|---|---|---|
| | | CTGGTACCAACAGAAACCGGGGAAAGCAAACAAACTTTTAATCTACAGCGGG<br>AGCACGCTTCAATCCGGCGTCCCATCCCGTTTTTCTGGCTCCGGCAGCGGGA<br>CCGACTTCACCTTAACTATTTCTTCCCTTCAACCGGAGGACTTTGCGACGTA<br>TTACTGTCAACAACACAATGAGTATCCGTGGACTTTCGGAGGCGGAACTAAG<br>GTTGAAATCAAGCGTGCTGCTGCTGGCGGGGGAGGCTCAGGCGGAGGGGGAT<br>CACATCATCATCACCATCATCATCACGGA | |
| VH2-VL1<br>scFv nucleic<br>acid sequence | | ATGAAATACTTGCTGCCGACTGCCGCAGCGGGATTATTATTACTTGCGGCTC<br>AGCCGGCTATGGCGCAGGTCCAGTTAGTTCAGAGTGGGGCAGAAGTGAAGAA<br>ACCCGGTGCATCTGTAAAGGTCTCATGTAAAGTATCTGGCTACACCTTCACT<br>GACCACACTATCCACTGGATGCGTCAAGCACCAGGACAAGGTTTAGAGTGGA<br>TGGGATATAACTATCCGCGTGACGGGAGTACGAAGTATAACGAAAAATTTCA<br>GGGCCGTGTAACCATGACCGCGGATAAATCCACTTCCACTGTCTATATGGAA<br>TTATCGTCGTTACGTAGCGAGGACACGGCGGTATATTATTGCGCCAAAGGGT<br>TTATCACGACTGTTGTGCCGTCCGCTTACTGGGGGCAAGGGACTTTAGTGAC<br>CGTGTCCAGCGGAGGGGGGGGTAGCGGGGGTGGCGGGAGTGGTGGTGGGGGT<br>TCGGACATTCAGCTTACCCAATCCCCTAGCTTTTTGTCAGCCTCCGTTGGCG<br>ATCGTGTAACTATTACGTGCCGCGCCTCCAAGTCCATTTCAAAATATTTAGC<br>CTGGTACCAACAGAAGCCAGGAAAGCTCCTAAATTACTGATTTACTCAGGT<br>TCCACATTGCAGTCGGGCGTACCAAGCCGTTTTTCGGGAAGTGGTAGCGGGA<br>CCGAGTTTACATTGACGATTAGTAGTCTTCAACCGGAGGATTTTGCAACCTA<br>CTATTGTCAGCAGCACAACGAGTACCCATGGACCTTTGGAGGCGGTACCAAA<br>GTGGAAATTAAACGCGCAGCAGCAGGCGGCGGTGGTTCAGGGGGGAGGAGGCT<br>CGCATCACCACCATCATCATCACCACGGT | 70 |
| VH1-VL3<br>scFv nucleic<br>acid sequence | | ATGAAATACCTTTTGCCGACTGCCGCCGCAGGATTATTGTTACTGGCGGCTC<br>AGCCGGCTATGGCCCAAGTCCAATTAGTTCAATCAGGGGCAGAAGTTAAGAA<br>GCCCGGAGCAAGTGTCAAGGTCTCATGCAAAGCCTCCGGTTACACCTTTACC<br>GACCACACGATGCACTGGGTTCGCCAAGCTCCCGGACAGGGCCTGGAATGGA<br>TGGGTTATAATTATCCGCGTGATGGTAGCACGAAATACGCGGAAAAATTCCA<br>AGGTCGCGTTACGATGACCGCGGACAAGTCTACTAGCACCGTGTACATGGAA<br>CTTAGCTCGCTGCGTTCGGAAGATACGGCGGTGTACTACTGTGCGAAAGGTT<br>TCATCACTACAGTAGTGCCAAGTGCGTATTGGGGTCAAGGCACGCTGGTAAC<br>GGTTTCAAGTGGTGGCGGCGGTAGCGGCGGCGGCGGCAGCGGAGGAGGGGGA<br>TCGGATGTCCAACTTACGCAATCTCCGTCCTCTGTTTCCGCAAGTGTGGGCG<br>ACCGCGTAACCATCACTTGCCGTGCTAGTAAAAGCATTTCTAAGTATTTAGC<br>GTGGTATCAACAGAAGCCCGGAAAGGCGCCAAAGCTGTTGATTTATTCCGGG<br>AGTACATTACAATCTGGCGTGCCGTCCCGCTTCTCCGGCAGCGGTAGTGGTA<br>CTGACTTCACGCTGACAATTAGTTCACTTCAGCCAGAGGATTTTGCGACATA<br>TTATTGCCAGCAGCATAACGAATACCCATGGACCTTCGGTCCTGGAACCAAG<br>GTTGAAATCAAACGTGCTGCGGCCGGCGGCGGTGGGAGCGGAGGGGGCGGGT<br>CACATCATCATCATCATCACCATCATGGT | 71 |
| VH1-VL2<br>scFv nucleic<br>acid sequence | | ATGAAATACCTTCTTCCCACCGCAGCAGCGGGATTGTTATTATTGGCTGCAC<br>AACCTGCGATGGCTCAAGTACAGTTGGTGCAGTCAGGGGCGGAAGTCAAGAA<br>ACCAGGCGCTTCAGTGAAAGTTTCGTGTAAAGCATCCGGCTATACTTTTACC<br>GACCACACCATGCACTGGGTTCGCCAAGCTCCTGGACAGGGTCTGGAATGGA<br>TGGGGTACAACTATCCCCGCGATGGATCCACAAAGTACGCGGAGAAGTTCCA<br>AGGACGTGTAACAATGACGGCCGATAAAAGCACTTCCACAGTCTATATGGAA<br>CTTTCGTCTCTTCGTTCTGAGGACACAGCAGTTTACTACTGTGCTAAAGGAT<br>TTATCACTACCGTCGTTCCGTCTGCATATTGGGGGCAGGGCACGTTAGTAAC<br>AGTCAGCTCCGGGGGCGGGGGCTCAGGGGGCGGTGGATCAGGGGGGAGGCGGC<br>TCTGACGTGCAGATCACTCAGTCGCCCTAGCTTTCTTTCGGCTAGTGTCGGGG<br>ATCGCGTCACTATCACATGCCGCGCCAGCAAAAGCATCTCTAAATACCTGGC<br>TTGGTACCAACAAAAACCCGGAAAGGCTAATAAGTTGCTGATCTACAGTGGG<br>AGTACTTTGCAGTCGGGGGTGCCGAGTCGTTTTTCAGGTAGCGGGTCGGGCA<br>CGGACTTTACCCTTACAATTTCCTCCCTGCAGCCCGAGGACTTTGCCACATA<br>TTATTGTCAACAGCACAACGAGTACCCGTGGACGTTTGGGGGAGGTACCAAA<br>GTGGAAATCAAGCGTGCAGGCCGGCGGGGGAGGTGGAAGCGGCGGCGGTGGAA<br>GTCACCATCATCACCACCACCATCACGGA | 72 |
| VHI-VL1<br>scFv nucleic<br>acid sequence | | ATGAAATACCTGTTACCTACTGCTGCCGCAGGTTTGTTGCTTCTGGCGGCTC<br>AACCGGCCATGGCACAGGTTCAGCTGGTGCAATCAGGCGCCGAAGTCAAAAA<br>ACCCGGGTGCAAGCGTCAAGGTGAGCTGTAAGGCAAGCGGATATACTTTTACA<br>GATCATACAATGCACTGGGTACGCCAGGCACCAGGCCAGGGCCTTGAATGGA<br>TGGGATATAACTACCCACGTGATGGATCTACTAAATATGCCGAGAAGTTCCA<br>GGGTCGCGTTACCATGACTGCTGATAAAGTACATCAACTGTATACATGGAA<br>CTTAGCTCATTGCGTTCCGAAGATACTGCCGTGTACTATTGTGCAAAGGGGT<br>TTATCACGACAGTCGTTCCATCGGCATATTGGGGCAGGGAACGTTAGTAAC<br>AGTCAGCAGTGGGGGTGGGGGGTCAGGCGGAGGAGGGTCTGGTGGGGGGGGT<br>TCTGACATCCAGTTGACACAGTCCCCATCCTTTTTGTCTGCATCGGTTGGGG<br>ACCGCGTGACGATTACTTGTCGCGCGTCCAAGTCTATCAGCAAATATTTAGC<br>ATGGTATCAACAAAAACCTGGCAAGGCTCCCAAGTTACTTATTTACTCCGGT<br>AGTACTCTTCAGTCGGGAGTGCCTTCCCGTTTTAGCGGGTCTGGTTCAGGCA | 73 |

| Sequence Listing of the Present Disclosure: | | | |
|---|---|---|---|
| Seq Desc. | Chain | Sequence | SEQ ID |
| | | CGGAGTTTACCCTTACAATTAGTTCTCTGCAGCCCGAGGATTTTGCAACTTA CTACTGCCAGCAACACAATGAGTACCCCTGGACATTCGGCGGTGGGACAAAA GTCGAGATTAAGCGTGCCGCTGCCGGTGGAGGAGGGTCAGGGGGTGGCGGCA GTCATCACCACCATCACCATCATCATGGA | |
| 6B5 scFv nucleic acid sequence | | ATGAAGTACTTATTGCCCACTGCTGCTGCTGGATTATTATTGTTGGCAGCGC AACCGGCCATGGCGCAGGTCCAACTTCAGCAGTCAGATGCCGAACTTGTAAA GCCGGGTGCAAGCGTGAAAATCTCATGTAAAGTATCTGGTTATACGTTTACA GATCACACCATCCACTGGATGAAGCAACGCCCTGAGCAGGGTTTAGAGTGGA TTGGCTATAATTATCCGCGCGACGGTTCGACAAAATACAACGAAAAGTTCAA GGGCAAGGCAACGCTTACCGCCGATAAGAGTTCAAGTACAGCATATATGCAA CTGAACAGCTTAACTAGCGAAGATAGCGCAGTTTACTTTTGCGCGAAGGGAT TTATCACCACCGTGGTTCCGAGTGCCTACTGGGGACAGGGCACATTGGTTAC AGTCAGTGCAGGAGGAGGAGGGTCCGGTGGCGGAGGATCGGGTGGGGGTGGA TCAGATGTCCAAATCACACAATCGCCATCCTACTTGGCCGCCTCGCCCGGAG AAACCATCACTATTAATTGCCGCGCGAGCAAGTCTATTTCCAAGTATTTGGC ATGGTACCAAGAAAAGCCCGGTAAAACTAACAAACTTTTGATCTACTCTGGG TCCACGCTGCAGTCAGGAATCCCATCCCGTTTCTCGGGCAGCGGATCTGGGA CAGACTTCACGTTGACAATTTCGAGCCTTGAGCCGGAAGATTTCGCAATGTA CTACTGTCAGCAACATAACGAGTACCCTTGGACATTTGGCGGGGGCACAAAG CTTGAAATTAAACGCGCTGCTGCCGGAGGAGGTGGTTCGGGGGGGAGGGGGTT CTCATCATCACCACCATCACCACCACGGA | 74 |
| Signal sequence | | MEWSWVFLFFLSVTTGVHS | 75 |
| C-terminal tag | | RAAAGGGGSGGGGSHHHHHHHH | 76 |

The invention claimed is:

1. An anti-ceramide antibody or antigen-binding fragment thereof comprising an immunoglobulin heavy chain variable region (VH) comprising a heavy chain complementarity determining region (CDR) 1 (HCDR1), a heavy chain CDR2 (HCDR2), and a heavy chain CDR3 (HCDR3), and an immunoglobulin light chain variable region (VL) comprising a light chain CDR1 (LCDR1), a light chain CDR2 (LCDR2), and a light chain CDR3 (LCDR3), wherein:

(a) the HCDR1 comprises an amino acid sequence selected from the group consisting of SEQ ID NO: 1 and 2;

(b) the HCDR2 comprises an amino acid sequence selected from the group consisting of SEQ ID NO: 3, 4, 5, and 6;

(c) the HCDR3 comprises SEQ ID NO: 7;

(d) the LCDR1 comprises SEQ ID NO: 8;

(e) the LCDR2 comprises SEQ ID NO: 9; and (f) the LCDR3 comprises SEQ ID NO: 10.

2. The anti-ceramide antibody or antigen-binding fragment thereof of claim 1, wherein:

(i) the HCDR1 comprises SEQ ID NO: 1 and the HCDR2 comprises SEQ ID NO: 3;

(ii) the HCDR1 comprises SEQ ID NO: 1 and the HCDR2 comprises SEQ ID NO: 4;

(iii) the HCDR1 comprises SEQ ID NO: 1 and the HCDR2 comprises SEQ ID NO: 5;

(iv) the HCDR1 comprises SEQ ID NO: 1 and the HCDR2 comprises SEQ ID NO: 6;

(v) the HCDR1 comprises SEQ ID NO: 2 and the HCDR2 comprises SEQ ID NO: 3;

(vi) the HCDR1 comprises SEQ ID NO: 2 and the HCDR2 comprises SEQ ID NO: 4;

(vii) the HCDR1 comprises SEQ ID NO: 2 and the HCDR2 comprises SEQ ID NO: 5; or (viii) the HCDR1 comprises SEQ ID NO: 2 and the HCDR2 comprises SEQ ID NO: 6.

3. The anti-ceramide antibody or antigen-binding fragment thereof of claim 1, wherein:

(i) the VH comprises an amino acid sequence that is at least 90% identical to SEQ ID NO: 17 and the VL comprises an amino acid sequence that is at least 90% identical to SEQ ID NO: 22;

(ii) the VH comprises an amino acid sequence that is at least 90% identical to SEQ ID NO: 17 and the VL comprises an amino acid sequence that is at least 90% identical to SEQ ID NO: 23;

(iii) the VH comprises an amino acid sequence that is at least 90% identical to SEQ ID NO: 17 and the VL comprises an amino acid sequence that is at least 90% identical to SEQ ID NO: 24;

(iv) the VH comprises an amino acid sequence that is at least 90% identical to SEQ ID NO: 18 and the VL comprises an amino acid sequence that is at least 90% identical to SEQ ID NO: 22;

(v) the VH comprises an amino acid sequence that is at least 90% identical to SEQ ID NO: 18 and the VL comprises an amino acid sequence that is at least 90% identical to SEQ ID NO: 23;

(vi) the VH comprises an amino acid sequence that is at least 90% identical to SEQ ID NO: 18 and the VL comprises an amino acid sequence that is at least 90% identical to SEQ ID NO: 24;

(vii) the VH comprises an amino acid sequence that is at least 90% identical to SEQ ID NO: 19 and the VL comprises an amino acid sequence that is at least 90% identical to SEQ ID NO: 22;

(viii) the VH comprises an amino acid sequence that is at least 90% identical to SEQ ID NO: 19 and the VL comprises an amino acid sequence that is at least 90% identical to SEQ ID NO: 23;

(ix) the VH comprises an amino acid sequence that is at least 90% identical to SEQ ID NO: 19 and the VL comprises an amino acid sequence that is at least 90% identical to SEQ ID NO: 24;

(x) the VH comprises an amino acid sequence that is at least 90% identical to SEQ ID NO: 20 and the VL comprises an amino acid sequence that is at least 90% identical to SEQ ID NO: 22; or (xi) the VH comprises an amino acid sequence that is at least 90% identical to SEQ ID NO: 21 and the VL comprises an amino acid sequence that is at least 90% identical to SEQ ID NO: 22.

4. An anti-ceramide antibody or antigen-binding fragment thereof comprising an immunoglobulin heavy chain variable region (VH) and an immunoglobulin light chain variable region (VL), wherein the VH comprises an amino acid sequence selected from the group consisting of SEQ ID NO: 17, 18, 19, 20, and 21; and wherein the VL comprises an amino acid sequence selected from the group consisting of SEQ ID NO: 22, 23 and 24.

5. The anti-ceramide antibody or antigen-binding fragment thereof of claim 4, wherein:

the VH comprises SEQ ID NO: 20 and the VL comprises SEQ ID NO: 22.

6. The anti-ceramide antibody or antigen-binding fragment thereof of claim 1, wherein the antibody or antigen-binding fragment is humanized.

7. The anti-ceramide antibody or antigen-binding fragment thereof of claim 1, wherein the antigen-binding fragment is a single chain variable fragment (scFv).

8. The anti-ceramide antibody or antigen-binding fragment thereof of claim 7, wherein the scFv comprises an amino acid sequence that is at least 90% identical to a sequence selected from the group consisting of SEQ ID NOs: 48-61.

9. The anti-ceramide antibody or antigen-binding fragment thereof of claim 7, wherein the light chain variable region of said scFv is carboxy-terminal to the heavy chain variable region of said scFv.

10. A polynucleotide encoding the anti-ceramide antibody or antigen-binding fragment thereof of claim 1.

11. An anti-ceramide single chain variable fragment (scFv) comprising SEQ ID NO: 48, 49 or 51.

12. A polynucleotide encoding the anti-ceramide single chain variable fragment (scFv) of claim 11.

13. An expression vector comprising the polynucleotide of claim 10.

14. A host cell comprising the polynucleotide of claim 10.

15. A method of manufacturing the anti-ceramide antibody or antigen-binding fragment thereof of claim 1, comprising introducing an expression vector encoding the anti-ceramide antibody or antigen-binding fragment thereof into a host cell.

16. A method of inhibiting apoptosis in a subject in need thereof, comprising administering to the subject a therapeutically effective amount of the anti-ceramide antibody or antigen-binding fragment thereof of claim 1.

17. The method of claim 16, wherein the apoptosis is associated with a disease selected from the group consisting of graft versus host disease, radiation disease, GI syndrome, and autoimmune disease.

18. The method of claim 17, wherein the disease is radiation disease or GI syndrome.

19. The method of claim 16, wherein the anti-ceramide antibody or antigen-binding fragment thereof is administered intravenously, intramuscularly, intraperitoneally, intracerebrospinally, subcutaneously, intrasynovially, intrathecally, orally, topically, or via inhalation.

20. A method for mitigating apoptosis in a subject with GI syndrome comprising administering to the subject an effective amount of the anti-ceramide antibody or antigen-binding fragment thereof of claim 1, after the subject is exposed to penetrating radiation.

21. The method of claim 20, wherein the anti-ceramide antibody or antigen-binding fragment thereof is administered immediately after, or within 24 hours after, the subject is exposed to penetrating radiation.

22. A method for inhibiting apoptosis in a subject with graft versus host disease (GvHD) comprising administering to the subject an effective amount of anti-ceramide antibody or antigen binding fragment thereof of claim 1, either before the subject receives a transplant or after the subject receives a transplant prior to the onset of GvHD.

23. The method of claim 22, wherein the transplant is a bone marrow transplant.

24. The anti-ceramide antibody or antigen-binding fragment thereof of claim 1, wherein the HCDR1 comprises SEQ ID NO: 1 and the HCDR2 comprises SEQ ID NO: 4.

* * * * *